(12) United States Patent
Marechal et al.

(10) Patent No.: US 10,590,444 B2
(45) Date of Patent: Mar. 17, 2020

(54) INCREASED TRIACYLGLYCEROL PRODUCTION IN MICROALGAE

(71) Applicant: TOTAL RAFFINAGE CHIMIE, Courbevoie (FR)

(72) Inventors: Eric Marechal, Grenoble (FR); Lina Dolch, Düsseldorf (DE)

(73) Assignee: TOTAL RAFFINAGE CHIMIE, Courbevoie (FR)

( * ) Notice: Subject to any disclaimer, the term of this patent is extended or adjusted under 35 U.S.C. 154(b) by 0 days.

(21) Appl. No.: 16/069,080

(22) PCT Filed: Jan. 27, 2017

(86) PCT No.: PCT/EP2017/051823
§ 371 (c)(1),
(2) Date: Jul. 10, 2018

(87) PCT Pub. No.: WO2017/129777
PCT Pub. Date: Aug. 3, 2017

(65) Prior Publication Data
US 2019/0017082 A1   Jan. 17, 2019

(30) Foreign Application Priority Data

Jan. 29, 2016 (EP) .................................. 16153390

(51) Int. Cl.
*C12P 7/64* (2006.01)
*C12N 9/02* (2006.01)
*C12N 15/82* (2006.01)
*C07K 14/405* (2006.01)

(52) U.S. Cl.
CPC .......... *C12P 7/6463* (2013.01); *C07K 14/405* (2013.01); *C12N 9/0075* (2013.01); *C12Y 114/13039* (2013.01)

(58) Field of Classification Search
CPC .......... C12N 1/12; C12N 1/38; C12N 9/0075; C12Y 114/13039; C12P 7/6463
USPC .............................. 435/244, 257.1, 158, 159
See application file for complete search history.

(56) References Cited

U.S. PATENT DOCUMENTS

2010/0178671 A1   7/2010  Nguyen et al.

FOREIGN PATENT DOCUMENTS

| WO | 2009125401 | 10/2001 |
| WO | 2013126076 | 8/2013 |
| WO | 2015008160 | 1/2015 |
| WO | 2017129777 | 8/2017 |

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Saktivel et al.( J. Exprt sci 2011, 2, pp. 29-49.*
Foresi et al., "Characterization of a Nitric Oxide Synthase from the Plant Kingdom: NO Generation from the Green Alga *Ostreococcus tauri* is Light Irradiance and Growth Phase Dependent",The Plant Cell, Nov. 2010; 22: 3816-3830.
Gomma et al., "Improvement in Oil Production by Increasing Malonyl-CoA and Glycerol-3-Phosphate Pools in Scenedesmus quadricauda", Indian Journal of Microbiology, Hisar, IN, Aug. 7, 2015; 55(4): 447-455.
Vardi et al., "A Diatom Gene Regulating Nitric-Oxide Signaling and Susceptibiiity to Diatom-Derived Aldehydes", Current Biology, Jun. 24 2008; 18(12): 895-899.
Valeria et al., "Transcriptome sequencing of three Pseudo-nitzschia species reveals comparable gene sets and the presence of Nitric Oxide Synthase genes in diatoms", Scientific Reports, Jul. 20, 2015; 5-12329, total 14 pages

* cited by examiner

*Primary Examiner* — Robert B Mondesi
*Assistant Examiner* — Mohammad Y Meah
(74) *Attorney, Agent, or Firm* — James S. Keddie; Bozicevic, Field & Francis LLP

(57) ABSTRACT

The application generally relates to bioproduction of molecules of interest in micro-organisms, more particularly in microalgae. In particular, the application relates to methods for increasing triacylglycerol production in micro-organisms, in particular in microalgae, using recombinant microorganisms which have been genetically engineered to produce or overproduce nitric oxide (NO) and uses thereof.

10 Claims, 21 Drawing Sheets

Specification includes a Sequence Listing.

```
              1                                                    50
    PtNOA     ..........  ..........  ..........  ..........  ..........
    NgNOA     MAPHLSGLNF  HSLVKRSSAA  ALLFSLFIMK  LPCVGAFQGV  VRVWSSAVAP
 Consensus    ..........  ..........  ..........  ..........  ..........

51                                                   100
    PtNOA     ..........  ..........  ..........  ..........  ..........
    NgNOA     SRAAVLTSFM  SPKRHVLKRM  PISALCRRST  IMASRKAGAG  QGEHEAEGEG
 Consensus    ..........  ..........  ..........  ..........  ..........

101                                                   150
    PtNOA     MVPTGCMRSK  NKQSTAADGR  RSIGSRSNAG  LVMFFSMTIL  STRRFAAAWV
    NgNOA     ISPESISSTG  SNAGGKGIGR  GPRNRRKIAV  SAEEEEFSAL  SDSRTSVSEE
 Consensus    isPegcmrsg  nnaggaadGR  rprnrRknAg  laeeeemsaL  SdrRfaaaee 151                                                   200
    PtNOA     FQSSGIQRSI  ..PSTHRMRT  NFALSTRCFA  SSSDNHDEEE  QRDSPKQRSK
    NgNOA     KDSIRRPRVI  SRPPSRPVKR  TMTINPNWRA  HGGPENSIKG  PEEAASSSSG
 Consensus    k#SirrqRsI  ..Ppsrrmrr  nmainprcrA  hggd#ndeee  qr#aakqrSg 201                                                   250
    PtNOA     RSQTNRSKKF  K.........  ...IAESIDQ  SKIDKLAQAF  DELAR...KE
    NgNOA     TAGSGKARVG  KNGPRGASPL  GAEVPRYVED  EDEDGITFPK  DMVIRGLDSQ
 Consensus    raqsnrarkg  K.........  ...!ars!##  edeDgiaqak  DelaR...k#
```

FIG. 1A (cont.)

```
          251                                                  300
PtNOA     GFDSST..AR FADDVTFEDK FDDDSFL... DDDDDNNKDK VGNLHLDASM
NgNOA     SYEEARRQAV LSDDEGEEEE WADEGVMVEE EEGEDFDEEE EEEDFDEEEE
Consensus g%#ear..Ar laDDegeE#e faD#gf$... ##d#Dn#e#e ee#dhd#aee 301                                                  350
PtNOA     FSLSDFIDKS EEDGGN.... .PTDQDDEDY LDFGADIDMS IEARI..AAA
NgNOA     EEDFDEGDEE EEDGAHLPPV RPVSMEERLR LAESGNIFNP YVARMHTRAG
Consensus eedfDegDee EEDGan.... .Ptdq##rdr Laega#Idnp ieARi..aAa 351                                                  400
PtNOA     KRDMDLGRVS APPDMRSSRR EVTAADLRKL GFRTEANPFG NDETPRKERF
NgNOA     TGEGPSGEAE DPGPMDGGGL RFLEEDVSPG EKREEARRAQ APSLPVKFQY
Consensus kr#gdlGrae aPgdMrggrr rflaaDlrkg ekReEArraq adelPrKer%

401                                                  450
PtNOA     QLVTNSMSCS ACGSDFQCHN EDRPGYLPPE KF....ATQT ALGKIEQMQK
NgNOA     KVVVGAGTCP GCGNAFQTKN ESSPGFLPPD VYERLQAQMT ALRPGAPRKP
Consensus qlVtnagsCp aCGnaFQchN EdrPG%LPP# k%....AqqT ALrkgaqrqk 451                                                  500
PtNOA     LQDKA..... ......EKAE WTPED..... ....EIEWLI QTQGKKDPNK
NgNOA     RPDAPPLSKS AAGALRKKTE TRGEEGDLFQ GLSAEEEVEM LLSGKSREEF
Consensus rqDaa..... ......eKaE trgE#..... ....EeEwei qlqGKkre#k
```

FIG. 1A (cont.)

```
           501                                                       550
    PtNOA  EMQEVPQIDV DSLAGEMGLD LVELSK.... .......... .........K
    NgNOA  EIERAAGRGR EAQGGEVDLD LDEEGKEEKE GEGREGEEGG EGEEEEEEFR
Consensus  Ei#raaqrdr #aqaGEmdLD LdEegK.... .......... .........r 551                                                       600
    PtNOA  MVICKRCHGL QNFGKVQDSL RPGWTKEPLL SQEKFRELLR PIKEKPAVIV
    NgNOA  AVICQRCHKL KHYGDVEDAL RPGWSANELL TPERFRELVS VVRRKRCAVV
Consensus  aVICqRCHgL qn%GdV#DaL RPGWsa#eLL sqErFRELlr p!rrKraa!V 601                                                       650
    PtNOA  ALVDLFDFSG SVLPELDEIA GENPVILAAN KADLLPSEMG RVRAESWVRR
    NgNOA  CLVDIFDFHG SLLYNLPRIV GSNPVLVAVN KADLLPADFS QDRVRIWVKQ
Consensus  aLVDiFDFhG Slp#LdrIa GeNPVilAaN KADLLPa#mg rdRariWVrr 651                                                       700
    PtNOA  ELEYLGVKSL AGMRGAVRLV SCKTGAGIND LLEKARGLAE EIDGDIYVVG
    NgNOA  ELEKVGMTDV STRD..IHLI SCKTGNNVRP LLRSMKQMAR QRRRDLYVIG
Consensus  ELEklGmkdl agrr..!rL! SCKTGan!rd LLrkarq$Ar #rrrDiYV!G 701                                                       750
    PtNOA  AANAGKSTLL NFVLGQDKVN ...RSPGKAR AGNRNAFKGA VTTSPLPGTT
    NgNOA  AANVGKSTFI NRLIELGRSG GDAQRKKKKK QGEQSKGGSL VTTSALPGTT
Consensus  AANaGKSTli Nrlieqdrsn ...rrkgKar aG#rnaggga VTTSaLPGTT
```

FIG. 1A (cont.)

```
           751                                                        800
    PtNOA  LKFIKVDLGG GRSLYDTPGL LVLGTVTQLL TPEELKIVVP KKPIEPVTLR
    NgNOA  LDFIEVDLGD KVSLYDTPGL ILPHQITTLL NTEELKAVIP QKRINHVTLR
Consensus  LdFIeVDLGd grSLYDTPGL illgq!TqLL npEELKaV!P qKrI#hVTLR 801                                                        850
    PtNOA  LSTGKCVLVG GLARIELIGD SRPFMFTFFV ANEIKLHPTD IERADEFVLK
    NgNOA  LKEGKSVLLG GLVRLDML.E GRPFLFTFYV SNEVKLHQTA TDRAGEFLDS
Consensus  LkeGKcVL1G GLaRi#$i.# gRPF$FTF%V aNE!KLHqTa i#RAdEFldk 851                                                        900
    PtNOA  HAGGMLTPPL APGPKRMEEI GEFEDHIVDI QGAGWKEAAA DISLTGLGWV
    NgNOA  HLGELISPPF TQ..ERRAAM GPWVPRDFEI EGTGWKTSAV DIVISGLGWI
Consensus  HaGe$isPPl aq..eRraai Gefedrdf#I #GaGWKeaAa DIsisGLGW!

901                                                        950
    PtNOA  AVTGAGTAQV KISVPKGIGV SVRPPLMPFD IWKVASKYTG SRAVRKSSKL
    NgNOA  SVTGALDCKV RVMAPEAVGV RLRSPLMPYE TWATTAKWTG LRAVKSDKQK
Consensus  aVTGAgdaqV r!maPea!GV rlRpPLMP%# iWataaKwTG lRAVrkdkql 951        962
    PtNOA  ANGKRRKGVG RN   (SEQ ID NO: 2)
    NgNOA  GSSR...... ..   (SEQ ID NO: 4)
Consensus  angr...... ..
```

SEQ ID NO:3

ATTTTCTTGTTATCTTATACACACATATTCACAGGAGGATTGTAATTAGTGAAACTGGT
GGCAAAGGGTTTATCAACGGTGGCTGCGCTTCTTCCTGCCCATCGAACAGCAACTTCAG
CCACTCAAACCACATTACTTTTCGCCCTGTGAATTTTTGGTCAACTTCATGGCACCACA
CTTGAGTGGCCTAAATTTTCATTCATTGGTCAAGAGATCGTCCGCTGCAGCGCTTCTTT
TCTCGCTCTTCATCATGAAGCTACCCTGTGTCGGTGCTTTCCAAGGAGTAGTGCGGGTT
TGGAGTTCAGCAGTGGCTCCATCGCGAGCTGCCGTACTCACCAGCTTTATGTCTCCCAA
ACGACACGTGCTAAAAAGAATGCCAATTTCAGCGTTGTGCAGGCGGTCAACAATCATGG
CGTCCCGGAAAGCGGGGCGGGACAGGGCGAGCACGAGGCAGAAGGGGAGGGAATCTCA
CCAGAATCGATCTCGTCGACAGGAAGCAACGCAGGAGGCAAAGGAATCGGGCGCGGACC
CCGAAATCGACGGAAAATAGCCGTAAGCGCGGAAGAGGAAGAGTTTTCAGCCCTGTCCG
ACTCGAGGACCTCGGTTTCCGAAGAGAAGGACTCGATTCGAAGGCCGCGGGTCATTTCT
CGCCCTCCCTCCCGCCCCGTCAAGCGAACGATGACCATCAACCCTAATTGGCGGGCGCA
TGGAGGCCCTGAGAACAGTATAAAGGGACCGGAGGAGGCCGCTTCGTCGTCCTCTGGTA
CCGCGGGGAGCGGAAAGGCCCGTGTGGGAAAGAATGGGCCGCGGGGTGCGAGTCCCCTG
GGGGCGGAGGTACCCCGCTATGTGGAGGATGAGGATGAGGATGGGATCACGTTCCCGAA
AGATATGGTAATCCGAGGCTTGGATAGCCAGAGCTACGAGGAAGCGCGCCGACAGGCCG
TGCTGAGCGATGACGAGGGCGAGGAGGAGGAGTGGGCCGACGAGGGGGTCATGGTGGAG
GAGGAGGAGGGGGAGGACTTTGACGAGGAGGAGGAGGAGGAAGACtTTGACGAGGAGGA
GGAGGAGGAAGACTTTGACGAGGGGGACGAAGAGGAGGAGGACGGCGCTCACCTTCCCC
CAGTGCGGCCCGTGTCGATGGAGGAGCGCCTCCGCCTGGCGGAGTCCGGCAATATCTTC
AACCCCTACGTAGCCCGGATGCACACGCGCGCGGGCACCGGGGAGGGGCCGTCTGGGGA
GGCGGAAGACCCTGGCCCGATGGACGGGGGCGGTTTGCGGTTCTTGGAGGAGGATGTGA
GCCCGGGGGAGAAAAGGGAGGAAGCGCGCCGGGCCCAGGCGCCCTCCCTGCCCGTCAAG
TTCCAGTACAAGGTGGTGGTGGGGGCCGGGACGTGCCCGGGCTGCGGGAACGCGTTTCA
GaCCAAAAATGAATCCTCCCCCGGCTTcCTCCCCCCCGACGTCTACGAGCGGCTTCAGG
CCCAGATGACGGCGCTGCGACCAGGCGCTCCCCGAAAGCCGAGGCCGGAcGCCCCCCCC
CTCTCGAAGTCAGCGGCAGGGCGCTGCGGAAGAAGACGGAGACGAGGGGGGAAGAGGG
GGATTTGTTCCAAGGCCTGAGCGCAGAGGAGGAGGTGGAAATGCTTTTGTCGGGCAAGA
GCCGTGAGGAGTTTGAAATAGAGAGAGCGGCGGGGAGAGGGAGGGAGGCCCAGGGCGGG
GAGGTAGATCTTGACCTCGACGAGGAGGGGAAGGAAGAGAAGGAGGGAGGGAAGGGA
AGGGGAAGAAgGGGGGGAAgGGGAGGAGGAGGAGGAAGAATTTCGTGCGGTAATTTGCC
AGCGGTGCCACAAGCTGAAGCACTACGGGGACGTGGAGGACGCCCTGCGCCCGGGGTGG
AGCGCGAACGAGCTGTTGACGCCGGAGCGCTTCCGGGAGTTGGTGAGCGTGGTGCGACG
GAAACGCTGCGCCGTGGTGTGTCTGGTGGACATCTTCGACTTCCATGGGTCCCTTCTCT
ACAACCTGCCCCGCATCGTGGGCTCCAACCCGGTGCTGGTGGCCGTGAACAAGGCTGAC

FIG. 1B (cont.)

CTCCTCCCCGCGGACTTCAGCCAGGACCGAGTCCGGATCTGGGTCAAGCAGGAACTGGA
GAAGGTGGGGATGACGGACGTGAGCACGCGCGACATCCACCTGATCTCCTGCAAGACGG
GGAACAACGTCCGGCCCTTGCTGCGGTCCATGAAGCAAATGGCGCGCCAGCGCAGGCGG
GATCTGTACGTGATCGGCGCGGCAAACGTGGGCAAGTCGACCTTCATCAACCGGCTGAT
TGAGCTGGGTCGGAGTGGAGGGGACGCGCAGAGGAAGAAGAAGAAGCAGGGGGAAC
AGAGCAAAGGCGGGTCTCTGGTCACGACGAGCGCCTTACCGGGCACGACCTTGGACTTC
ATCGAGGTGGACCTGGGGACAAGGTCTCCCTCTACGACACCCGGGCCTCATCTTGCC
GCACCAGATCACCACGCTGCTGAACACGGAAGAGCTCAAGGCAGTAATTCCCCAGAAGC
GCATCAACCACGTGACCCTGCGCCTGAAGGAGGGCAAGAGCGTCCTCCTGGGCGGGCTA
GTCCGCTTGGACATGCTGGAGGGTCGGCCCTTCCTCTTCACATTCTACGTCTCGAACGA
GGTCAAGCTCCACCAAACAGCCACGGACCGGGCCGGGGAATTTTTGGACAGTCACCTCG
GTGAACTAATCTCGCCGCCCTTCACGCAGGAACGCCGAGCGGCCATGGGGCCATGGGTA
CCTCGTGACTTCGAGATCGAAGGGACGGGCTGGAAAACCTCAGCCGTTGACATAGTCAT
CTCTGGCTTAGGGTGGATATCTGTCACCGGCGCATTGGACTGTAAGGTCCGAGTCATGG
CACCGGAGGCGGTGGGTGTGCGTTTGCGGAGTCCATTGATGCCTTACGAGACCTGGGCG
ACAACAGCCAAGTGGACGGGGCTCAGGGCCGTCAAGAGTGACAAGCAAAAGGGAGCAG
CAGATAGGAAGAGGAAAGTTTTACCCTGTCGTGAAAGTGCTGATGAAGATAAACTATCA
AGAAAATAATCATGTGCATTCACAAAAACAGCTCGTTGTTGTTTTTTGTTTCCTCTTT
GATCAGACCTTTGGTGATATTCGATTCTATTTCTTGCCCGCATCTCATAGGATTGCGAT
TGTAATCTCCGCAACAGCGTTCAACCAGAAAACGTACAACGATCTGAGCAAAGGATAGA
TGGCTAACTCTGGGAGGTCTTTTGCTTGGTATTTGTAGCCGGAAGATGGCTTTGTGGTC
CAGGGCTTGTATTTTCTGGCCCCACGACTGATCTACGTCCAGAGGGGTCTGAGGGACT
CCATGCAAGCCACCAAGCACGTACATTTCACACGCTCGTACATTACGGCATTTTACGCT
CCGATATCGCGCCACGGGAATGATTGGTCACGCCCATCAAAGCACTCGCCGGTTCTTTC
ATCTCTATACTCAAATATCCTTACCCTTCCTCGACAGTCGACGCACGATGAACTTCGCG
GACGCTGCCACGACGCACTCAGCCGTGGAAGGCCATGCCTCCCAGGGGACCGAAAGGGA
GGACCAAGCTGGTGGTGACGCTGGAAGGACCTCCCTAGCCATGGCATGACCGGCCCTCT
TCACGACGTGAAGGACACAGAAGACGACACCGACTGCGTTGTTTATGTCCTCAATTTTC
ACCCCCGCAACACGGCGGACAAGGAAGGCAAGATCAACAATGCGATCAACTTCGCCGAT
GCAGAATTGGAGGAACATCACGTCCTCCTGGGAGTGTTTCTTGGTCAATGTGTCGTTTC
CCACCTCCTTCCACCCAAACGCAATTCTAATACCTTGTACCTTGTTGCCCGAATACCAA
CACCTCGTACCCCTAACACGCACAACACGCTTTCCGACAACGCCGGAAGACTCCCCGTC
CGTACACGCGACCCCCTTAACCGCGCCGACATCGAGCCGGACTACTACAAGCCCTTCGT
CTCCCCTGAGCTTGTCAACAAACGCAATGCAGAGGCGCACAAGCACAATTCGCCTCTAC
TCCGCGGTGACCTAAACGTGACGTACGAGCGTACACAGGACAAGGGCTTCTTGGAACTT
GGCCGTGCGCGGAGTGCCACAAAATTTGAGTCCTGGCTTGGTCTTCGCATCATAATCGA
AGGTCCAGCTTTGAACGACCCCGGCCCAAGCAACACGAGCAGATCGTGTGGGTCGATGA
ATACAAGTTTACCAATGGGCAGGATTTCAAGGTGTTCTTTTGGGCGGGAGCCTGTGGC
AGCTGTGCAAGAAGTGGGCCGATGCGAACCGCACTCAATCGGGGGGAGACGACATGGTG

FIG. 1B (cont.)

```
CGTTTTTGTTTCGAGGCCCACTCCGCTTGGTGTTCGTGCATGCTCACAACGTCCAGACG
CACCTCTTCTAGACACAGGACCGGGCGGTGGAGGCGGGCTACATAGCGCCATCCTTGGA
TGTTGGCGCCACGAAAGCCCTGGTAGCATCCAGTGGAATAGAAACCCTCTTCCAGCACG
TGGCTGTGATAAAGAACAAGTAAGCGCACATCCATGATTGGACATCTTACCCTTCCGTG
CATGCATTTCTGGTTGCTCGTTCCGCTCATTTATGGACGCCATCCCTACAGAGCAAAGG
ATCTCGATTGAGGAGGCGGCTTTGGGAGAGCAGCAGCGGGAGATGGTCCGGAGGACCAA
CACAATGGGGGAAATCATCGGTGTTTGTCTTGCTCTCCGGACCCTGTACAACCTTTAAA
AATTGCCCCGTTCTCGCCTTTCACGGAGCAAGATGGCGCTCGGCGTTGCAAGCGCCCAG
CACAATGCGCTCGCAGACCACGCCGGCATAGACCTGTCGGACGTCGCCTCGCTTGACTT
CCACAGCAGCAGCGGCGGCCGCATGCACTCACGGGGGATCACATCGAAACCCGCGCAG
ACGCAGAGGACGCGAAAAGCATCCTCAACCGTCTGAAGGGTGGGAAAGAAAACATCCAC
GAGCTTCGGCAGTGTGATTTCTCACCCGTACGCCCCAAGCCGGGGACGAAAGGGTACTC
TCCACAAGAATTTTTATTTCGTCGGCCGTGAAGCGCGTCAAGTGCTCCACGTGAATGCG
GAGGAAGGCGAAAACGGCATGGAGGGTACGCGGCCTTGTAGGATCGTTGTACCGTGGCT
CAGGGTTCGCACTCACGCCATTGCTAAGGATGGTTAAGAAAGTTGAGCTaAAAAAAAAC
ATCCCTAACCA
```

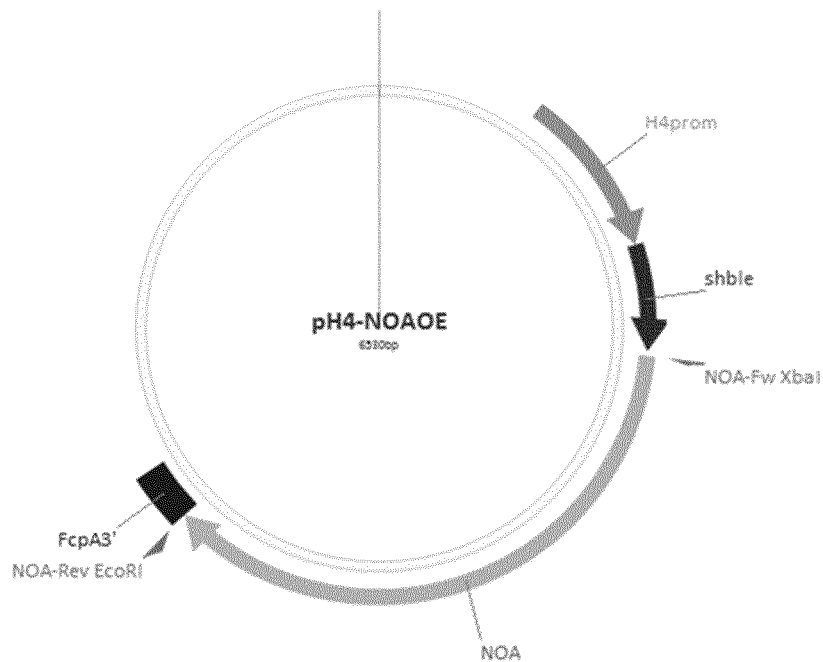

B

SEQ ID NO:6 (underlined sequence corresponding to SEQ ID NO: 1)

CTAAATTGTAAGCGTTAATATTTTGTTAAAATTCGCGTTAAATTTTTGTTAAATCAGCT
CATTTTTTAACCAATAGGCCGAAATCGGCAAAATCCCTTATAAATCAAAAGAATAGACC
GAGATAGGGTTGAGTGTTGTTCCAGTTTGGAACAAGAGTCCACTATTAAAGAACGTGGA
CTCCAACGTCAAAGGGCGAAAAACCGTCTATCAGGGCGATGGCCCACTACGTGAACCAT
CACCCTAATCAAGTTTTTTGGGGTCGAGGTGCCGTAAAGCACTAAATCGGAACCCTAAA
GGGAGCCCCCGATTTAGAGCTTGACGGGGAAAGCCGGCGAACGTGGCGAGAAAGGAAGG
GAAGAAAGCGAAAGGAGCGGGCGCTAGGGCGCTGGCAAGTGTAGCGGTCACGCTGCGCG
TAACCACCACACCCGCCGCGCTTAATGCGCCGCTACAGGGCGCGTCCCATTCGCCATTC
AGGCTGCGCAACTGTTGGGAAGGGCGATCGGTGCGGGCCTCTTCGCTATTACGCCAGCT
GGCGAAAGGGGGATGTGCTGCAAGGCGATTAAGTTGGGTAACGCCAGGGTTTTCCCAGT
CACGACGTTGTAAAACGACGGCCAGTGAGCGCGCGTAATACGACTCACTATAGGGCGAA
TTGGAGCTCGCAATCTCACGCACCAGGCGCTGGAAGGGCAACTTGCGGATGAGAAGGTC
CGTGGACTTCTGGTAACGACGGATCTCACGCAGAGCGACGGTTCCAGGGCGATAACGGT
GGGGCTTCTTGACTCCTCCGGTAGCCGGAGCGGACTTGCGGGCAGCCTTGGTGGCAAGC
TGCTTGCGCGGCGCTTTGCCTCCGGTGGATTTACGGGCGGTTTGCTTGGTTCGGGCCAT
TTTGACGGTTTTTTTTACAAGAGAAGAGTTCTTGAAATTTGTGAGGTTAAAGTGTGTGG

FIG. 2B (cont.)

CTTCCGCCGTAGTCAAGGAGCGTGCGGTTGCCGATCGCACCGGTACGTTCTGTAGAAAT
GAACACAGTGTGTTGAATTGAAAGTATGGCGCAGGTATGGTGTGTGATAAGTAGCAGCC
GCGCCGAGACAAACAAACTTTGGTTTCTACGACAATCTCTGTAGACAAGTACTAGAAAC
CCGTTTGAACGAGCATAAATCTGCACCGGCAGGCCACCAGACATCGTTTCAACGTAATA
TTCTACGTAACCATTTTATCCCAGGAAACCTACGGCCTGTGAACCACCGAGACGGAGCA
CTCACAATTCGCTCTCGGCAACAACCGACAATCGTCTTACTCACAGTCAATACCGAAAA
CAAACAACAGCCATGGCCAAGTTGACCAGTGCCGTTCCGGTGCTCACCGCGCGCGACGT
CGCCGGAGCGGTCGAGTTCTGGACCGACCGGCTCGGGTTCTCCCGGGACTTCGTGGAGG
ACGACTTCGCCGGTGTGGTCCGGGACGACGTGACCCTGTTCATCAGCGCGGTCCAGGAC
CAGGTGGTGCCGGACAACACCCTGGCCTGGGTGTGGGTGCGCGGCCTGGACGAGCTGTA
CGCCGAGTGGTCGGAGGTCGTGTCCACGAACTTCCGGGACGCCTCCGGGCCGGCCATGA
CCGAGATCGGCGAGCAGCCGTGGGGGCGGGAGTTCGCCCTGCGCGACCCGGCCGGCAAC
TGCGTGCACTTCGTGGCCGAGGAGCAGGACTGACCGACGCCGACCAACACCGCCGGTCC
GACGGCGGCCCACGGGTCCCAGGCCTTCTAGA*ATGGTCCCCACTGGTTGTATG*AGATCA
AAGAACAAACAGAGTACTGCTGCTGACGGAAGAAGGTCGATTGGAAGTCGATCCAACGC
TGGACTGGTCATGTTCTTTAGTATGACTATCTTATCGACACGACGATTTGCGGCAGCTT
GGGTTTTTCAGAGTAGTGGAATACAACGATCAATACCATCCACGCATAGGATGCGAACG
AATTTTGCTTTGTCGACGCGCTGCTTTGCTTCTTCATCCGACAACCATGACGAAGAGGA
ACAACGAGACTCTCCGAAACAAAGATCCAAACGCAGCCAAACTAATCGGTCCAAGAAAT
TCAAAATTGCTGAATCAATCGACCAGAGCAAAATAGATAAGCTAGCACAAGCATTCGAT
GAACTCGCTCGGAAGGAAGGCTTCGACTCGTCAACAGCACGCTTTGCCGACGATGTGAC
GTTCGAGGACAAGTTTGACGACGATTCGTTTCTGGACGATGACGATGATAACAACAAAG
ATAAAGTGGGAAACTTGCACCTAGATGCATCCATGTTCAGTTTAAGTGACTTTATAGAT
AAGAGTGAGGAAGATGGCGGCAATCCAACCGATCAAGATGACGAGGACTACCTTGATTT
TGGTGCAGACATTGACATGAGTATAGAAGCAAGGATTGCCGCTGCCAAACGGGATATGG
ATCTCGGTCGAGTCAGCGCCCCTCCCGATATGAGATCCTCGCGCAGGGAGGTAACTGCA
GCCGACCTTCGCAAACTTGGATTTCGAACCGAGGCAAACCCATTCGGCAACGACGAAAC
TCCACGGAAGGAGCGCTTCCAGTTGGTAACAAACTCCATGTCGTGCTCCGCCTGTGGAT
CGGACTTTCAATGCCACAACGAAGATCGGCCCGGATATCTGCCTCCTGAAAAGTTCGCT
ACGCAAACAGCACTTGGAAAAATAGAACAGATGCAAAAGTTGCAGGATAAAGCAGAAAA
AGCGGAATGGACACCTGAAGATGAGATTGAATGGTTGATTCAGACTCAGGGCAAAAAGG
ATCCGAACAAAGAAATGCAGGAGGTGCCCCAGATCGATGTTGATTCTTTGGCAGGGGAA
ATGGGCCTTGACCTCGTAGAGCTTTCCAAAAAGATGGTTATTTGCAAGCGCTGTCACGG
TCTGCAAAACTTTGGAAAAGTGCAAGATTCCCTCCGACCTGGGTGGACGAAGGAGCCAC
TGTTGTCGCAGGAGAAATTTCGTGAATTGTTAAGGCCAATCAAGGAAAAGCCGGCAGTT
ATCGTTGCATTGGTCGATCTTTTTGATTTTCGGGGTCTGTGCTCCCTGAGCTTGATGA
AATCGCTGGTGAAAACCCTGTAATTCTTGCGGCCAACAAGGCGGATCTTCTTCCAAGTG
AAATGGGACGCGTGCGAGCTGAGAGTTGGGTTCGACGCGAGCTCGAATACCTTGGAGTC
AAGTCGTTGGCCGGTATGAGAGGAGCAGTTCGGCTTGTCAGCTGCAAGACTGGAGCTGG

FIG. 2B (cont.)

GATTAATGATTTGCTGGAGAAAGCAAGAGGATTAGCCGAGGAAATCGACGGCGACATAT
ACGTCGTCGGGGCTGCAAATGCAGGAAAAAGTACGCTTTTGAATTTTGTTCTAGGTCAG
GACAAGGTGAACAGATCACCCGGAAAAGCACGAGCAGGCAACAGGAATGCCTTCAAGGG
CGCGGTGACGACAAGTCCACTGCCAGGCACAACGCTTAAGTTCATCAAAGTCGATTTAG
GCGGCGGTCGAAGTCTATATGACACTCCTGGTCTTCTGGTATTAGGCACTGTGACACAG
TTACTGACCCCGAAGAGCTGAAGATAGTTGTTCCCAAAAA*GTATGTCAAACCGATCAA*
*ACTGATATTCGATTCACAGTCAATAATGTTCAAACTAACACCTCGTTCCTCAAACAG*GC
CAATTGAACCTGTCACCCTCCGGCTCTCTACCGGAAAGTGCGTTCTAGTTGGAGGATTG
GCCCGCATCGAGTTAATCGGCGACTCAAGACCCTTTATGTTCACATTTTTGTTGCTAA
TGAGATCAAGCTCCACCCTACTGACATAGAGAGAGCCGATGAGTTCGTTCTAAAGCACG
CTGGTGGCATGTTGACTCCACCGCTAGCACCCGGACCAAAACGTATGGAAGAGATTGGA
GAATTTGAAGATCACATCGTGGATATCCAGGGTGCTGGCTGGAAAGAAGCTGCTGCTGA
TATCAGTCTTACCGGACTAGGATGGGTGGCCGTTACAGGAGCAGGGACAGCGCAAGTAA
AAATAAGTGTTCCGAAAGGTATTGGTGTATCGGTGCGGCCTCCGCTTATGCCTTTCGAT
ATCTGGAAAGTTGCATCGAAGTATACCGGAAGTCGAGCTGTAAGAAAGTCATCCAAACT
GGCGAATGGGAAAC*GAAGAAAGGTGTAGGGCGTAATTAG*GAATTCTCGAGCTACCTCG
ACTTTGGCTGGGACACTTTCAGTGAGGACAAGAAGCTTCAGAAGCGTGCTATCGAACTC
AACCAGGGACGTGCGGCACAAATGGGCATCCTTGCTCTCATGGTGCACGAACAGTTGGG
AGTCTCTATCCTTCCTTAAAAATTTAATTTTCATTAGTTGCAGTCACTCCGCTTTGGTT
TCACAGTCAGGAATAACACTAGCTCGTCTTCAggtaccCAGCTTTTGTTCCCTTTAGTG
AGGGTTAATTGCGCGCTTGGCGTAATCATGGTCATAGCTGTTTCCTGTGTGAATTGTT
ATCCGCTCACAATTCCACACAACATACGAGCCGGAAGCATAAAGTGTAAAGCCTGGGGT
GCCTAATGAGTGAGCTAACTCACATTAATTGCGTTGCGCTCACTGCCCGCTTTCCAGTC
GGGAAACCTGTCGTGCCAGCTGCATTAATGAATCGGCCAACGCGCGGGGAGAGGCGGTT
TGCGTATTGGGCGCTCTTCCGCTTCCTCGCTCACTGACTCGCTGCGCTCGGTCGTTCGG
CTGCGGCGAGCGGTATCAGCTCACTCAAAGGCGGTAATACGGTTATCCACAGAATCAGG
GGATAACGCAGGAAAGAACATGTGAGCAAAAGGCCAGCAAAAGGCCAGGAACCGTAAAA
AGGCCGCGTTGCTGGCGTTTTTCCATAGGCTCCGCCCCCCTGACGAGCATCACAAAAAT
CGACGCTCAAGTCAGAGGTGGCGAAACCCGACAGGACTATAAAGATACCAGGCGTTTCC
CCCTGGAAGCTCCCTCGTGCGCTCTCCTGTTCCGACCCTGCCGCTTACCGGATACCTGT
CCGCCTTTCTCCCTTCGGGAAGCGTGGCGCTTTCTCATAGCTCACGCTGTAGGTATCTC
AGTTCGGTGTAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAAGACACGACT
TATCGCCACTGGCAGCAGCCACTGGTAACAGGATTAGCAGAGCGAGGTATGTAGGCGGT
GCTACAGAGTTCTTGAAGTGGTGGCCTAACTACGGCTACACTAGAAGGACAGTATTTGG
TATCTGCGCTCTGCTGAAGCCAGTTACCTTCGGAAAAAGAGTTGGTAGCTCTTGATCCG
GCAAACAAACCACCGCTGGTAGCGGTGGTTTTTTTGTTTGCAAGCAGCAGATTACGCGC
AGAAAAAAAGGATCTCAAGAAGATCCTTTGATCTTTTCTACGGGGTCTGACGCTCAGTG
GAACGAAAACTCACGTTAAGGGATTTTGGTCATGAGATTATCAAAAAGGATCTTCACCT

FIG. 2B (cont.)

AGATCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCTATT
TCGTTCATCCATAGTTGCCTGACTCCCCGTCGTGTAGATAACTACGATACGGGAGGGCT
TACCATCTGGCCCCAGTGCTGCAATGATACCGCGAGACCCACGCTCACCGGCTCCAGAT
TTATCAGCAATAAACCAGCCAGCCGGAAGGGCCGAGCGCAGAAGTGGTCCTGCAACTTT
ATCCGCCTCCATCCAGTCTATTAATTGTTGCCGGGAAGCTAGAGTAAGTAGTTCGCCAG
TTAATAGTTTGCGCAACGTTGTTGCCATTGCTACAGGCATCGTGGTGTCACGCTCGTCG
TTTGGTATGGCTTCATTCAGCTCCGGTTCCCAACGATCAAGGCGAGTTACATGATCCCC
CATGTTGTGCAAAAAAGCGGTTAGCTCCTTCGGTCCTCCGATCGTTGTCAGAAGTAAGT
TGGCCGCAGTGTTATCACTCATGGTTATGGCAGCACTGCATAATTCTCTTACTGTCATG
CCATCCGTAAGATGCTTTTCTGTGACTGGTGAGTACTCAACCAAGTCATTCTGAGAATA
GTGTATGCGGCGACCGAGTTGCTCTTGCCCGGCGTCAATACGGGATAATACCGCGCCAC
ATAGCAGAACTTTAAAAGTGCTCATCATTGGAAAACGTTCTTCGGGGCGAAAACTCTCA
AGGATCTTACCGCTGTTGAGATCCAGTTCGATGTAACCCACTCGTGCACCCAACTGATC
TTCAGCATCTTTTACTTTCACCAGCGTTTCTGGGTGAGCAAAAACAGGAAGGCAAAATG
CCGCAAAAAAGGGAATAAGGGCGACACGGAAATGTTGAATACTCATACTCTTCCTTTTT
CAATATTATTGAAGCATTTATCAGGGTTATTGTCTCATGAGCGGATACATATTTGAATG
TATTTAGAAAAATAAACAAATAGGGGTTCCGCGCACATTTCCCCGAAAAGTGCCAC

SEQ ID NO:7

GTGGCACTTTTCGGGGAAATGTGCGCGGAACCCCTATTTGTTTATTTTTCTAAATACAT
TCAAATATGTATCCGCTCATGAGACAATAACCCTGATAAATGCTTCAATAATATTGAAA
AAGGAAGAGTATGAGTATTCAACATTTCCGTGTCGCCCTTATTCCCTTTTTTGCGGCAT
TTTGCCTTCCTGTTTTTGCTCACCCAGAAACGCTGGTGAAAGTAAAAGATGCTGAAGAT
CAGTTGGGTGCACGAGTGGGTTACATCGAACTGGATCTCAACAGCGGTAAGATCCTTGA
GAGTTTTCGCCCCGAAGAACGTTTTCCAATGATGAGCACTTTTAAAGTTCTGCTATGTG
GCGCGGTATTATCCCGTATTGACGCCGGGCAAGAGCAACTCGGTCGCCGCATACACTAT
TCTCAGAATGACTTGGTTGAGTACTCACCAGTCACAGAAAAGCATCTTACGGATGGCAT
GACAGTAAGAGAATTATGCAGTGCTGCCATAACCATGAGTGATAACACTGCGGCCAACT
TACTTCTGACAACGATCGGAGGACCGAAGGAGCTAACCGCTTTTTTGCACAACATGGGG
GATCATGTAACTCGCCTTGATCGTTGGGAACCGGAGCTGAATGAAGCCATACCAAACGA
CGAGCGTGACACCACGATGCCTGTAGCAATGGCAACAACGTTGCGCAAACTATTAACTG
GCGAACTACTTACTCTAGCTTCCCGGCAACAATTAATAGACTGGATGGAGGCGGATAAA
GTTGCAGGACCACTTCTGCGCTCGGCCCTTCCGGCTGGCTGGTTTATTGCTGATAAATC
TGGAGCCGGTGAGCGTGGGTCTCGCGGTATCATTGCAGCACTGGGGCCAGATGGTAAGC
CCTCCCGTATCGTAGTTATCTACACGACGGGGAGTCAGGCAACTATGGATGAACGAAAT
AGACAGATCGCTGAGATAGGTGCCTCACTGATTAAGCATTGGTAACTGTCAGACCAAGT
TTACTCATATATACTTTAGATTGATTTAAAACTTCATTTTTAATTTAAAAGGATCTAGG
TGAAGATCCTTTTTGATAATCTCATGACCAAAATCCCTTAACGTGAGTTTTCGTTCCAC
TGAGCGTCAGACCCCGTAGAAAAGATCAAAGGATCTTCTTGAGATCCTTTTTTTCTGCG
CGTAATCTGCTGCTTGCAAACAAAAAAACCACCGCTACCAGCGGTGGTTTGTTTGCCGG
ATCAAGAGCTACCAACTCTTTTTCCGAAGGTAACTGGCTTCAGCAGAGCGCAGATACCA
AATACTGTCCTTCTAGTGTAGCCGTAGTTAGGCCACCACTTCAAGAACTCTGTAGCACC
GCCTACATACCTCGCTCTGCTAATCCTGTTACCAGTGGCTGCTGCCAGTGGCGATAAGT
CGTGTCTTACCGGGTTGGACTCAAGACGATAGTTACCGGATAAGGCGCAGCGGTCGGGC
TGAACGGGGGGTTCGTGCACACAGCCCAGCTTGGAGCGAACGACCTACACCGAACTGAG
ATACCTACAGCGTGAGCTATGAGAAAGCGCCACGCTTCCCGAAGGGAGAAAGGCGGACA
GGTATCCGGTAAGCGGCAGGGTCGGAACAGGAGAGCGCACGAGGGAGCTTCCAGGGGGA
AACGCCTGGTATCTTTATAGTCCTGTCGGGTTTCGCCACCTCTGACTTGAGCGTCGATT
TTTGTGATGCTCGTCAGGGGGCGGAGCCTATGGAAAAACGCCAGCAACGCGGCCTTTT
TACGGTTCCTGGCCTTTTGCTGGCCTTTTGCTCACATGTTCTTTCCTGCGTTATCCCCT
GATTCTGTGGATAACCGTATTACCGCCTTTGAGTGAGCTGATACCGCTCGCCGCAGCCG
AACGACCGAGCGCAGCGAGTCAGTGAGCGAGGAAGCGGAAGAGCGCCCAATACGCAAAC
CGCCTCTCCCCGCGCGTTGGCCGATTCATTAATGCAGCTGGCACGACAGGTTTCCCGAC
TGGAAAGCGGGCAGTGAGCGCAACGCAATTAATGTGAGTTAGCTCACTCATTAGGCACC
CCAGGCTTTACACTTTATGCTTCCGGCTCGTATGTTGTGTGGAATTGTGAGCGGATAAC
AATTTCACACAGGAAACAGCTATGACCATGATTACGCCAAGCGCGCAATTAACCCTCAC

FIG. 8 (cont.)

```
TAAAGGGAACAAAAGCTGGAGCTCAGCTGCTGCCCCGACCGTATCTCCAAGTCAGACAT
GAAATCTTCAGTTGCGTTAAAAACTCTACGATGCTACCAGCGTTAAATAACCTTGCCCA
CGCCTTTAAACGTACCCGATCATTAACATATCGACTGGCTGCCTTGGCTTTGCACCAGC
CATCATCAGACTTAACGATGGGTATGTTGCTTGCCTTTCCTGCTTGAAGGGGGTCCGAC
TCTCTGCTTTCTCGATCGCGGGTGTGACCTCTGAATTGGAATGTAAAAATGTAAGAAGC
GACGTGTCCGGTAAAGAAATGCCCAAGCTCCATCAAATCTGCGTTGTCGGCGACCAAAC
CATGCTGGCTCGTCGACCTGCCCCGGATGCAGGAGCATGGCACTCGGCGGCATGGCACT
TGAGCCTCGCGGGAGGAATGTGTGTGGTTGGGCGCAGGCTGTGGACGGCCCCCCTCCAG
CGAAGCGGTCGCCTCCCTTTCCGACGCTTTGTGCACGTTGTCTGGTGTCCTCTGTCTCA
CGCACCTCTTCACCGACGTGGTGTCCCTCTTGTTGCTGGTGAGGGACTTGGAATGTGGT
CCTGGTTCTATCCTGGGCGCGTGTGTTCCTTTTTTTCTCTACCGTTATTCTCTCCATTT
CTGATGTCTCACCACCATCTCCCTCACCCTCCAACCGCGTCGTTGTGCCAAAATCATAC
AGCAGGATCGATGGCCAAGTTGACCAGTGCCGTTCCGGTGCTCACCGCGCGCGACGTCG
CCGGAGCGGTCGAGTTCTGGACCGACCGGCTCGGGTTCTCCCGGGACTTCGTGGAGGAC
GACTTCGCCGGTGTGGTCCGGGACGACGTGACCCTGTTCATCAGCGCGGTCCAGGACCA
GGTGGTGCCGGACAACACCCTGGCCTGGGTGTGGGTGCGCGGCCTGGACGAGCTGTACG
CCGAGTGGTCGGAGGTCGTGTCCACGAACTTCCGGGACGCCTCCGGGCCGGCCATGACC
GAGATCGGCGAGCAGCCGTGGGGCGGGAGTTCGCCCTGCGCGACCCGGCCGGCAACTG
CGTGCACTTCGTGGCCGAGGAGCAGGACTAAATCGATCTTCCTTAAAAATTTAATTTTC
ATTAGTTGCAGTCACTCCGCTTTGGTTTCACAGTCAGGAATAACACTAGCTCGTCTTCA
CCATGGATGCCAATCTCGCCTATTCATGGTGTATAAAAGTTCAACATCCAAAGCTAGAA
CTTTTGGAAAGAGAAAGAATATCCGAATAGGGCACGGCGTGCCGTATTGTTGGAGTGGA
CTAGCAGAAAGTGAGGAAGGCACAGGATGAGTTTTCTCGAGAGCTGCTGCCCCGACCGT
ATCTCCAAGTCAGACATGAAATCTTCAGTTGCGTTAAAAACTCTACGATGCTACCAGCG
TTAAATAACCTTGCCCACGCCTTTAAACGTACCCGATCATTAACATATCGACTGGCTGC
CTTGGCTTTGCACCAGCCATCATCAGACTTAACGATGGGTATGTTGCTTGCCTTTCCTG
CTTGAAGGGGGTCCGACTCTCTGCTTTCTCGATCGCGGGTGTGACCTCTGAATTGGAAT
GTAAAAATGTAAGAAGCGACGTGTCCGGTAAAGAAATGCCCAAGCTCCATCAAATCTGC
GTTGTCGGCGACCAAACCATGCTGGCTCGTCGACCTGCCCCGGATGCAGGAGCATGGCA
CTCGGCGGCATGGCACTTGAGCCTCGCGGGAGGAATGTGTGTGGTTGGGCGCAGGCTGT
GGACGGCCCCCCTCCAGCGAAGCGGTCGCCTCCCTTTCCGACGCTTTGTGCACGTTGTC
TGGTGTCCTCTGTCTCACGCACCTCTTCACCGACGTGGTGTCCCTCTTGTTGCTGGTGA
GGGACTTGGAATGTGGTCCTGGTTCTATCCTGGGCGCGTGTGTTCCTTTTTTTCTCTAC
CGTTATTCTCTCCATTTCTGATGTCTCACCACCATCTCCCTCACCCTCCAACCGCGTCG
TTGTGCCAAAATCATACAGCAGGAGGCCTGTCGACGGCGCGCCGGATCCAGATCTGAAT
TCGATATCACGCGTCCATGGCATATGGCTAGCGCGGCCGCCTCGAGTCTAGACTTCCTT
AAAAATTTAATTTTCATTAGTTGCAGTCACTCCGCTTTGGTTTCACAGTCAGGAATAAC
ACTAGCTCGTCTTCACCATGGATGCCAATCTCGCCTATTCATGGTGTATAAAAGTTCAA
CATCCAAAGCTAGAACTTTTGGAAAGAGAAAGAATATCCGAATAGGGCACGGCGTGCCG
```

FIG. 8 (cont.)

```
TATTGTTGGAGTGGACTAGCAGAAAGTGAGGAAGGCACAGGATGAGTTTTCTCGAGGGT
ACCCAATTCGCCCTATAGTGAGTCGTATTACGCGCGCTCACTGGCCGTCGTTTTACAAC
GTCGTGACTGGGAAAACCCTGGCGTTACCCAACTTAATCGCCTTGCAGCACATCCCCCT
TTCGCCAGCTGGCGTAATAGCGAAGAGGCCCGCACCGATCGCCCTTCCCAACAGTTGCG
CAGCCTGAATGGCGAATGGGACGCGCCCTGTAGCGGCGCATTAAGCGCGGCGGGTGTGG
TGGTTACGCGCAGCGTGACCGCTACACTTGCCAGCGCCCTAGCGCCCGCTCCTTTCGCT
TTCTTCCCTTCCTTTCTCGCCACGTTCGCCGGCTTTCCCCGTCAAGCTCTAAATCGGGG
GCTCCCTTTAGGGTTCCGATTTAGTGCTTTACGGCACCTCGACCCCAAAAAACTTGATT
AGGGTGATGGTTCACGTAGTGGGCCATCGCCCTGATAGACGGTTTTTCGCCCTTTGACG
TTGGAGTCCACGTTCTTTAATAGTGGACTCTTGTTCCAAACTGGAACAACACTCAACCC
TATCTCGGTCTATTCTTTTGATTTATAAGGGATTTTGCCGATTTCGGCCTATTGGTTAA
AAAATGAGCTGATTTAACAAAAATTTAACGCGAATTTTAACAAAATATTAACGCTTACA
ATTTAG
```

INCREASED TRIACYLGLYCEROL PRODUCTION IN MICROALGAE

CROSS-REFERENCE TO RELATED APPLICATIONS

This application is a § 371 national phase of International Application No. PCT/EP2017/051823, filed on Jan. 27, 2017, which claims the benefit of European Patent Application No. 16153390.6, filed on Jan. 29, 2016, which applications are incorporated by reference herein.

TECHNICAL FIELD

The application generally relates to bioproduction of molecules of interest in micro-organisms particularly in microalgae. In particular, the application relates to methods for increasing triacylglycerol production in micro-organisms, in particular in microalgae.

BACKGROUND

Microalgae have the ability to accumulate significant amounts of lipids, primarily in the form of triacylglycerol (TAG), especially under stress conditions like nutrient limitation, temperature, pH, or light stress. Nitrogen deprivation is considered a critical factor affecting lipid metabolism in microalgae. Nitrogen deprivation limits amino acid production and decreases protein synthesis, thereby impairing growth and photosynthesis, which leads to an accumulation of lipids, in particular TAG, which are used as carbon and energy provisions.

The ability of microalgae such as *Phaeodactylum tricornutum* to accumulate TAG has triggered their exploitation as host for fatty acid production, e.g. for biofuel production, for chemical applications or in food industry. *P. tricornutum* for instance is currently used for the industrial production of omega-3 polyunsaturated fatty acids.

Approaches to enhance TAG accumulation can rely on nutrient starvation such as nitrogen starvation, in particular the reduction of nitrate ($NO3^-$) availability in the medium. Disrupting the assimilation pathway of $NO3^-$ by genetic engineering has therefore been considered as a way to trigger TAG accumulation, and reducing the expression of a nitrate reductase from *P. tricornutum* has been shown to promote TAG accumulation per cell (Levitan et al. 2015 Proc Natl Acad Sci USA 112:412-417, US 2012/0282676). Other attempts to promote TAG accumulation include the stimulation of fatty acid and TAG biosynthesis, the blocking of pathways that divert carbon to alternative metabolic routes and eventually the arrest of TAG catabolism through genetic engineering of the microalgae (Maréchal 2015 In Techniques de l'Ingénieur. In 186: 1-19 and US 2014/0256927). Various strategies can also be combined.

The implementation of microalgae in industrial processes is currently based on a two-step process: first, the biomass grows using the nutrients provided in the culture medium and second, growth is slowed down or stopped by nutrient starvation, e.g. nitrogen starvation. In the above second step, TAG accumulation occurs, whereas there is virtually no TAG accumulation during the first cell growth step.

There is a need for alternative methods for enhancing triacylglycerol accumulation in microalgae, preferably without compromising cell growth and biomass yield so as to improve overall lipid productivity. In other words, it would be advantageous to implement a method in which TAG can accumulate during a cell growth step.

SUMMARY OF THE INVENTION

The present invention is based, at least in part, on the discovery that exposure of microalgae to nitric oxide (NO) increases the production of certain molecules of interest; in particular, it was discovered that exposure of microalgae to nitric oxide (NO) triggers TAG accumulation. More particularly, the present inventors have found that microalgae that are genetically engineered to induce or increase NO production, in particular by (over)expression of a gene encoding a protein involved in nitric oxide synthesis accumulate significantly more TAG compared to microalgae wherein NO production has not been modulated. In addition, it was found that cell concentration was not substantially impacted by modulation of NO production in the genetically engineered strains, such that production of the molecules of interest, in particular TAG, can occur during the growth phase of the microalgae, which can improve overall productivity of the molecules of interest, in particular TAG.

The present invention is in particular captured by any one or any combination of one or more of the below numbered aspects and embodiments (i) to (xvi) wherein:

(i) A method for increasing the production of molecules of interest in a micro-organism, said method comprising:

culturing a recombinant micro-organism which has been genetically engineered to produce or overproduce nitric oxide (NO) under conditions suitable for the production or overproduction of NO by said micro-organism.

(ii) The method according to (i), wherein the molecules of interest are molecules of the lipid metabolic pathway or biomolecules derived from said molecules, and wherein said lipid metabolic pathway is a pathway comprised between acetyl-CoA and lipids.

(iii) The method according to (i) or (ii), wherein said micro-organism is a microalga.

(iv) The method according to any one of (i) to (iii), wherein said micro-organism has been transformed with a recombinant nucleic acid encoding a protein involved in an NO production pathway or wherein expression of an endogenous gene encoding a protein involved in an NO production pathway is modified.

(v) The method according to (iv), wherein said protein is the *Phaeodactylum tricornutum* NOA (PtNOA) protein or a variant thereof.

(vi) The method according to (iv), wherein said protein is the *Nannochloropsis gaditana* NOA (NgNOA) protein or a variant thereof.

(vii) The method according (iv), wherein said protein is a nitric oxide synthase (NOS).

(viii) The method according to any one of (iii) to (vi), wherein the microalga is selected from the *Chromalveolata*.

(ix) The method according (viii), wherein the microalga is selected from the Bacillariophyceae or the Eustigmatophyceae.

(x) The method according to (ix), wherein the microalga is *Phaeodactylum tricornutum*.

(xi) The method according to any one of (i) to (x), wherein the molecules of interest are triacylglycerols (TAGs).

(xii) The method according to (xi), wherein the triacylglycerol content is increased in said recombinant micro-organism to at least 150%, preferably at least 200%, compared to a corresponding micro-organism wherein the NO production pathway was not modulated.

(xiii) The method according to any one of (i) to (xii), wherein said culturing conditions are suitable for growth of the recombinant micro-organism, such that production of the molecules of interest is concomitant with the growth of the recombinant micro-organism.

(xiv) Use of a recombinant micro-organism which has been genetically engineered to produce or overproduce nitric oxide (NO) for the production of molecules of interest.

(xv) Use according to (xiv), wherein the molecules of interest are molecules of the lipid metabolic pathway or biomolecules derived from said molecules, and wherein said lipid metabolic pathway is a pathway comprised between acetyl-CoA and lipids.

(xvi) Use according to (xv) for the production of triacylglycerols, fatty acids, hydrocarbons or fatty alcohols.

(xvii) Use according to any one of (xiv) or (xvi) for biofuel production, in food industry, in pharmaceutical industry or for the production of cosmetics.

(xviii) A recombinant microalga, which has been transformed with a recombinant nucleic acid encoding a PtNOA homolog.

(xix) The recombinant micro-organism according to (xviii), wherein said PtNOA homolog is from *Nannochloropsis gaditana* having SEQ ID NO:4.

BRIEF DESCRIPTION OF THE FIGURES

The teaching of the application is illustrated by the following Figures which are to be considered as illustrative only and do not in any way limit the scope of the claims.

FIG. 1: (A) Sequence alignment of PtNOA (SEQ ID NO:2) and NgNOA (SEQ ID NO:4). (B) Nucleotide sequence coding for NgNOA (SEQ ID NO:3).

FIG. 2: Vector map (A) and vector sequence (B, SEQ ID NO:6) of the pH4-GUS vector containing the NOA gene of *P. tricornutum* (pH4-NOAOE). (A) The PtNOA gene was cloned under the control of the constitutive histone 4 promoter (H4prom). The vector further contained a gene coding for resistance to zeocin (shble), allowing selection of transformed cells. (B) The ATG and TAG of the PtNOA gene are underlined. The coding sequence of PtNOA is underlined (SEQ ID NO:1). The XbaI and EcoRI sites used for cloning are in bold. The intron is in italics.

FIG. 8: SEQ ID NO:7

DETAILED DESCRIPTION OF THE INVENTION

Figure 3:
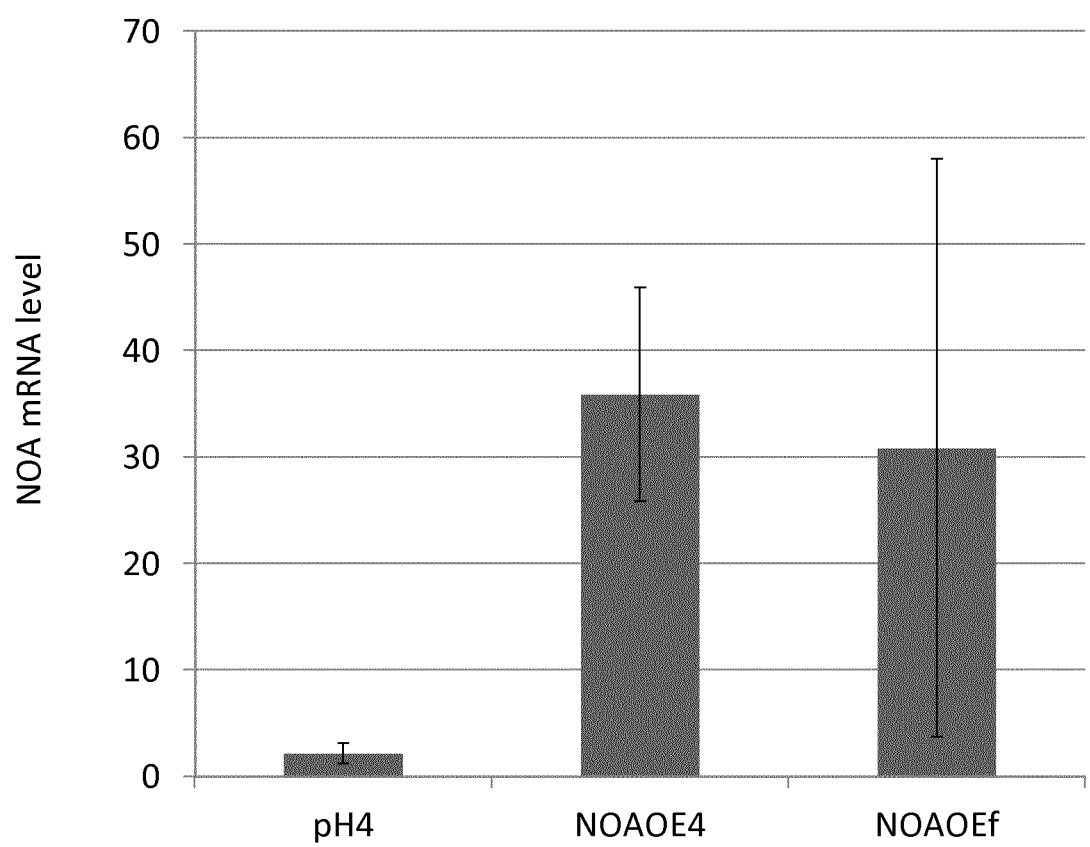
FIG. 3: Exemplary NOA overexpressing *P. tricornutum* strains. Two independent PtNOA overexpressing strains of *P. tricornutum* are shown: NOAE4 and NOAEf. pH4 is a control *P. tricornutum* strain that was transformed with an empty vector. NOA expression level was measured in three biological replicates, and normalized using the housekeeping genes 30S Ribosomal Protein Subunit (RPS) and tubulin (TUB).

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. Where reference is made to embodiments as comprising certain elements or steps, this encompasses also embodiments which consist essentially of the recited elements or steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety.

As used herein, the terms "microbial", "microbial organism" or "micro-organism" are intended to mean any organism that exists as a microscopic cell that is included within the domains of archaea, bacteria or eukaryotes. Therefore, the term is intended to encompass prokaryotic or eukaryotic cells or organisms having a microscopic size and includes bacteria, archaea and eubacteria such as cyanobacteria of all species as well as eukaryotic micro-organisms such as fungi, including yeasts, and algae. The term also includes cell cultures of any species.

The term "microalga" or "microalgae" (plural) as used herein refers to microscopic alga(e). "Microalgae" encompass, without limitation, organisms within (i) several eukaryotic phyla, including the Rhodophyta (red algae), Chlorophyta (green algae), Dinoflagellata, Haptophyta, (ii) several classes from the eukaryotic phylum Heterokontophyta which includes, without limitation, the classes Bacillariophycea (diatoms), Eustigmatophycea, Phaeophyceae (brown algae), Xanthophyceae (yellow-green algae) and Chrysophyceae (golden algae), and (iii) the prokaryotic phylum Cyanobacteria (blue-green algae). The term "microalgae" includes for example genera selected from:

*Achnanthes, Amphora, Anabaena, Anikstrodesmis, Arachnoidiscusm, Aster, Botryococcus, Chaetoceros, Chlamydomonas, Chlorella, Chlorococcum, Chorethron, Cocconeis, Coscinodiscus, Crypthecodinium, Cyclotella, Cylindrotheca, Desmodesmus, Dunaliella, Emiliana, Euglena, Fistulifera, Fragilariopsis, Gyrosigma, Hematococcus, Isochrysis, Lampriscus, Monochrysis, Monoraphidium, Nannochloris, Nannochloropsis, Navicula, Neochloris, Nephrochloris, Nephroselmis, Nitzschia, Nodularia, Nostoc, Odontella, Oochromonas, Oocystis, Oscillartoria, Pavlova, Phaeodactylum, Playtmonas, Pleurochrysis, Porhyra, Pseudoanabaena, Pyramimonas, Scenedesmus, Schyzochitrium, Stichococcus, Synechococcus, Synechocystis, Tetraselmis, Thalassiosira,* and *Trichodesmium.*

The term "transformation" means introducing an exogenous nucleic acid into an organism so that the nucleic acid is replicable, either as an extrachromosomal element or by chromosomal integration.

The terms "genetically engineered" or "genetically modified" or "recombinant" as used herein with reference to a host cell, in particular a micro-organism such as a microalga, denote a non-naturally occurring host cell, as well as its recombinant progeny, that has at least one genetic alteration not found in a naturally occurring strain of the referenced species, including wild-type strains of the referenced species. Such genetic modification is typically achieved by technical means (i.e. non-naturally) through human intervention and may include, e.g., the introduction of an exogenous nucleic acid and/or the modification, over-expression, or deletion of an endogenous nucleic acid.

The term "exogenous" or "foreign" as used herein is intended to mean that the referenced molecule, in particular nucleic acid, is not naturally present in the host cell.

The term "endogenous" or "native" as used herein denotes that the referenced molecule, in particular nucleic acid, is present in the host cell.

By "recombinant nucleic acid" when referring to a nucleic acid in a recombinant host cell, in particular a recombinant micro-organism such as a recombinant microalga, is meant that at least part of said nucleic acid is not naturally present in the host cell in the same genomic location. For instance a recombinant nucleic acid can comprise a coding sequence naturally occurring in the host cell under control of an exogenous promotor, or it can be an additional copy of a gene naturally occurring in the host cell, or a recombinant nucleic acid can comprise an exogenous coding sequence under the control of an endogenous promoter.

By "nucleic acid" is meant oligomers and polymers of any length composed essentially of nucleotides, e.g., deoxyribonucleotides and/or ribonucleotides. Nucleic acids can comprise purine and/or pyrimidine bases and/or other natural (e.g., xanthine, inosine, hypoxanthine), chemically or biochemically modified (e.g., methylated), non-natural, or derivatised nucleotide bases. The backbone of nucleic acids can comprise sugars and phosphate groups, as can typically be found in RNA or DNA, and/or one or more modified or substituted sugars and/or one or more modified or substituted phosphate groups.

Modifications of phosphate groups or sugars may be introduced to improve stability, resistance to enzymatic degradation, or some other useful property. A "nucleic acid" can be for example double-stranded, partly double stranded, or single-stranded. Where single-stranded, the nucleic acid can be the sense strand or the antisense strand. The "nucleic acid" can be circular or linear. The term "nucleic acid" as used herein preferably encompasses DNA and RNA, specifically including genomic, hnRNA, pre-mRNA, mRNA, cDNA, recombinant or synthetic nucleic acids, including vectors.

By "encoding" is meant that a nucleic acid sequence or part(s) thereof corresponds, by virtue of the genetic code of an organism in question, to a particular amino acid sequence, e.g., the amino acid sequence of a desired polypeptide or protein. By means of example, nucleic acids "encoding" a particular polypeptide or protein, e.g. an enzyme, may encompass genomic, hnRNA, pre-mRNA, mRNA, cDNA, recombinant or synthetic nucleic acids.

Preferably, a nucleic acid encoding a particular polypeptide or protein may comprise an open reading frame (ORF) encoding said polypeptide or protein. An "open reading frame" or "ORF" refers to a succession of coding nucleotide triplets (codons) starting with a translation initiation codon and closing with a translation termination codon known per se, and not containing any internal in-frame translation termination codon, and potentially capable of encoding a polypeptide or protein. Hence, the term may be synonymous with "coding sequence" as used in the art.

The terms "polypeptide" and "protein" are used interchangeably herein and generally refer to a polymer of amino acid residues linked by peptide bonds, and are not limited to a minimum length of the product. Thus, peptides, oligopeptides, polypeptides, dimers (hetero- and homo-), multimers (hetero- and homo-), and the like, are included within the definition. Both full-length proteins and fragments thereof are encompassed by the definition. The terms also include post-expression modifications of the polypeptide, for example, glycosylation, acetylation, phosphorylation, etc. Furthermore, for purposes of the present invention, the terms also refer to such when including modifications, such as deletions, additions and substitutions (e.g., conservative in nature), to the sequence of a native protein or polypeptide.

The term "variant", when used in connection to a protein, such as an enzyme, for example as in "a variant of protein X", refers to a protein, such as an enzyme, that is altered in its sequence compared to protein X, but that retains the activity of protein X, such as the enzymatic activity (i.e. a functional variant or homolog). More particularly a functional variant of protein X involved in the production of NO, such as a NOA protein, is capable of ensuring at least 60% of the activity of protein X in the production of NO. More particularly, the effect of a homolog or functional variant on NO production activity can be determined by measuring NO levels in a micro-organism. For example, NO levels can be measured using the fluorophore 4-amino-5-methylamino-2',7'-difluororescein diacetate (DAF-FM), which allows detection of nitric oxide ($ONOO^-$) which is in equilibrium with NO (St Laurent et al. 2015 Methods Mol Biol. 1220:339-345). In particular embodiments, the functional variant is a non-natural variant. In alternative embodiments, the functional variant is a homolog. Preferably, such variant would show at least 80%, more preferably at least 85%, even more preferably at least 90%, and yet more preferably at least 95% such as at least 96%, at least 97%, at least 98% or at least 99% sequence identity to the reference protein, preferably calculated over the entire length of the sequence. The sequence changes may be naturally occurring, for example, due to the degeneracy of the genetic code, or may be introduced artificially, for example by targeted mutagenesis of the respective sequence. Such techniques are well known to the skilled person.

The term "homolog" as used herein in connection to a protein, such as an enzyme, for example as in "a homolog of protein X" refers to the fact that the protein differs from protein X in its sequence, but that retains the activity or protein X, such as the enzymatic activity as detailed above, and originates from another species, i.e. is a naturally occurring sequence. A homolog of protein X can be identified by the skilled person by pairwise search methods such as BLAST and checking of the corresponding activity.

As used herein, the terms "identity" and "identical" and the like are used interchangeably with the terms "homology" and "homologues" and the like herein and refer to the sequence similarity between two polymeric molecules, e.g., between two nucleic acid molecules or polypeptides. Methods for comparing sequences and determining sequence identity are well known in the art. By means of example, percentage of sequence identity refers to a percentage of identical nucleic acids or amino acids between two sequences after alignment of these sequences. Alignments and percentages of identity can be performed and calculated with various different programs and algorithms known in the art. Preferred alignment algorithms include BLAST (Altschul, 1990; available for instance at the NCBI website) and Clustal (reviewed in Chenna, 2003; available for instance at the EBI website). Preferably, BLAST is used to calculate the percentage of identity between two sequences, such as the "Blast 2 sequences" algorithm described by Tatusova and Madden 1999 (FEMS Microbiol Lett 174: 247-250), for example using the published default settings or other suitable settings (such as, e.g., for the BLASTN algorithm: cost to open a gap=5, cost to extend a gap=2, penalty for a mismatch=−2, reward for a match=1, gap x_dropoff=50, expectation value=10.0, word size=28; or for the BLASTP algorithm: matrix=Blosum62, cost to open a gap=11, cost to extend a gap=1, expectation value=10.0, word size=3).

As used herein, the term "molecules of interest" refers to any molecule which can be produced by micro-organisms, including but not limited to molecules derived from the acetyl-CoA pool in a micro-organism. Such molecules of interest include, without limitation, hydrocarbons, fatty acids and lipids. Such molecules of interest can be recovered from the micro-organism or its culture medium, and then used in certain applications.

As used herein, the term "lipid metabolic pathway" refers to any pathway in a micro-organism comprised between acetyl-CoA and lipids (it being understood that acetyl-CoA is included in such lipid metabolic pathway). Said term hence encompasses without limitation fatty acid synthesis pathways, pathways ensuring the assembly of triacylglycerols (TAGs) or the conversion of any lipids to TAGs, and pathways degrading TAGs (beta-oxidation).

As used herein, "triacylglycerols", also referred to as "triacylglycerides" or "TAG" are esters resulting from the esterification of the three hydroxyl groups of glycerol, with three fatty acids.

The present application generally relates to production of molecules of interest, in particular production of molecules of the lipid metabolic pathway, including production of triacylglycerol (TAG) and any intermediates in the lipid metabolic pathway, in micro-organisms, in particular in microalgae. The application is further directed to the production of biomolecules derived from said molecules of the lipid metabolic pathway.

More particularly, the application provides methods for increasing TAG production in micro-organisms, in particular microalgae, by genetically engineering the micro-organisms, in particular the microalgae, to produce or overproduce nitric oxide (NO). The application also encompasses the recombinant micro-organisms as well as their use, e.g. for fatty acid production.

It has been surprisingly found that exposure of microalgae such as *Phaeodactylum tricornutum* to nitric oxide (NO) triggers TAG accumulation in the microalgae. The present inventors have found that genetic engineering of microalgae to produce or overproduce NO, in particular by transformation with a recombinant nucleic acid encoding a protein involved in NO production (such as the NOA protein of *Phaeodactylum tricornutum*), results in increased production of certain molecules of interest; in particular, it was discovered that such engineering in the NO production pathway results in increased TAG production in said recombinant microalgae.

Accordingly, in an aspect, the application provides a method for increasing the production of molecules of interest in a micro-organism, in particular a microalga, said method comprising culturing a recombinant micro-organism, in particular a recombinant microalga, which has been genetically engineered to produce or overproduce NO under conditions suitable to produce or overproduce NO in said recombinant micro-organism. In particular embodiments, the invention thus relates to a method for the production of molecules of interest, which encompasses the steps of (i) genetically engineering a micro-organism, in particular a microalga, to produce or overproduce NO; and (ii) culturing the recombinant micro-organism, in particular the recombinant microalga, obtained in step (b) so as to allow the production of said molecules of interest.

In particular embodiments, the molecules of interest are molecules of the lipid metabolic pathway or biomolecules derived from said molecules and the production of such molecules of interest is increased according to the invention. In further particular embodiments, the molecules of interest are lipids, in particular triacylglycerols (TAGs).

In particular embodiments, the recombinant micro-organism has been engineered to express or overexpress a protein involved in an NO production pathway.

Preferably, the recombinant micro-organism has been transformed with a recombinant nucleic acid encoding a protein involved in an NO production pathway.

Accordingly, in embodiments, the method encompasses transforming the micro-organism with a recombinant nucleic acid encoding a protein involved in an NO production pathway, and culturing the recombinant micro-organism so obtained under conditions suitable to produce or overproduce NO in said recombinant micro-organism so as to allow production of the desired molecule or biomolecule by the micro-organism.

NO production differs from organism to organism. Some diatoms such as Pseudo-nitzschia multistriata contain a nitric oxide synthase (NOS) (Di Dato et al. 2015 Scientific Reports 5:12329). In the pennate diatom *Phaeodactylum tricornutum*, NO production depends on the activity of a protein called NOA (Vardi et al. 2008). Any protein or enzyme involved in NO production is envisaged herein for (over)expression in the recombinant micro-organisms described herein.

In particular embodiments, the protein involved in the NO production pathway is a NOA protein. In particular embodiments, the NOA protein is an NOA protein of microbial origin, such as from a microalga or diatom. In particular embodiments, the protein involved in NO production is the NOA protein of a *Phaeodactylum* more particularly of *P. tricornutum*, also referred to herein as PtNOA, or a variant or a homolog thereof. In particular embodiments, of the present invention, the homologue of PtNOA originates from a microalga. As used herein the term "PtNOA" refers to a protein having an amino acid sequence of SEQ ID NO:2.

Preferably, the variants have a sequence substantially identical to SEQ ID NO:2, or a sequence having at least about 70%, preferably at least about 80%, more preferably at least about 85%, 90% or 95%, even more preferably at least about 96%, 97%, 98% or 99% sequence identity to SEQ ID NO:2.

Accordingly, in embodiments of the methods described herein, the recombinant micro-organism, in particular the recombinant microalga, has been transformed with a recombinant nucleic acid encoding a NOA protein. In particular embodiments, the recombinant nucleic acid encoding a NOA protein encodes a NOA protein from a *Phaeodactylum* species or a variant or a homolog thereof. In further embodiments, the recombinant micro-organism comprises a recombinant nucleic acid encoding a *Phaeodactylum tricornutum* NOA protein or a homolog or functional variant thereof. In particular embodiments, of the present invention, the homologue of PtNOA originates from a microalga. Most particularly, the recombinant micro-organism is transformed with a recombinant nucleic acid comprising the sequence of SEQ ID NO:1 or a sequence substantially identical to SEQ ID NO:1, or a sequence having at least about 70%, preferably at least about 80%, more preferably at least about 85%, 90% or 95%, even more preferably at least about 96%, 97%, 98% or 99% sequence identity to SEQ ID NO:1.

The application also envisages the use of recombinant nucleic acids encoding homologs of the identified *Phaeodactylum tricornutum* NOA protein. For instance the present inventors have identified a genomic sequence in *Nannochloropsis gaditana* (SEQ ID NO:3) encoding a protein of SEQ ID NO:4 that is homologous to PtNOA (FIG. 1A), which protein is referred to herein as NgNOA. In particular embodiments, the recombinant nucleic acid encoding a NOA protein encodes a NOA protein from *Nannochloropsis gaditana* or a variant thereof, i.e. having an amino acid sequence of SEQ ID NO:4 (i.e. NgNOA) or a variant thereof. Indeed, also envisaged herein is the use of variants of said NgNOA, which may have a sequence substantially identical to SEQ ID NO:4 or at least about 70%, preferably at least about 80%, more preferably at least about 85%, 90% or 95%, even more preferably at least about 96%, 97%, 98% or 99% sequence identity to SEQ ID NO:4.

In particular embodiments, the recombinant nucleic acid encoding the NOA protein has been codon-optimized for expression in one or more microalgae of interest. Accordingly, in particular embodiments, the invention provides recombinant microalgae, in particular microalgae of a *Phaeodactylum* species, which have been transformed with a recombinant nucleic acid comprising SEQ ID NO:5, which sequence encodes the same protein as the sequence of SEQ ID NO:3, but wherein the coding sequence was codon-optimized for expression in a *Phaeodactylum* species.

In particular embodiments, the protein involved in the NO production pathway is a nitric oxide synthase (NOS) and the recombinant micro-organism has been transformed with a recombinant nucleic acid encoding a NOS enzyme. Non-limiting examples of NOS enzymes suitable for use in the methods and recombinant microalgae envisaged herein include the NOS of Pseudo-nitzschia multistriata (PmNOS) as described in Di Dato et al. (2015), the NOS of *Amphiprora* sp., *Thalassiosira rotula*, *Thalassiosira minuscule*, *Skeletonema menzelii*, *Skeletonema costatum*, *Skeletonema marinoi*, *Cylindrotheca closterium*, *Chaetoceros* cf. neogracile as described in Di Dato et al. (2015).

Also envisaged herein are variants or homologs of the proteins and enzymes involved in an NO production pathway as described herein. It is understood that the variant proteins or enzymes described herein may have conservative or non-essential amino acid substitutions, which do not have a substantial effect on the protein function. Whether or not a particular substitution will be tolerated (i.e., will not adversely affect desired biological properties) can be determined as described in Bowie et al. (1990) (Science 247:1306 1310). A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

Additional protein and enzyme variants are those in which additional amino acids are fused to the enzyme, such as restriction sites for cloning purposes.

The recombinant micro-organisms described herein may comprise an exogenous nucleic acid encoding a protein or an enzyme involved in an NO production pathway, and/or may over-express an endogenous nucleic acid encoding a protein or an enzyme involved in an NO production pathway.

Methods for increasing expression of an endogenous nucleic acid are known in the art and include but are not limited to introducing one or more copies of the endogenously present nucleic acid, optionally under control of stronger promoters, introducing transcription activators, capable of activating transcription of the endogenous gene etc.

The methods provided herein envisage genetically engineering micro-organisms, in particular microalgae, for producing an increased amount of certain molecules of interest. Accordingly, the herein described methods aim to increase the production of molecules of interest, in particular molecules of the lipid metabolic pathway, including lipids as well as intermediates of said lipid metabolic pathway such as fatty acids. In addition, the herein described methods may also increase the production of biomolecules derived from said molecules of the lipid metabolic pathway such as hydrocarbons, fatty alcohols, etc. In particular embodiments of the method, the production of lipids, more particularly TAGs, is increased.

In particular embodiments, the micro-organisms described herein have further been genetically modified to ensure production of molecules of interest, in particular molecules of the lipid metabolic pathway or biomolecules derived from said molecules. Further genetic modifications to further increase lipid production, in particular TAG production, as well as the production of any intermediate of the lipid metabolic pathway, are envisaged herein, but also further genetic modifications to ensure (increased) production of a biomolecule of interest derived from a molecule of the lipid metabolic pathway. For example, the recombinant micro-organisms described herein may be further genetically modified to further increase fatty acid biosynthesis and/or TAG assembly. In other examples, the recombinant micro-organisms may be further genetically modified to ensure production of e.g. hydrocarbons from fatty acids, or fatty alcohols from acetyl-CoA.

As metabolic pathways are well-established in micro-organisms, methods for modifying the lipid metabolic pathway and the production of biomolecules derived from molecules of said lipid metabolic pathway in a micro-organism as described herein can be easily determined by the skilled person, including in microalgae. Standard reference work setting forth the general principles of biochemistry includes "*Biochemical Pathways: An Atlas of Biochemistry and Molecular Biology*", ed. Michal, G, John Wiley and Sons, Inc., New York, US, 1999. In the field of microalgae, standard reference work includes: "*Handbook of Microalgal Culture: Applied Phycology and Biotechnology*", 2nd Edition, Amos Richmond and Qiang Hu, WileyBlackwell, 2013.

The methods provided herein envisage transforming micro-organisms, in particular microalgae, to stimulate the lipid metabolic pathway and/or to increase production of biomolecules derived from molecules of the lipid metabolic pathway. Accordingly, in particular embodiments, the methods encompass providing a microbial strain suitable for lipid production or wherein the lipid production is to be increased. Such a strain is preferably a microbial strain which produces lipids.

In preferred embodiments, the micro-organism is a microalga. Preferably, the microalga is selected from the *Chromalveolata*, more preferably the Heterokontophyta, even more preferably the Bacillariophyceae (diatoms), including the Naviculales such as *Phaeodactylum tricornutum* and the Pennales (pennate diatoms), and/or the Eustigmatophyceae, including *Nannochloropsis* species such as *Nannochloropsis gaditana*. In particular embodiments, the microalga is *Phaeodactylum tricornutum*, including the Pt1 strain.

In further particular embodiments, the recombinant microalga is *Phaeodactylum tricornutum* which has been modified to ensure an increased NO production. More particularly the recombinant *Phaeodactylum tricornutum* is transformed with one or more recombinant nucleic acids encoding one or more proteins involved in NO production such as one or more of PtNOA, NgNOA or a variant thereof.

Most microalgae are photoautotrophs, i.e. their growth is strictly dependent on the generation of photosynthetically-derived energy. Their cultivation hence requires a relatively controlled environment with a large input of light energy. For certain industrial applications, it is advantageous to use heterotrophic microalgae, which can be grown in conventional fermenters. In particular embodiments the microalgae have been further metabolically engineered to grow heterotrophically (i.e. to utilize exogenous organic compounds (such as glucose, acetate, etc.) as an energy or carbon source). A method for metabolically engineering microalgae to grow heterotrophically has been described in U.S. Pat. No. 7,939,710, which is specifically incorporated by reference herein. In particular embodiments, the microalgae are further genetically engineered to comprise a recombinant nucleic acid encoding a glucose transporter, preferably a glucose transporter selected from the group consisting of Glut 1 (human erythrocyte glucose transporter 1) and Hup1 (Chlorella HUP1 Monosaccharide-H+ Symporter). The glucose transporters facilitate the uptake of glucose by the host cell, allowing the cells to metabolize exogenous organic carbon and to grow independent of light. This is particularly advantageous for obligate phototrophic microalgae. Lists of phototrophs may be found in a review by Droop (1974. Heterotrophy of Carbon. In Algal Physiology and Biochemistry, Botanical Monographs, 10:530-559, ed. Stewart, University of California Press, Berkeley), and include, for example but without limitation, organisms of the phyla Cyanophyta (Blue-green algae), including the species *Spirulina* and *Anabaena;* Chlorophyta (Green algae), including the species *Dunaliella, Chlamydomonas,* and *Heamatococcus;* Rhodophyta (Red algae), including the species *Porphyridium, Porphyra, Euchema,* and *Graciliaria;* Phaeophyta (Brown algae), including the species, *Macrocystis, Laminaria, Undaria,* and *Fucus; Baccilariophyta* (Diatoms), including the species *Nitzschia, Navicula, Thalassiosira,* and *Phaeodactylum;* Dinophyta (Dinoflagellates), including the species *Gonyaulax;* Chrysophyta (Golden algae), including the species *lrsochrysis* and *Nannochloropsis;* Cryptophyla, including the species *Cryptomonas*; and Euglenophyla, including the species *Euglena*.

In the methods envisaged herein, the recombinant micro-organisms are preferably cultured under conditions suitable for the production of NO by the recombinant micro-organisms so as to increase production of the molecules of interest. More particularly this implies "conditions sufficient to allow expression" of the recombinant nucleic acid (encoding a protein involved in an NO production pathway). Typically the culture conditions are also selected so as to favor production of molecules of interest, in particular molecules of the lipid metabolic pathway or biomolecules derived from said molecules.

Culture conditions can comprise many parameters, such as temperature ranges, levels of aeration, and media composition. Each of these conditions, individually and in combination, allows the micro-organism to grow. To determine if conditions are sufficient to allow (over)expression, a micro-organism can be cultured, for example, for about 4, 8, 12, 18, 24, 36, or 48 hours. During and/or after culturing, samples can be obtained and analyzed to determine if the conditions allow (over)expression. For example, the micro-organisms in the sample or the culture medium in which the micro-organisms were grown can be tested for the presence of a desired product, e.g. NO or a transcript of the recombinant nucleic acid. When testing for the presence a desired product, assays, such as, but not limited to, polymerase chain reaction (PCR), sodium dodecyl sulfate polyacrylamide gel electrophoresis (SDS-PAGE), TLC, HPLC, GC/FID, GC/MS, LC/MS, MS, can be used. In particular, when testing for the presence of NO, the fluorophore 4-amino-5-methylamino-2',7'-difluororescein diacetate (DAF-FM) can be used as described elsewhere herein.

Exemplary culture media include broths or gels. The micro-organisms may be grown in a culture medium comprising a carbon source to be used for growth of the micro-organisms. Exemplary carbon sources include carbohydrates, such as glucose, fructose, cellulose, or the like, that can be directly metabolized by the host cell. In addition, enzymes can be added to the culture medium to facilitate the mobilization (e.g., the depolymerization of starch or cellulose to fermentable sugars) and subsequent metabolism of the carbon source. A culture medium may optionally contain further nutrients as required by the particular strain, including inorganic nitrogen or phosphorous sources, and the like, and minerals and the like. In particular embodiments, wherein phototrophic microalgae are used, the method for increasing the production of molecules of interest, in particular molecules of the lipid metabolic pathway or biomolecules derived from said molecules, may comprise providing recombinant microalgae genetically engineered to produce or overproduce NO as taught herein, and culturing said microalgae in photobioreactors or an open pond system using $CO_2$ and sunlight as feedstock.

Other growth conditions, such as temperature, cell density, and the like are generally selected to provide an economical process. Temperatures during each of the growth phase and the production phase may range from above the freezing temperature of the medium to about 50° C.

The culturing step of the methods described herein can be conducted continuously, batch-wise, or some combination thereof.

In particular embodiments, the culturing conditions which are suitable for the production of NO by the recombinant micro-organisms are also suitable for growth of the recombinant micro-organism, such that the production of the molecules of interest is concomitant with the growth of the micro-organism. In other words, according to particular embodiments, the cell concentration is not substantially impacted by modulating the NO production pathway, in particular by NOA or NOS overexpression, in the genetically engineered strains, such that the production of the molecules of interest can occur during the growth phase of the micro-organism, which can increase improve overall productivity of the molecules of interest.

In particular embodiments, the methods for the increased production of molecules of interest, further comprise the step of recovering said molecules or biomolecules from the recombinant micro-organisms and/or from the cultivation medium. Accordingly, in particular embodiments the methods comprise recovering molecules of the lipid metabolic pathway, in particular lipids, more particularly TAGs, or biomolecules derived from said molecules as envisaged herein, from the recombinant micro-organism and/or from the cultivation medium.

Methods for the recovery of said molecules or biomolecules from microalgae are known in the art and typically involve cell disruption and extraction of the molecules of interest (Guldhe et al. 2014, Fuel 128:46-52). Alternatively or in addition, the recombinant micro-organisms described herein may be further genetically engineered to ensure secretion of the molecules of interest. A further example includes a hydrothermal processing (HTL) of microalgae to produce biocrude, from which the molecules of interest can be recovered or which can be further processed to e.g. biofuel.

As noted before, the present inventors have surprisingly found that culturing the recombinant micro-organisms described herein results in increased production of molecules of interest, in particular increased production of molecules of the lipid metabolic pathway, in particular increased lipid production, more particularly increased TAG production.

In particular embodiments, the recombinant micro-organisms, in particular the recombinant microalgae described herein ensure a rate of TAG production, which is sufficiently high to be industrially valuable. More particularly, the TAG content in said recombinant micro-organisms and microalgae may be to at least 110%, preferably at least 120%, more preferably at least 150% 160%, 170%, 180% or 190%, even more preferably at least 200% or more as compared to micro-organisms and microalgae wherein the NO production was not modulated such as a wild-type micro-organisms and microalgae or micro-organisms and microalgae that have been transformed with an empty vector. In other words, the present method causes an increase in the TAG content of the recombinant micro-organisms and microalga compared to a micro-organism or microalga wherein the NO production was not modulated by a factor of at least 1.1, preferably at least 1.2, more preferably at least 1.5, 1.6, 1.7, 1.8 or 1.9, even more preferably at least 2 or even beyond.

The lipid content, in particular the TAG content, of a micro-organism can be measured using a variety of methods well known in the art. Non-limiting examples include staining with the fluorophore Nile Red (excitation wavelength at 485 nm; emission at 525 nm) and measurement of Nile Red fluorescence, and mass spectrometry (MS).

In particular embodiments, the methods include optimizing said micro-organisms and/or the cultivation medium so as to ensure the production of the biomolecule of interest. This can encompass modifying the micro-organism so as to further the production and/or preventing the catabolism of the biomolecule, for instance by blocking other biosynthesis pathways. For instance, where production of TAG is envisaged, the methods of the present invention may additionally comprise modifying the micro-organism of interest by blocking of pathways that divert carbon to alternative metabolic routes and/or preventing TAG catabolism. Such methods have been described in the art, as noted in the background section herein. Additionally or alternatively the cultivation or production conditions can be adjusted to stimulate the production of the biomolecule of interest. In particular embodiments, the micro-organisms are modified to block non-desirable pathways, such as programmed cell death. In particular embodiments, the methods of the invention comprise maintaining the cell under conditions which ensure that cell viability is maintained or is at an acceptable level.

The recombinant micro-organisms and microalgae described herein may hence be particularly suitable for industrial applications such as biofuel production and the production of biomolecules e.g. for chemical applications, for use in food industry, for the production of cosmetics, etc. Hence, a further aspect relates to the use of the recombinant micro-organisms and microalgae described herein for biofuel production or production of biomolecules (e.g. fatty acids), e.g. for chemical industry, for food industry, for cosmetics, etc.

An aspect of the application is directed to methods for obtaining a recombinant micro-organism such as a recombinant microalga capable of (over)producing NO as described herein. Such methods may comprise ensuring (over)expression of a gene encoding a protein involved in NO production. In particular embodiments, the methods comprise transforming a micro-organism with a recombinant nucleic acid encoding a protein involved in an NO production pathway as taught herein. In particular, the method may comprise the steps of: a) transforming a micro-organism with a recombinant nucleic acid encoding a protein involved in an NO production pathway as described herein above; and b) selecting a micro-organism capable of (over)producing NO. As detailed above the recombinant nucleic acid may encode a protein which is endogenous or foreign to the micro-organism. Additionally or alternatively the methods may involve modifications which induce or increase endogenous expression of a gene encoding a protein involved in NO production as described above.

The methods for generating the recombinant micro-organisms described herein involve standard genetic modifications, for which well-established methods are available to the skilled person.

More particularly, genetic engineering of the micro-organisms containing a recombinant nucleic acid encoding a protein involved in an NO production pathway as described herein may be accomplished in one or more steps via the design and construction of appropriate vectors and transformation of the micro-organisms with those vectors.

Methods for transforming microalgae are well known to a skilled person. For example, electroporation and/or chemical (such as calcium chloride- or lithium acetate-based)

transformation methods or *Agrobacterium tumefaciens*-mediated transformation methods as known in the art can be used.

Numerous vectors are known to practitioners skilled in the art and any such vector may be used. Selection of an appropriate vector is a matter of choice. Preferred vectors are vectors developed for microalgae such as the vectors called pH4-GUS, pCT2, and pCT2Ng.

Typically, a vector may comprise a recombinant nucleic acid encoding a protein involved in an NO production pathway as described herein. In particular, a vector may comprise the coding sequence of a protein involved in an NO production pathway as described herein and associated promoter and terminator sequences. The vector may further contain restriction sites of various types for linearization or fragmentation. The vector may further include an origin of replication that is required for maintenance and/or replication in a specific cell type. The vector also preferably contains one or more selection marker gene cassettes. A selectable marker gene cassette typically includes a promoter and transcription terminator sequence, operatively linked to a selectable marker gene. Suitable markers may be selected from markers that confer antibiotic resistance, herbicide resistance, visual markers, or markers that complement auxotrophic deficiencies of a host cell, in particular a microalga. For example, the selection marker may confer resistance to an antibiotic such as hygromycin B (such as the hph gene), zeocin/phleomycin (such as the ble gene), kanamycin or G418 (such as the nptII or aphVIII genes), spectinomycin (such as the aadA gene), neomycin (such as the aphVIII gene), blasticidin (such as the bsd gene), nourseothricin (such as the natR gene), puromycin (such as pac gene) and paromomycin (such as the aphVIII gene). In other examples, the selection marker may confer resistance to a herbicide such as glyphosate (such as GAT gene), oxyfluorfen (such as protox/PPO gene) and norflurazon (such as PDS gene). Visual markers may also be used and include for example beta-glucuronidase (GUS), luciferase and fluorescent proteins such as Green Fluorescent Protein (GFP), Yellow Fluorescent protein, etc. Two prominent examples of auxotrophic deficiencies are the amino acid leucine deficiency (e.g. LEU2 gene) or uracil deficiency (e.g. URA3 gene). Cells that are orotidine-5'-phosphate decarboxylase negative (ura3−) cannot grow on media lacking uracil. Thus a functional URA3 gene can be used as a selection marker on a host cell having a uracil deficiency, and successful transformants can be selected on a medium lacking uracil. Only cells transformed with the functional URA3 gene are able to synthesize uracil and grow on such medium. If the wild-type strain does not have a uracil deficiency, an auxotrophic mutant having the deficiency must be made in order to use URA3 as a selection marker for the strain. Methods for accomplishing this are well known in the art.

Successful transformants can be selected for in known manner, by taking advantage of the attributes contributed by the marker gene, or by other characteristics (such as the ability to produce NO) contributed by the inserted recombinant nucleic acid. Screening can also be performed by PCR or Southern analysis to confirm that the desired insertions have taken place, to confirm copy number and to identify the point of integration of coding sequences into the host genome. Activity (such as NO-producing activity) of the protein encoded by the inserted coding sequence can be confirmed using known assay methods. For example, NO levels can be measured using the fluorophore 4-amino-5-methylamino-2',7'-difluororescein diacetate (DAF-FM), which allows detection of nitric oxide ($ONOO^-$) which is in equilibrium with NO (St Laurent et al. 2015 Methods Mol Biol. 1220:339-345).

Methods for modifying endogenous gene expression by the use of artificial transcription factors (ATFs) or activator domains have also been described (Sera T. 2009, Adv Drug Deliv Rev 61:513-526; Maeder et al. 2013, Nat Methods 10:243-245; Cheng et al. 2013, Cell Res 23:1163-1171).

A further aspect of the application relates to the recombinant micro-organisms, in particular the recombinant microalgae, described herein. These micro-organisms are characterized in that they are genetically engineered to (over)produce NO as described herein and may further be characterized by their increased lipid content. In particular, the TAG content of the recombinant micro-organisms or microalgae described herein is increased to at least 110%, preferably at least 120%, more preferably at least 150% 160%, 170%, 180% or 190%, even more preferably at least 200% as compared to micro-organisms or microalgae wherein the NO production was not modulated such as a wild-type micro-organisms or microalgae or a micro-organism or microalgae that has been transformed with an empty vector.

In particular embodiments, the micro-organisms are characterized by the presence of one or more genetic modifications in the genome which affect NO synthesis, as detailed above.

The present invention will now be further illustrated by means of the following non-limiting examples.

EXAMPLES

Example 1: Effect of Overexpression of the Endogenous NOA Gene on Triacylglycerol Production in *Phaeodactylum tricornutum*

Material and Methods

*Phaeodactylum tricornutum* (Pt1) Bohlin Strain 8.6 CCMP2561 (Culture Collection of Marine Phytoplankton, now known as NCMA: National Center for Marine Algae and Microbiota) was used in example 1.

Genetic Construct for PtNOA Overexpression.

Genomic DNA was extracted from *Phaeodactylum tricornutum* Pt1 strain using the following procedure: $100 \cdot 10^6$ cells were harvested and frozen in liquid nitrogen. A volume of 20 µl Edward-Buffer (Tris-HCl 200 mM, pH 7.5; NaCl 250 mM; EDTA 25 mM; SDS 0.5%, w/v) was added, then samples were homogenized and debris removed by centrifugation. The supernatant was transferred to the same volume of isopropanol to precipitate DNA. After an additional 15 minute centrifugation at 10,000×g, the pellet was washed with ethanol 70%, dried and solubilized in TE buffer (10 mM Tris-HCL pH7, 1 mM EDTA). DNA concentration was measured using a Nanodrop 2000 spectrophotometer (Thermo Scientific). Using genomic DNA as matrix, a 2352-bp sequence was amplified by polymerase chain reaction (PCR) with the following oligonucleotides designed from Phatr2_56150 (Vardi et al. 2008), and carrying respectively XbaI and EcoRI restriction sites (underlined sequence): NOA-Fw XbaI 5'-TTTA<u>TCTAGA</u>ATGGTCCCCACTGGTTGTATG-3' (SEQ ID NO:8), NOA-Rev EcoRI 5'-TTTA<u>GAATTC</u>CTAATTACGCCCTACACCTTTTCTTC-3' (SEQ ID NO:9). PCR was performed using Phusion High Fidelity polymerase (Thermo Scientific) according to the manufacturer's instructions. PCR product was digested by EcoRI and XbaI, purified and cloned in the linearized expression vector. The expression vector used for overexpression corresponds to the pH4-GUS vector (De Riso et al. 2009 Nucleic Acids Res. doi: 10.1093/nar/gkp448). The vector contains a gene coding for resistance to zeocin (Shble), allowing selection of transformed cells. Expression of the NOA gene is controlled by the constitutive histone 4 promoter (H4pro). The vector sequence is provided in SEQ ID NO:6 (FIG. 2B) and the vector map is shown in FIG. 2A.

Transformation of P. tricornutum with the Genetic Construct and Selection of Strains Overexpressing NOA Wild-type P. tricornutum cells were transformed via particle-bombardment under aseptic conditions according to Russel Kikkert et al. (1993) (The Biolistic® PDS-1000/He device, Plant Cell, Tissue and Organ Culture, Volume 33, Issue 3, pp 221-226). A modified diatom protocol (Falciatore et al. 1999. Mar Biotechnol (NY) 1:239-251) was used. Briefly, three to four days-old Pt1 cultures were concentrated to $4 \cdot 10^7$ cells.500 $\mu l^{-1}$ and spread onto a 1% agar-plate containing artificial seawater (ESAW) medium (Table 1) with 50% reduced concentration of salt solution 1 and 2 (see Table 1 for the composition of salt solution 1 and 2). While vortexing, 2-3 µg of non-linearized plasmid were added to 25 µl ethanol-sterilized tungsten particles (SIGMA), together with 25 µl of 2.5 M $CaCl_2$ and 10 µl of 0.1 M spermidine. The mix was vortexed for three minutes, pelleted and washed two times (full speed, 5 s, room temperature) with 700 µl ethanol. Finally, DNA-coated tungsten particles were re-suspended in 25 µl ethanol. 12 µl of the mix were transferred onto a macrocarrier and the bombardment was carried out using 1,550 psi rupture disks (BioRad). After two to three days of incubation under continuous illumination, cells were transferred to the same kind of agar-plates containing 100 µg·$ml^{-1}$ zeocin (Promega) for the selection of resistant transformants (i.e. genetically modified strains). Colonies appearing 4 to 6 weeks afterwards were transferred to a new plate for one week, prior to the inoculation of 20 ml liquid cultures.

Culture of P. tricornutum at Different Scales, Different Media, Different $CO_2$ Supplies and Different Illumination Regimes.

For batch cultures, 20 ml or 50 ml cultures were grown in 250 ml Erlenmeyer flasks at 20° C. in ESAW medium. Cells were grown on a 12:12 light (30 µE $m^{-2} \cdot sec^{-1}$)/dark cycle.

For experiments in small photobioreactors, cells were pre-cultured in 250 ml Erlenmeyer flasks until they reached a density of $2 \text{-} 4 \cdot 10^6$ cells/ml. Cells were then centrifuged at 3,500 g for 5 minutes and re-suspended in either 10×ESAW medium (containing ten times more N and P; Table 1), medium E (Anandarajah et al. 2012 Applied Energy 96: 371-377; Table 2) or medium F (Benvenuti et al. J Appl Phycol 27:1425-1431; Table 3) to a final concentration of $2 \cdot 10^6$ cells/ml. These two additional media were chosen from the published literature because of their very different macronutrients and microelements composition, thus testing TAG accumulation in NOA overexpressor(s) across culture conditions. Cells were grown under a constant light regime at 20° C. in small scale bioreactors (Multi-Cultivator MC 1000, Photon Systems Instruments, Czech Republic), where temperature and light are tightly controlled. Culture mixing throughout cultivation time was provided by gas sparging as in air-lift photobioreactors; in order to test precise $CO_2$ supplies to bioreactor tubes, the Gas Mixing System GMS 150 (Photon Systems Instruments, Czech Republic) was used following manufacturer's instructions.

TABLE 1

Composition of ESAW 1× culture medium. Salt Solution 1 is autoclaved separately and added aseptically to the final medium. $NaNO_3$ and $NaH_3PO_4$ are added in 10× concentration or left absent.

|  | 10× Stock Concentration |  | Final medium concentration |  |
| --- | --- | --- | --- | --- |
| Salt Solution 1 |  |  |  |  |
| NaCl | 211.94 g/L | 100 ml per 1 L final medium | 21.194 g/L |  |
| $Na_2SO_4$ | 35.50 g/L |  | 3.550 g/L |  |
| KCl | 5.99 g/L |  | 0.599 g/L |  |
| $NaHCO_3$ | 1.74 g/L |  | 0.174 g/L |  |
| KBr | 0.863 g/L |  | 0.0863 g/L |  |
| $H_3BO_3$ | 0.230 g/L |  | 0.0230 g/L |  |
| NaF | 0.028 g/L |  | 0.0028 g/L |  |
| Salt Solution 2 |  |  |  |  |
| $MgCl_2 \cdot 6H_2O$ | 95.92 g/L | 100 ml per 1 L final medium | 9.592 g/L |  |
| $CaCl_2 \cdot 2H_2O$ | 13.44 g/L |  | 1.344 g/L |  |
| $SrCl_2 \cdot 6H_2O$ | 0.218 g/L |  | 0.0218 g/L |  |
| Major Nutrients |  |  |  |  |
| $NaNO_3$ | 46.67 g/L | 1 ml per 1 L final medium (or 10 ml/L 10× ESAW) | 46.67 mg/L |  |
| $NaH_2PO_4$ | 3.094 g/L | 1 ml per 1 L final medium (or 10 ml/L 10× ESAW) | 3.094 mg/L |  |

| TRACE METALS | stock | For 50 ml Trace Metal solution |  |  |
| --- | --- | --- | --- | --- |
| $Na_2EDTA \cdot 2H_2O$ | 3.09 g/100 mL | 5 ml | 1 ml Trace Metal solution per 1 L final medium | 3.09 mg/L |
| $ZnSO_4 \cdot 7H_2O$ | 0.73 g/100 ml | 0.5 ml |  | 7 µg/L |
| $CoCl_2 \cdot 6H_2O$ | 0.16 g/100 ml | 0.5 ml |  | 16 µg/L |
| $MnCl_2 \cdot 4H_2O$ | 0.54 g/100 mL | 5 ml |  | 540 µg/l |
| $Na_2MoO_4 \cdot 2H_2O$ | 0.148 g/100 ml | 50 µl |  | 1.48 µg/l |

TABLE 1-continued

Composition of ESAW 1× culture medium. Salt Solution 1 is autoclaved separately and added aseptically to the final medium. NaNO$_3$ and NaH$_3$PO$_4$ are added in 10× concentration or left absent.

| | | | | |
|---|---|---|---|---|
| Na$_2$SeO$_3$ | 0.017 g/100 mL | 50 µl | | 0.173 µg/l |
| NiCl$_2$•6H$_2$O | 0.149 g/100 mL | 50 µl | | 1.49 µg/l |
| CuSO$_4$•5H$_2$O | 0.98 g/100 mL | 50 µl | | 9.8 µg/l |

| Other | Stock Concentration | | | |
|---|---|---|---|---|
| EDTA-Iron | 3 g/L | | 1 ml per 1 L final medium | 3 mg/L |
| Vitamin stock | | | 1 ml per 1 L final medium | 1 mg/L Vitamin H<br>1 mg/L Vitamin B12<br>0.2 g/L Vitamin B1 |

| Final Medium Prep: | For 1 L | For 1 L solid: | ESAW1X | ESAW 0.5× |
|---|---|---|---|---|
| Ingredient Added before autoclave | Volume | Ingredient Added before autoclave | Volume | Volume |
| Salt Solution 2 | 100 ml | H$_2$O | 800 ml | 800 ml |
| NaH$_2$PO$_4$ | 1 ml (or 10 ml/L 10× ESAW) | Agar 1% (w/v) | 10 g | 10 g |
| Trace metals stock | 1 ml | Ingredient Added after autoclave | Volume | Volume |
| EDTA-Iron | 1 ml | Sea Salt1 | 100 ml/L | 50 ml/L |
| Water | up to 0.9 L | Sea Salt2 | 100 ml/L | 50 ml/L |
| Ingredient Added after autoclave | Volume | NaNO$_3$ | 1 ml/l | 1 ml/l |
| Salt Solution 1 | 100 ml | NaH$_2$PO$_4$ | 1 ml/l | 1 ml/l |
| NaNO$_3$ | 1 ml (or 10 ml/L 10× ESAW) | Trace metals stock | 1 ml/l | 1 ml/l |
| Vitamins | 1 ml | EDTA-Iron | 1 ml/l | 1 ml/l |
| | | Vitamins | 1 ml/l | 1 ml/l |

TABLE 2

Composition of medium E

| Medium E | Final Conc. mM | MW g/mol | Final Conc. g/L | Stock Conc. g/L | ml stock for 1 L Medium ml |
|---|---|---|---|---|---|
| Tris pH 8 | 40 | 121.14 | 4.8456 | — | — |
| NaCl | 363 | 58.44 | 21.19 | Salt solution 1 (10X) 256.5 g/L | 100 |
| Na$_2$SO$_4$ | 25 | 142.04 | 3.55 | | |
| KCl | 8.035 | 74.55 | 0.599 | | |
| NaHCO$_3$ | 2.071 | 84 | 0.174 | | |
| KBr | 0.725 | 119 | 0.0863 | | |
| H$_3$BO$_3$ | 0.372 | 61.8 | 0.023 | | |
| NaF | 0.667 | 41.99 | 0.028 | | |
| MgCl$_2$ · 6H$_2$O | 47.172 | 203.3 | 9.59 | Salt solution 2 (10X) 109.6 g/L | 100 |
| CaCl$_2$ · 2H$_2$O | 9.142 | 147.01 | 1.344 | | |
| SrCl$_2$ · 6H$_2$O | 0.082 | 266.6 | 0.0218 | | |
| NaNO$_3$ | 8.825 | 84.99 | 0.75 | 75 | 10 |
| NaH$_2$PO$_4$ | 0.217 | 119.98 | 0.026 | 5 | 5.36 |
| Na$_2$ EDTA · 2H$_2$O | 0.012 | 372.24 | 0.00436 | | 1 mL Trace metals stock solution + 1 ml Primary trace metal solution E |
| FeCl$_3$ · 6H$_2$O | 0.012 | 270.3 | 0.00315 | | |
| CuSO$_4$ · 5H$_2$O | 0.00016 | 249.7 | 4.00E−05 | | |
| Zn SO$_4$ · 7H$_2$O | 0.00031 | 287.5 | 8.80E−05 | | |
| CoCl$_2$ · 6H$_2$O | 0.00017 | 237.9 | 4.00E−05 | | |
| MnCl$_2$ · 2H$_2$O | 0.00445 | 161.9 | 7.20E−04 | | |
| Na$_2$MoO$_4$ | 0.00012 | 205.9 | 2.52E−05 | | |
| biotin (vit. H) | 4.1E−06 | 244.31 | 1.00E−06 | Solution Vitamines | 1 |

TABLE 2-continued

Composition of medium E

| Medium E | Final Conc. mM | MW g/mol | Final Conc. g/L | Stock Conc. g/L | ml stock for 1 L Medium ml |
|---|---|---|---|---|---|
| Cobalamin (Vit. B12) | 7.4E−07 | 1355.37 | 1.00E−06 | | |
| thiamine vit. B1 | 0.00066 | 300.81 | 2.00E−04 | | |

TABLE 3

Composition of medium F

| Medium F | Final Conc. mM | MW g/mol | Final Conc. g/L | Stock Conc. g/L | ml stock for 1 L medium ml |
|---|---|---|---|---|---|
| HEPES pH 7.5 | 100 | 238.3 | 23.83 | | |
| NaCl | 420 | 58.44 | 24.5448 | | |
| $MgSO_4 \cdot 7H_2O$ | 5 | 246.5 | 1.2325 | | |
| $Na_2SO_4$ | 3.5 | 142.04 | 0.49714 | | |
| $CaCl_2 \cdot 2H_2O$ | 2.5 | 147 | 0.3675 | | |
| $NaNO_3$ | 70 | 84.99 | 5.9493 | | |
| $KH_2PO_4$ | 0.88 | 136.09 | 0.1197592 | | |
| $K_2HPO_4$ | 2.3 | 174.2 | 0.40066 | | |
| $NaHCO_3$ | 10 | 84 | 0.84 | | |
| EDTA—Fe(III)—Na-salts | 0.11 | 367.1 | 0.040381 | | |
| $Na_2$ EDTA$\cdot 2H_2O$ | 0.18 | 372.24 | 0.0670032 | | |
| $ZnSO_4 \cdot 7H_2O$ | 0.004 | 287.5 | 1.15E−03 | 22 | 0.05227273 |
| $CoCl_2 \cdot 6H_2O$ | 0.0012 | 237.9 | 2.85E−04 | 10 | 0.028548 |
| $MnCl_2 \cdot 2H_2O$ | 0.0155 | 161.9 | 2.51E−03 | 180 | 0.01394139 |
| $CuSO_4 \cdot 5H_2O$ | 0.0013 | 249.7 | 3.25E−04 | 10 | 0.032461 |
| biotin (vit. H) | 0.0001 | 244.31 | 2.44E−05 | 0.1 | 0.24431 |
| Cobalamin (Vit. B12) | 0.0001 | 1355.37 | 1.36E−04 | 0.1 | 1.35537 |
| thiamine (vit. B1) | 0.0037 | 300.81 | 1.11E−03 | 0.5 | 2.225994 |

Measurement of NOA Gene Expression

To quantify the NOA mRNA level in the genetically modified strains, quantitative polymerase chain reaction (qPCR) was performed after reverse transcription (RT) of extracted RNA. RNA was extracted from $10^7$ cells that were previously pelleted, frozen in liquid nitrogen and stored at −80° C. until processing. A volume of 1 ml TriReagent® (SIGMA) was added to the frozen pellet and transferred to a new Eppendorf tube. After vortexing for 30 seconds, samples were incubated for 5 min at room temperature. 200 µl chloroform were added and tubes inverted and incubated for 15 min at room temperature. Phase separation was achieved by centrifugation (30 min, full speed, 4° C.). The upper phase was transferred to a new tube and RNA precipitated using 1 volume isopropanol (30 min, full speed, 4° C.), washed with 75% ice cold ethanol (5 min, full speed, 4° C.) and the pellet was dried in a Speed Vac system (Eppendorf Concentrator 5301) prior to resuspension in 30 µl DECP water (SIGMA) at 65° C. for 10 min. RNA was purified following a second ethanol precipitation using 1 volume of 5 M $NH_4^+$, acetate (2.5 M final concentration) and 1 volume isopropanol. Samples were incubated for 10 min on ice and centrifuged, washed, dried and re-suspended as described above. Concentration was determined using a NanoDrop device (Life Inc.). 1000 ng RNA were used for reverse transcription after DNAse treatment (QIAGEN) following manufacturer's instructions so as to yield 1000 ng cDNA, which were diluted to 10 ng·µl$^{-1}$. For quantitative real time PCR, the housekeeping gene oligonucleotides described by Siaut et al. (2007 Gene 406(1-2):23-35), namely 30S Ribosomal Protein Subunit (RPS) (5'-CGAAGTCAACCAGGAAACCAA-3' (SEQ ID NO:10) and 5'-GTGCAAGAGACCGGACATACC-3' (SEQ ID NO:11)) and tubulin A (TubA) (5'-CTGGGAGCTTTACTGCTTGGA-3' (SEQ ID NO:12) and 5'-ATGGCTCGAGATCGACGTAAA-3' (SEQ ID NO:13)), were used as internal controls. NOA-binding oligonucleotides were 5'-CCTGAAAAGTTCGCTACGCA-3' (SEQ ID NO:14) and 5'-CGGATCCTTTTTGCCCTGAG-3' (SEQ ID NO:15). The total qPCR reaction volume was 10 µl (120 nM per oligonucleotide, 20 ng cDNA, 5 µl 2×SYBR Green Sso Advanced (BioRad). A two-step thermo-profile in 40 cycles was applied after 3 min at 95° C. initial denaturation (95° C. 10 sec, 58° C. 30 sec) and a melt curve was detected (from 65° C. to 95° C. with a 0.5° C. increment) (BioRad CFX Connect Real-Time System). Evaluation of gene expression in 3 biological replicates each in technical triplicates were carried out using the CFX Connect Real-Time System software using TubA and RPS as internal controls.

Measurement of Nitric Oxide Using a Fluorescent Reporter

NO production was monitored using the fluorophore 4-amino-5-methylamino-2',7'-difluorofluorescein diacetate (DAF-FM), which allows the sensitive detection of low levels of nitric peroxide (ONOO—), which is in equilibrium with NO and thus indicates NO levels (St Laurent et al. 2015. Methods Mol Biol. 1220:339-45) and was previously used to detect NO levels in P. tricornutum cells (Vardi et al., 2008). 10 ml culture were diluted to $10^6$ cells/ml and cells were incubated with 20 µl 5 mM DAF-FM (1.5 h, room temperature, darkness, shaking). Cells were washed and re-suspended in 10 ml 10×ESAW media and aliquoted to 500 µl cultures on a 48 well culture plate. For the examination of DAF-FM-dependent detection of nitric peroxide, 150 µl of the culture were transferred into a 96 well plate and fluorescence was measured with a TECAN infinite M1000Pro plate reader (excitation wavelength at 488 nm, emission at 529 nm).

Measurement of TAG Accumulation by Nile Red Staining

A first method to measure the accumulation of TAG droplets consisted in their detection by Nile Red (Sigma Aldrich) fluorescent staining (Excitation wavelength at 485 nm; emission at 525 nm) as previously described (Abida et al., 2015). In brief, cells were diluted and adjusted to a cell density that was linearly correlated with Nile Red fluorescence. Nile Red solution (40 µl of 2.5 µg/mL stock concentration, in 100% DMSO) was added to 160 µl cell suspension. Oil bodies stained with Nile Red were then visualized using a Zeiss AxioScope.A1 microscope (FITC filter; Excitation wavelength at 488 nm; emission at 519 nm). The productivity, corresponding to the accumulation of TAG per volume and per time unit was calculated based on the staining by Nile Red, and expressed in relative fluorescence unit (Rfu) of Nile Red per mL and per day of incubation. Alternatively, Nile red fluorescence values were normalized to the cell concentration.

Measurement of TAG Accumulation by Mass Spectrometry

Glycerolipids were extracted from freeze-dried P. tricornutum cells grown in 50 mL of medium. About 50 to 100·10$^6$ cells are required for a triplicate analysis of TAGs. First, cells were harvested by centrifugation, then immediately frozen in liquid nitrogen. Once freeze-dried, the pellet was suspended in 4 mL of boiling ethanol for 5 minutes to prevent lipid degradation, and lipids were extracted as described by Simionato et al., (2013 Eukaryot Cell. 201, 12(5):665-76) by addition of 2 mL methanol and 8 mL chloroform at room temperature. The mixture was then saturated with argon and stirred for 1 hour at room temperature. After filtration through glass wool, cell debris was rinsed with 3 mL chloroform/methanol 2:1, v/v, and 5 mL of NaCl 1% were then added to the filtrate to initiate biphase formation. The chloroform phase was dried under argon before solubilizing the lipid extract in 1 ml of chloroform. Total glycerolipids were quantified from their fatty acids, in a 10 µl aliquot fraction a known quantity of 15:0 was added and the fatty acids present were transformed as methyl esters (FAME) by a 1 hour incubation in 3 mL 2.5% $H_2SO_4$ in pure methanol at 100° C. (Jouhet et al. 2003 FEBS Lett. 544(1-3):63-8). The reaction was stopped by addition of 3 mL water, and 3 mL hexane were added for phase separation. After 20 min of incubation, the hexane phase was transferred to a new tube. FAMEs were extracted a second time via the addition, incubation and extraction of another 3 ml hexane. The combined 6 ml were argon-dried and re-suspended in 30 µl hexane for gas chromatography-flame ionization detector (GC-FID) (Perkin Elmer) analysis on a BPX70 (SGE) column. FAME were identified by comparison of their retention times with those of standards (Sigma) and quantified by the surface peak method using 15:0 for calibration. Extraction and quantification were performed with at least three biological replicates. TAGs were analyzed and quantified by HPLC-MS/MS. For a technical triplicate analysis, an aliquot of the lipid extract containing 25 nmol of total fatty acid was dried under argon and dissolved in 100 µl of a methanol/chloroform solution (1:2) containing 125 pmol of 18:0/18:0/18:0 TAG as internal standard. For each replicate, 20 µl were injected in the HPLC-MS/MS system. The analytic device comprised a LC system with binary pumps (Agilent 1260 Infinity) coupled to a QQQ MS (Agilent 6460) equipped with a JetStream electrospray vane of injection. TAGs were separated by HPLC from other lipids using a diol column (Macherey-Nagel, EC 150/2 Nucleosil 100-5 OH) maintained at 40° C. The chromatography conditions were as follows: solvent A: isopropanol/water/ammonium acetate 1 M pH 5.3 (850/125/1); solvent B: Hexane/isopropanol/water/ammonium acetate 1 M pH 5.3 (625/350/24/1); gradient: 0 to 5 min 100% B, 5 to 30 min linear increase of A to 100%, 30 to 45 min 100% A, 45 to 50 min:linear increase of B to 100%, 50 to 70 min 100% B. Under these conditions, TAGs were eluted after 4-5 min of run. The various TAG species were detected from their m/z ratio by MS/MS using the Multiple Reaction Monitoring (MRM) mode. The various transition reactions used to identify the different TAG species are those previously established with Phaeodactylum tricornutum (Abida et al. 2015). Quantification was made using the Agilent Mass Hunter® software furnished by the MS supplier.

Results

Results shown in FIG. 3 show that after transformation of P. tricornutum cells with pH4-NOAOE vector, PtNOA is overexpressed. Two exemplary strains are shown in FIG. 3, NOAOE4 and NOAOEf, which were obtained by two independent transformation experiments.

Figure 4:
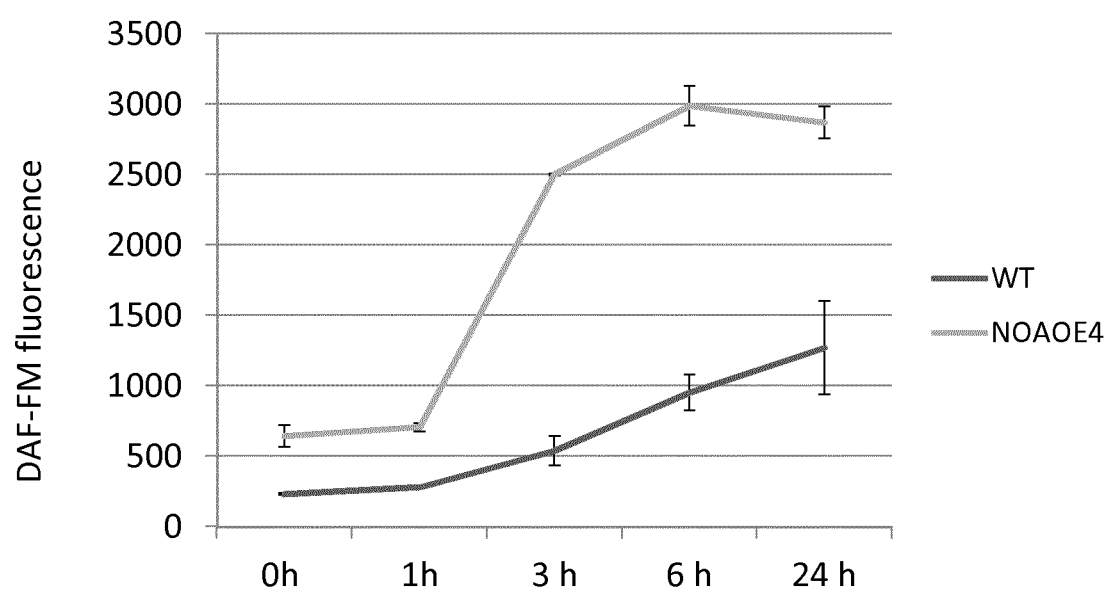
FIG. 4: Increased level of NO in *P. tricornutum* strains overexpressing NOA. Levels of NO were measured in 500 μl cultures using the NO-indicator DAF-FM and are expressed in relative fluorescence unit. Measurements were performed in triplicate at the indicated time points (A) or after three hours of incubation with DAF-FM (B).
Figure 4:
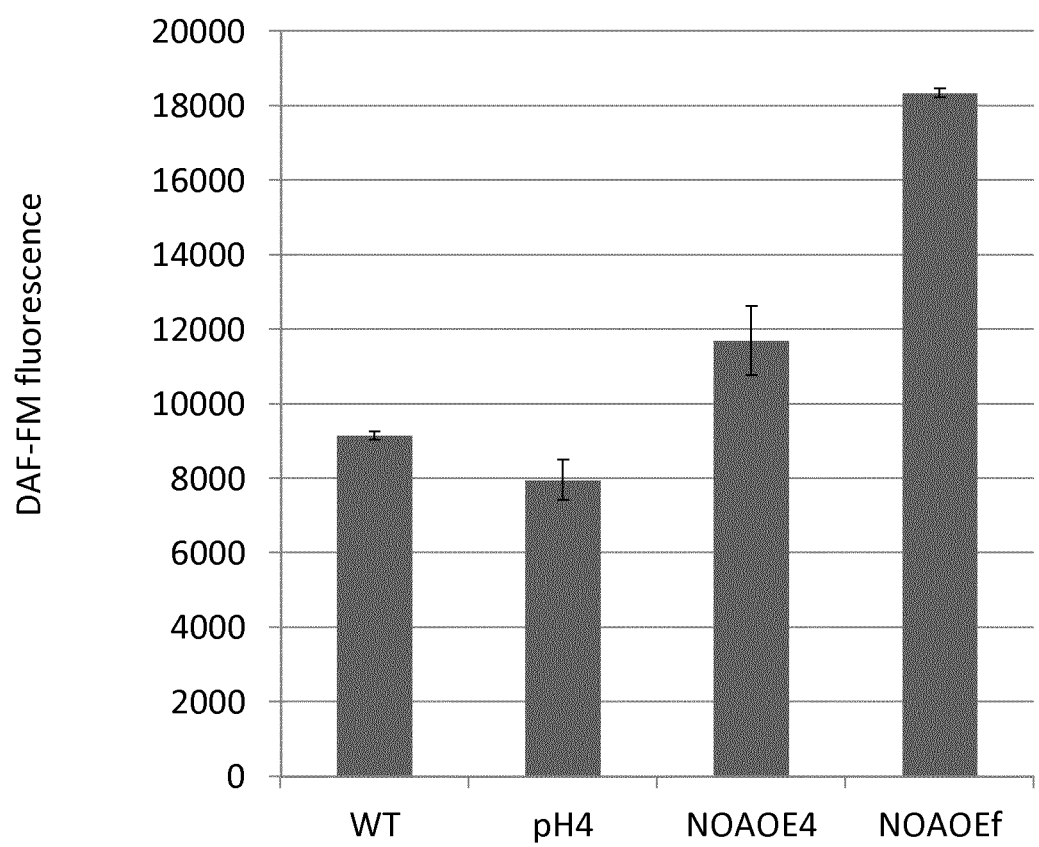
Figure 5:
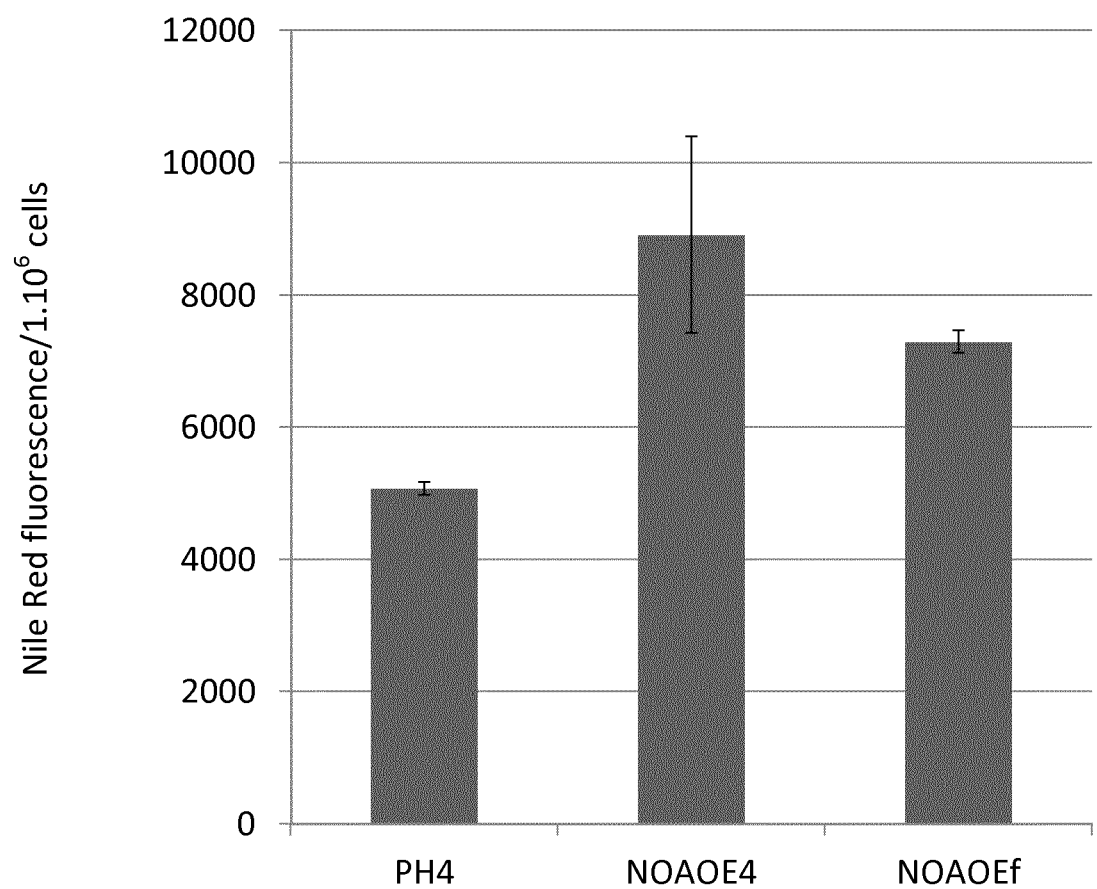
FIG. 5: Increased TAG per cell (A) and TAG productivity (B) in cultures of *P. tricornutum* performed in 50 mL culture flasks. Nile Red fluorescence was measured after 3 days of culture and was increased in the NOA overexpression strains (NOAOE4, NOAOEf) compared to a strain transformed with an empty vector (PH4).
Figure 5:
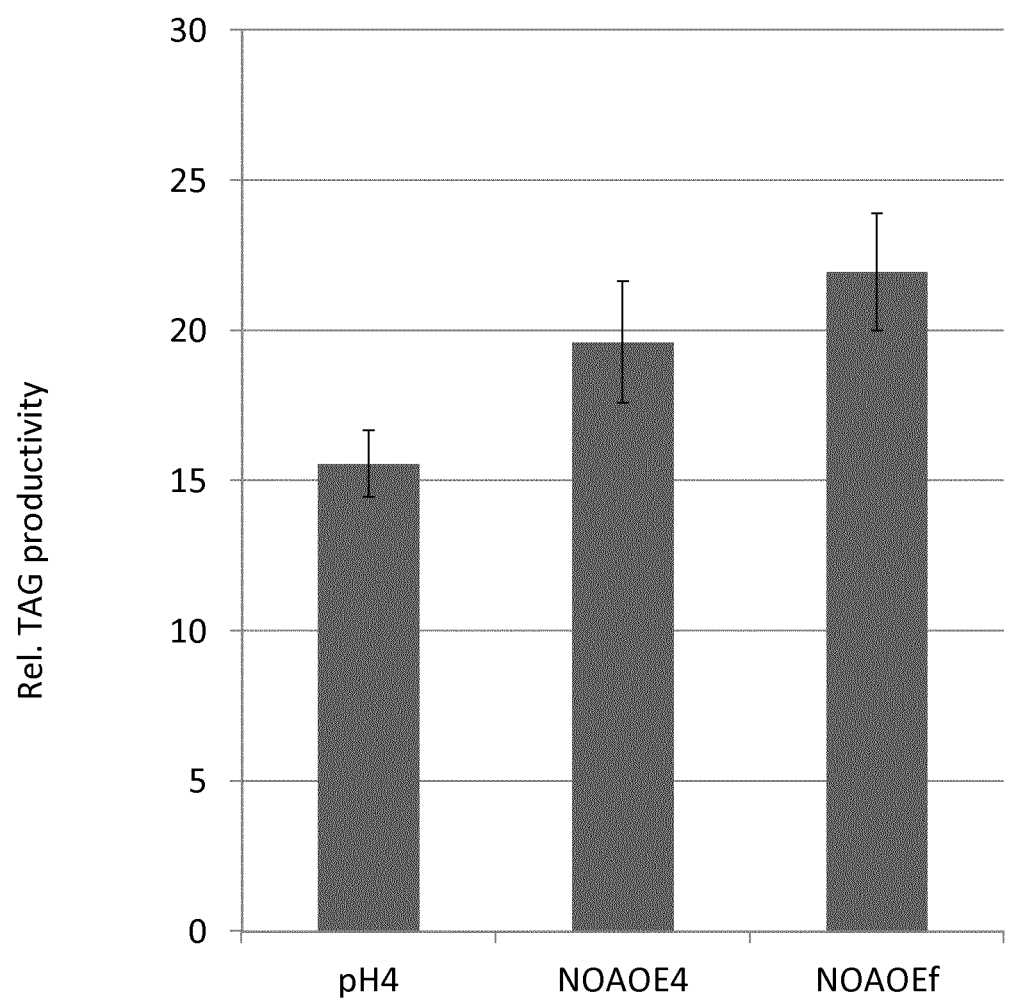
Figure 6:
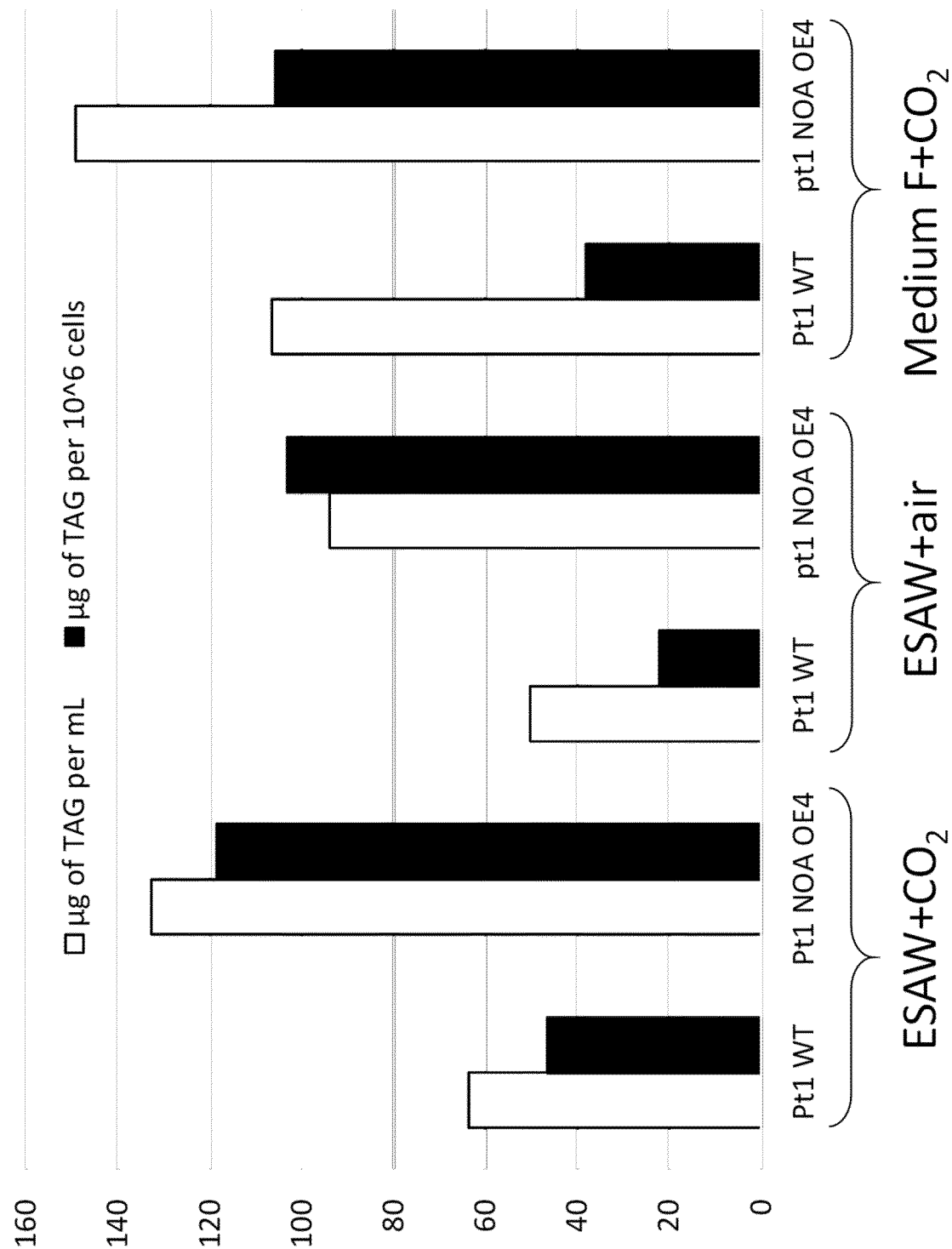
FIG. 6: Increased TAG productivity in cultures of *P. tricornutum* overexpressing PtNOA (Pt1 NOA OE4) or WT (Pt1 WT) grown in a photobioreactor in presence or absence of $CO_2$ supplies (air, 1.5% $CO_2$ and 0.5% $CO_2$) and in different media. TAG was quantified by mass spectrometry analysis. The relative productivity was defined by the level of TAG in collected cells, after extraction of lipids, purification of TAG and analysis by mass spectrometry.
Figure 7:
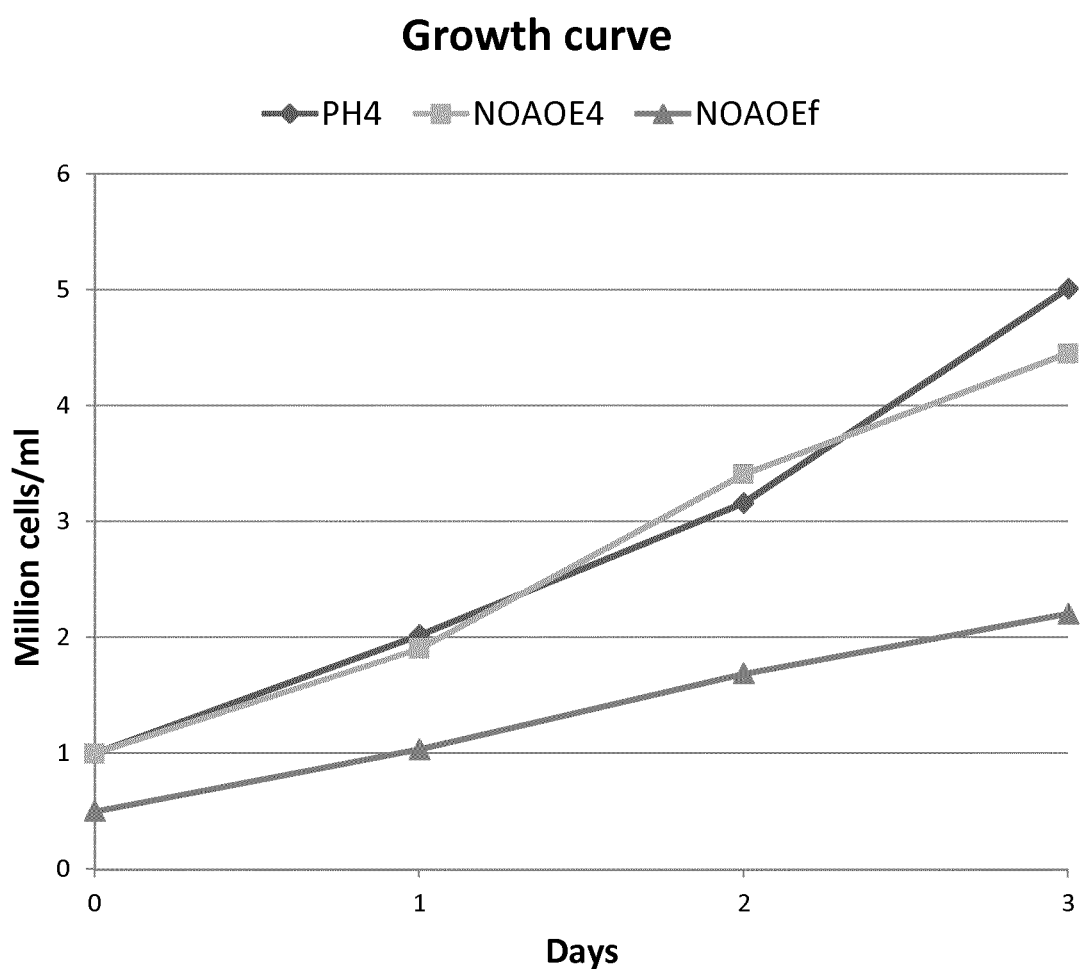
FIG. 7: Cell concentration in cultures of *P. tricornutum* performed in 10 mL culture flasks for PtNOA overexpressing strains (NOAOE4, NOAOEf) compared to a strain transformed with an empty vector (PH4).

The NOA overexpressing strains contained higher levels of NO, as shown by the DAF-FM fluorescent NO-indicator. The endogenous level of NO was higher and accumulated more rapidly than in a wild-type strain (FIG. 4A). After 3 hours of incubation with DAF-FM, increased levels of NO were measured in both NOAOE4 and NOAOEf strains as compared to WT Pt1 cells and Pt1 cells transformed with the pH4-GUS vector (FIG. 4B). NOA overexpressing strains also contained more TAG per cell (FIG. 5A) and increased TAG productivity (FIG. 5B). Also, as illustrated in FIG. 7, the cell concentration of NOA overexpressing strains (NOAOE4 and NOAOEf) was barely or not impacted by the NOA overexpression compared to the strain in which the NO production pathway was not modulated (pH4). The increased productivity of TAG in the P. tricornutum cells was observed in cells grown in different media, different volumes, different systems and different supplies of $CO_2$ compared to WT Pt1 cells and/or Pt1 cells transformed with the pH4-GUS vector described above (FIG. 6).

Example 2: Overexpression of a PtNOA Homolog from Nannochloropsis gaditana (NgNOA) in P. tricornutum and N. gaditana A PtNOA homolog (FIG. 1A) is present in Nannochloropsis gaditana (NgNOA; SEQ ID NO:3 and SEQ ID NO:4 for the nucleotide and amino acid sequence, respectively).

For the heterologous expression of NgNOA in Phaeodactylum tricornutum and the overexpression in Nannochloropsis gaditana, the coding sequence was optimized to match the codon optimization of both Chromalveolata species. Restriction sites for BamHI and XbaI were added at the 5'-end, and EcoRI and NdeI at the 3'-end of the codon optimized CDS to allow expression in the pH4 vector for expression in P. tricornutum, and in the PCT2Ng vector (SEQ ID NO:7) for the expression in N. gaditana, respectively. The codon optimized NgNOA coding sequence is designated as NgNOAoptCDS and has the following sequence:

(SEQ ID NO: 5)
GGATCCTCTAGAATGGCTCCCCACCTCTCCGGCCTCAACTTCCACTCCCT

CGTCAAGCGCTCCTCCGCTGCTGCTCTCCTCTTTCTCCCTCTTCATCATGA

AGCTCCCCTGCGTCGGCGCTTTCCAGGGCGTCGTCCGCGTCTGGTCCTCC

GCTGTCGCTCCCTCCCGCGCTGCTGTCCTCACCTCCTTCATGTCCCCCAA

GCGCCACGTCCTCAAGCGCATGCCCATCTCCGCTCTCTGCCGCCGCTCCA

CCATCATGGCTTCCCGCAAGGCTGGCGCTGGCCAGGGCGAGCACGAGGCT

GAGGGCGAGGGCATCTCCCCCGAGTCCATCTCCTCCACCGGCTCCAACGC

TGGCGGCAAGGGCATCGGCCGCGGCCCCCGCAACCGCCGCAAGATCGCTG

TCTCCGCTGAGGAGGAGGAGTTCTCCGCTCTCTCCGACTCCCGCACCTCC

GTCTCCGAGGAGAAGGACTCCATCCGCCGCCCCCGCGTCATCTCCCGCCC

CCCCTCCCGCCCCGTCAAGCGCACCATGACCATCAACCCCAACTGGCGCG

-continued
CTCACGGCGGCCCCGAGAACTCCATCAAGGGCCCCGAGGAGGCTGCTTCC
TCCTCCTCCGGCACCGCTGGCTCCGGCAAGGCTCGCGTCGGCAAGAACGG
CCCCCGCGGCGCTTCCCCCCTCGGCGCTGAGGTCCCCCGCTACGTCGAGG
ACGAGGACGAGGACGGCATCACCTTCCCCAAGGACATGGTCATCCGCGGC
CTCGACTCCCAGTCCTACGAGGAGGCTCGCCGCCAGGCTGTCCTCTCCGA
CGACGAGGGCGAGGAGGAGGAGTGGGCTGACGAGGGCGTCATGGTCGAGG
AGGAGGAGGGCGAGGACTTCGACGAGGAGGAGGAGGAGGAGGACTTCGAC
GAGGAGGAGGAGGAGGAGGACTTCGACGAGGGCGACGAGGAGGAGGAGGA
CGGCGCTCACCTCCCCCCCGTCCGCCCCGTCTCCATGGAGGAGCGCCTCC
GCCTCGCTGAGTCCGGCAACATCTTCAACCCCTACGTCGCTCGCATGCAC
ACCCGCGCTGGCACCGGCGAGGGCCCCTCCGGCGAGGCTGAGGACCCCGG
CCCCATGGACGGCGGCGGCCTCCGCTTCCTCGAGGAGGACGTCTCCCCCG
GCGAGAAGCGCGAGGAGGCTCGCCGCGCTCAGGCTCCCTCCCTCCCCGTC
AAGTTCCAGTACAAGGTCGTCGTCGGCGCTGGCACCTGCCCCGGCTGCGG
CAACGCTTTCCAGACCAAGAACGAGTCCTCCCCCGGCTTCCTCCCCCCCG
ACGTCTACGAGCGCCTCCAGGCTCAGATGACCGCTCTCCGCCCCGGCGCT
CCCCGCAAGCCCCGCCCCGACGCTCCCCCCCTCTCCAAGTCCGCTGCTGG
CGCTCTCCGCAAGAAGACCGAGACCCGCGGCGAGGAGGGCGACCTCTTCC
AGGGCCTCTCCGCTGAGGAGGAGGTCGAGATGCTCCTCTCCGGCAAGTCC
CGCGAGGAGTTCGAGATCGAGCGCGCTGCTGGCCGCGGCCGCGAGGCTCA
GGGCGGCGAGGTCGACCTCGACCTCGACGAGGAGGGCAAGGAGGAGAAGG
AGGGCGAGGGCCGCGAGGGCGAGGAGGGCGGCGAGGGCGAGGAGGAGGAG
GAGGAGTTCCGCGCTGTCATCTGCCAGCGCTGCCACAAGCTCAAGCACTA
CGGCGACGTCGAGGACGCTCTCCGCCCCGGCTGGTCCGCTAACGAGCTCC -continued
TCACCCCCGAGCGCTTCCGCGAGCTCGTCTCCGTCGTCCGCCGCAAGCGC
TGCGCTGTCGTCTGCCTCGTCGACATCTTCGACTTCCACGGCTCCCTCCT
CTACAACCTCCCCCGCATCGTCGGCTCCAACCCCGTCCTCGTCGCTGTCA
ACAAGGCTGACCTCCTCCCCGCTGACTTCTCCCAGGACCGCGTCCGCATC
TGGGTCAAGCAGGAGCTCGAGAAGGTCGGCATGACCGACGTCTCCACCCG
CGACATCCACCTCATCTCCTGCAAGACCGGCAACAACGTCCGCCCCCTCC
TCCGCTCCATGAAGCAGATGGCTCGCCAGCGCCGCCGCGACCTCTACGTC
ATCGGCGCTGCTAACGTCGGCAAGTCCACCTTCATCAACCGCCTCATCGA
GCTCGGCCGCTCCGGCGGCGACGCTCAGCGCAAGAAGAAGAAGCAGG
GCGAGCAGTCCAAGGGCGGCTCCCTCGTCACCACCTCCGCTCTCCCCGGC
ACCACCCTCGACTTCATCGAGGTCGACCTCGGCGACAAGGTCTCCCTCTA
CGACACCCCCGGCCTCATCCTCCCCCACCAGATCACCACCCTCCTCAACA
CCGAGGAGCTCAAGGCTGTCATCCCCCAGAAGCGCATCAACCACGTCACC
CTCCGCCTCAAGGAGGGCAAGTCCGTCCTCCTCGGCGGCCTCGTCCGCCT
CGACATGCTCGAGGGCCGCCCCTTCCTCTTCACCTTCTACGTCTCCAACG
AGGTCAAGCTCCACCAGACCGCTACCGACCGCGCTGGCGAGTTCCTCGAC
TCCCACCTCGGCGAGCTCATCTCCCCCCCCTTCACCCAGGAGCGCCGCGC
TGCTATGGGCCCCTGGGTCCCCCGCGACTTCGAGATCGAGGGCACCGGCT
GGAAGACCTCCGCTGTCGACATCGTCATCTCCGGCCTCGGCTGGATCTCC
GTCACCGGCGCTCTCGACTGCAAGGTCCGCGTCATGGCTCCCGAGGCTGT
CGGCGTCCGCCTCCGCTCCCCCCTCATGCCCTACGAGACCTGGGCTACCA
CCGCTAAGTGGACCGGCCTCCGCGCTGTCAAGTCCGACAAGCAGAAGGGC
TCCTCCCGCTAAGAATTCCATATG.

The invention claimed is:

1. A method for increasing the production of triacylglycerol (TAG) in a microalga, said method comprising:
culturing a recombinant microalga which has been transformed with a recombinant nucleic acid encoding a NOA protein having an amino acid sequence that is at least 90% identical to the amino acid sequence of SEQ ID NO: 2 or SEQ ID NO: 4 under conditions suitable for the production or overproduction of nitric oxide (NO) by said microalga, so as to enhance the production of said TAG.

2. The method according to claim 1, wherein said microalga has been transformed with a recombinant nucleic acid encoding a NOA protein having an amino acid sequence that is at least 90% identical to the amino acid sequence of SEQ ID NO: 2.

3. The method according to claim 2, wherein said NOA protein is the *Phaeodactylum tricornutum* NOA (PtNOA) protein having the amino acid sequence of SEQ ID NO:2.

4. The method according to claim 1, wherein said NOA protein is the *Nannochloropsis gaditana* NOA (NgNOA) protein having the amino acid sequence of SEQ ID NO:4.

5. The method according to claim 1, wherein said microalga has been transformed with a recombinant nucleic acid encoding a NOA protein having an amino acid sequence that is at least 90% identical to the amino acid sequence of SEQ ID NO: 4.

6. The method according to claim 1, wherein the microalga is a *Chromalveolata*.

7. The method according to claim 6, wherein the *Chromalveolata* is a Bacillariophyceae or a Eustigmatophyceae.

8. The method according to claim 7, wherein the Bacillariophyceae is *Phaeodactylum tricornutum*.

9. The method according to claim 1, wherein the triacylglycerol content is increased in said recombinant microalga at least 150%, compared to a corresponding microalga wherein the NO production pathway was not modulated.

10. The method according to claim 1, wherein said culturing conditions are suitable for growth of the recombinant microalga, such that the production of the triacylglycerol (TAG) is concomitant with the growth of the recombinant microalga.

* * * * *

SEQUENCE LISTING

<160> NUMBER OF SEQ ID NOS: 15

<210> SEQ ID NO 1
<211> LENGTH: 2427
<212> TYPE: DNA
<213> ORGANISM: Phaeodactylum tricornutum

<400> SEQUENCE: 1
atggtcccca ctggttgtat gagatcaaag aacaaacaga gtactgctgc tgacggaaga    60
aggtcgattg gaagtcgatc caacgctgga ctggtcatgt tctttagtat gactatctta   120
tcgacacgac gatttgcggc agcttggggtt tttcagagta gtggaataca acgatcaata   180
ccatccacgc ataggatgcg aacgaatttt gctttgtcga cgcgctgctt tgcttcttca   240
tccgacaacc atgacgaaga ggaacaacga gactctccga aacaaagatc caaacgcagc   300
caaactaatc ggtccaagaa attcaaaatt gctgaatcaa tcgaccagag caaaatagat   360
aagctagcac aagcattcga tgaactcgct cggaaggaag gcttcgactc gtcaacagca   420 cgcttttgccg acgatgtgac gttcgaggac aagtttgacg acgattcgtt tctggacgat   480
gacgatgata acaacaaaga taaagtggga aacttgcacc tagatgcatc catgttcagt   540

```
ttaagtgact ttatagataa gagtgaggaa gatggcggca atccaaccga tcaagatgac    600
gaggactacc ttgatttttgg tgcagacatt gacatgagta tagaagcaag gattgccgct    660
gccaaacggg atatggatct cggtcgagtc agcgcccctc ccgatatgag atcctcgcgc    720
agggaggtaa ctgcagccga ccttcgcaaa cttggatttc gaaccgaggc aaacccattc    780
ggcaacgacg aaactccacg gaaggagcgc ttccagttgg taacaaactc catgtcgtgc    840
tccgcctgtg gatcggactt tcaatgccac aacgaagatc ggcccggata tctgcctcct    900
gaaaagttcg ctacgcaaac agcacttgga aaaatagaac agatgcaaaa gttgcaggat    960
aaagcagaaa agcggaatg gacacctgaa gatgagattg aatggttgat tcagactcag   1020
ggcaaaaagg atccgaacaa agaaatgcag gaggtgcccc agatcgatgt tgattctttg   1080
gcaggggaaa tgggccttga cctcgtagag ctttccaaaa gatggttat ttgcaagcgc    1140 tgtcacggtc tgcaaaactt tggaaaagtg caagattccc tccgacctgg gtggacgaag   1200
gagccactgt tgtcgcagga gaaatttcgt gaattgttaa ggccaatcaa ggaaaagccg   1260
gcagttatcg ttgcattggt cgatcttttt gattttttcgg ggtctgtgct ccctgagctt   1320
gatgaaatcg ctggtgaaaa ccctgtaatt cttgcggcca acaaggcgga tcttcttcca   1380
agtgaaatgg acgcgtgcg agctgagagt tgggttcgac gcgagctcga ataccttgga   1440
gtcaagtcgt tggccggtat gagaggagca gttcggcttg tcagctgcaa gactggagct   1500
gggattaatg atttgctgga gaaagcaaga ggattagccg aggaaatcga cggcgacata   1560
tacgtcgtcg gggctgcaaa tgcaggaaaa agtacgcttt tgaattttgt tctaggtcag   1620
gacaaggtga acagatcacc cggaaaagca cgagcaggca acaggaatgc cttcaagggc   1680
gcggtgacga caagtccact gccaggcaca acgcttaagt tcatcaaagt cgatttaggc   1740
ggcggtcgaa gtctatatga cactcctggt cttctggtat taggcactgt gacacagtta   1800 ctgaccccccg aagagctgaa gatagttgtt cccaaaaagt atgtcaaacc gatcaaactg   1860
atattcgatt cacagtcaat aatgttcaaa ctaacacctc gttcctcaaa caggccaatt   1920
gaacctgtca ccctccggct ctctaccgga aagtgcgttc tagttggagg attggcccgc   1980
atcgagttaa tcggcgactc aagaccctt atgttcacat ttttttgttgc taatgagatc   2040 aagctccacc ctactgacat agagagagcc gatgagttcg ttctaaagca cgctggtggc   2100
atgttgactc caccgctagc acccggacca aaacgtatgg aagagattgg agaatttgaa   2160
gatcacatcg tggatatcca gggtgctggc tggaaagaag ctgctgctga tatcagtctt   2220
accggactag gatgggtggc cgttacagga gcagggacag cgcaagtaaa aataagtgtt   2280
ccgaaaggta ttggtgtatc ggtgcggcct ccgcttatgc ctttcgatat ctggaaagtt   2340
gcatcgaagt ataccggaag tcgagctgta agaaagtcat ccaaactggc gaatgggaaa   2400
cgaagaaaag gtgtagggcg taattag                                       2427
```

<210> SEQ ID NO 2
<211> LENGTH: 783
<212> TYPE: PRT
<213> ORGANISM: Phaeodactylum tricornutum

<400> SEQUENCE: 2

Met Val Pro Thr Gly Cys Met Arg Ser Lys Asn Lys Gln Ser Thr Ala
1               5                   10                  15

Ala Asp Gly Arg Arg Ser Ile Gly Ser Arg Ser Asn Ala Gly Leu Val
            20                  25                  30

Met Phe Phe Ser Met Thr Ile Leu Ser Thr Arg Arg Phe Ala Ala Ala

```
                35                  40                  45
Trp Val Phe Gln Ser Ser Gly Ile Gln Arg Ser Ile Pro Ser Thr His
 50                  55                  60

Arg Met Arg Thr Asn Phe Ala Leu Ser Thr Arg Cys Phe Ala Ser Ser
 65                  70                  75                  80

Ser Asp Asn His Asp Glu Glu Gln Arg Asp Ser Pro Lys Gln Arg
                 85                  90                  95

Ser Lys Arg Ser Gln Thr Asn Arg Ser Lys Lys Phe Lys Ile Ala Glu
                100                 105                 110

Ser Ile Asp Gln Ser Lys Ile Asp Lys Leu Ala Gln Ala Phe Asp Glu
                115                 120                 125

Leu Ala Arg Lys Glu Gly Phe Asp Ser Ser Thr Ala Arg Phe Ala Asp
130                 135                 140

Asp Val Thr Phe Glu Asp Lys Phe Asp Asp Ser Phe Leu Asp Asp
145                 150                 155                 160

Asp Asp Asp Asn Asn Lys Asp Lys Val Gly Asn Leu His Leu Asp Ala
                165                 170                 175

Ser Met Phe Ser Leu Ser Asp Phe Ile Asp Lys Ser Glu Glu Asp Gly
                180                 185                 190

Gly Asn Pro Thr Asp Gln Asp Asp Glu Asp Tyr Leu Asp Phe Gly Ala
                195                 200                 205

Asp Ile Asp Met Ser Ile Glu Ala Arg Ile Ala Ala Lys Arg Asp
                210                 215                 220

Met Asp Leu Gly Arg Val Ser Ala Pro Pro Asp Met Arg Ser Ser Arg
225                 230                 235                 240

Arg Glu Val Thr Ala Ala Asp Leu Arg Lys Leu Gly Phe Arg Thr Glu
                245                 250                 255

Ala Asn Pro Phe Gly Asn Asp Glu Thr Pro Arg Lys Glu Arg Phe Gln
                260                 265                 270

Leu Val Thr Asn Ser Met Ser Cys Ser Ala Cys Gly Ser Asp Phe Gln
                275                 280                 285

Cys His Asn Glu Asp Arg Pro Gly Tyr Leu Pro Pro Glu Lys Phe Ala
                290                 295                 300

Thr Gln Thr Ala Leu Gly Lys Ile Glu Gln Met Gln Lys Leu Gln Asp
305                 310                 315                 320

Lys Ala Glu Lys Ala Glu Trp Thr Pro Glu Asp Glu Ile Glu Trp Leu
                325                 330                 335

Ile Gln Thr Gln Gly Lys Lys Asp Pro Asn Lys Glu Met Gln Glu Val
                340                 345                 350

Pro Gln Ile Asp Val Asp Ser Leu Ala Gly Glu Met Gly Leu Asp Leu
                355                 360                 365

Val Glu Leu Ser Lys Lys Met Val Ile Cys Lys Arg Cys His Gly Leu
                370                 375                 380

Gln Asn Phe Gly Lys Val Gln Asp Ser Leu Arg Pro Gly Trp Thr Lys
385                 390                 395                 400

Glu Pro Leu Leu Ser Gln Glu Lys Phe Arg Glu Leu Leu Arg Pro Ile
                405                 410                 415

Lys Glu Lys Pro Ala Val Ile Val Ala Leu Val Asp Leu Phe Asp Phe
                420                 425                 430

Ser Gly Ser Val Leu Pro Glu Leu Asp Glu Ile Ala Gly Glu Asn Pro
                435                 440                 445

Val Ile Leu Ala Ala Asn Lys Ala Asp Leu Leu Pro Ser Glu Met Gly
                450                 455                 460
```

Arg Val Arg Ala Glu Ser Trp Val Arg Glu Leu Glu Tyr Leu Gly
465                 470                 475                 480

Val Lys Ser Leu Ala Gly Met Arg Gly Ala Val Arg Leu Val Ser Cys
                485                 490                 495

Lys Thr Gly Ala Gly Ile Asn Asp Leu Leu Glu Lys Ala Arg Gly Leu
            500                 505                 510

Ala Glu Glu Ile Asp Gly Asp Ile Tyr Val Val Gly Ala Ala Asn Ala
            515                 520                 525

Gly Lys Ser Thr Leu Leu Asn Phe Val Leu Gly Gln Asp Lys Val Asn
        530                 535                 540

Arg Ser Pro Gly Lys Ala Arg Ala Gly Asn Arg Asn Ala Phe Lys Gly
545                 550                 555                 560

Ala Val Thr Thr Ser Pro Leu Pro Gly Thr Thr Leu Lys Phe Ile Lys
                565                 570                 575

Val Asp Leu Gly Gly Gly Arg Ser Leu Tyr Asp Thr Pro Gly Leu Leu
            580                 585                 590

Val Leu Gly Thr Val Thr Gln Leu Leu Thr Pro Glu Glu Leu Lys Ile
        595                 600                 605

Val Val Pro Lys Lys Pro Ile Glu Pro Val Thr Leu Arg Leu Ser Thr
610                 615                 620

Gly Lys Cys Val Leu Val Gly Gly Leu Ala Arg Ile Glu Leu Ile Gly
625                 630                 635                 640

Asp Ser Arg Pro Phe Met Phe Thr Phe Phe Val Ala Asn Glu Ile Lys
                645                 650                 655

Leu His Pro Thr Asp Ile Glu Arg Ala Asp Glu Phe Val Leu Lys His
            660                 665                 670

Ala Gly Gly Met Leu Thr Pro Pro Leu Ala Pro Gly Pro Lys Arg Met
        675                 680                 685

Glu Glu Ile Gly Glu Phe Glu Asp His Ile Val Asp Ile Gln Gly Ala
690                 695                 700

Gly Trp Lys Glu Ala Ala Asp Ile Ser Leu Thr Gly Leu Gly Trp
705                 710                 715                 720

Val Ala Val Thr Gly Ala Gly Thr Ala Gln Val Lys Ile Ser Val Pro
                725                 730                 735

Lys Gly Ile Gly Val Ser Val Arg Pro Pro Leu Met Pro Phe Asp Ile
            740                 745                 750

Trp Lys Val Ala Ser Lys Tyr Thr Gly Ser Arg Ala Val Arg Lys Ser
        755                 760                 765

Ser Lys Leu Ala Asn Gly Lys Arg Lys Gly Val Gly Arg Asn
770                 775                 780

<210> SEQ ID NO 3
<211> LENGTH: 5262
<212> TYPE: DNA
<213> ORGANISM: Artificial Sequence
<220> FEATURE:
<223> OTHER INFORMATION: Nannochloropsis gaditana

<400> SEQUENCE: 3
attttcttgt tatcttatac acacatattc acaggaggat tgtaattagt gaaactggtg      60
gcaaagggtt tatcaacggt ggctgcgctt cttcctgccc atcgaacagc aacttcagcc     120
actcaaacca cattactttt cgccctgtga atttttggtc aacttcatgg caccacactt     180
gagtggccta aattttcatt cattggtcaa gagatcgtcc gctgcagcgc ttctttttctc    240

-continued

| | |
|---|---|
| gctcttcatc atgaagctac cctgtgtcgg tgctttccaa ggagtagtgc gggtttggag | 300 |
| ttcagcagtg gctccatcgc gagctgccgt actcaccagc tttatgtctc ccaaacgaca | 360 |
| cgtgctaaaa agaatgccaa tttcagcgtt gtgcaggcgg tcaacaatca tggcgtcccg | 420 |
| gaaagcgggg gcgggacagg gcgagcacga ggcagaaggg gagggaatct caccagaatc | 480 |
| gatctcgtcg acaggaagca acgcaggagg caaaggaatc gggcgcggac cccgaaatcg | 540 |
| acggaaaata gccgtaagcg cggaagagga agagttttca gccctgtccg actcgaggac | 600 |
| ctcggtttcc gaagagaagg actcgattcg aaggccgcgg gtcatttctc gccctccctc | 660 |
| ccgcccgtc aagcgaacga tgaccatcaa ccctaattgg cgggcgcatg gaggccctga | 720 |
| gaacagtata aagggaccgg aggaggccgc ttcgtcgtcc tctggtaccg cggggagcgg | 780 |
| aaaggcccgt gtgggaaaga atgggccgcg ggtgcgagt cccctggggg cggaggtacc | 840 |
| ccgctatgtg gaggatgagg atgaggatgg gatcacgttc ccgaaagata tggtaatccg | 900 |
| aggcttggat agccagagct acgaggaagc gcgccgacag gccgtgctga gcgatgacga | 960 |
| gggcgaggag gaggagtggg ccgacgaggg ggtcatggtg gaggaggagg aggggagga | 1020 |
| ctttgacgag gaggaggagg aggaagactt tgacgaggag gaggaggagg aagactttga | 1080 |
| cgagggggac gaagaggagg aggacggcgc tcaccttccc ccagtgcggc ccgtgtcgat | 1140 |
| ggaggagcgc ctccgcctgg cggagtccgg caatatcttc aaccccctacg tagcccggat | 1200 |
| gcacacgcgc gcgggcaccg gggaggggcc gtctggggag gcggaagacc ctggcccgat | 1260 |
| ggacgggggc ggtttgcggt tcttggagga ggatgtgagc ccgggggaga aaagggagga | 1320 |
| agcgcgccgg gcccaggcgc cctccctgcc cgtcaagttc cagtacaagg tggtggtggg | 1380 |
| ggccgggacg tgcccgggct gcgggaacgc gtttcagacc aaaaatgaat cctcccccgg | 1440 |
| cttcctcccc cccgacgtct acgagcggct tcaggcccag atgacggcgc tgcgaccagg | 1500 |
| cgctccccga aagccgaggc cggacgcccc ccccctctcg aagtcagcgg caggggcgct | 1560 |
| gcggaagaag acgagacga gggggaaga ggggatttg ttccaaggcc tgagcgcaga | 1620 |
| ggaggaggtg gaaatgcttt tgtcgggcaa gagccgtgag gagtttgaaa tagagagagc | 1680 |
| ggcgggggaga gggaggggagg cccagggcgg ggaggtagat cttgacctcg acgaggaggg | 1740 |
| gaaggaagag aaggagggag agggaaggga aggggaagaa ggggggaag gggaggagga | 1800 |
| ggaggaagaa tttcgtgcgg taattttgcca gcggtgccac aagctgaagc actacgggga | 1860 |
| cgtggaggac gccctgcgcc cggggtggag cgcgaacgag ctgttgacgc cggagcgctt | 1920 |
| ccgggagttg gtgagcgtgg tgcgacgaa acgctgcgcc gtggtgtgtc tggtggacat | 1980 |
| cttcgacttc catgggtccc ttctctacaa cctgccccgc atcgtgggct ccaacccggt | 2040 |
| gctggtggcc gtgaacaagg ctgacctcct ccccgcggac ttcagccagg accgagtccg | 2100 |
| gatctgggtc aagcaggaac tggagaaggt ggggatgacg gacgtgagca cgcgcgacat | 2160 |
| ccacctgatc tcctgcaaga cggggaacaa cgtccggccc ttgctgcggt ccatgaagca | 2220 |
| aatggcgcgc cagcgcaggc gggatctgta cgtgatcggc gcgcaaacg tgggcaagtc | 2280 |
| gaccttcatc aaccggctga ttgagctggg tcggagtgga gggacgcgc agaggaagaa | 2340 |
| gaagaagaag caggggaac agagcaaagg cgggtctctg gtcacgacga gcgccttacc | 2400 |
| gggcacgacc ttggacttca tcgaggtgga cctgggggac aaggtctccc tctacgacac | 2460 |
| cccgggcctc atcttgccgc accagatcac cacgctgctg aacacggaag agctcaaggc | 2520 |
| agtaattccc cagaagcgca tcaaccacgt gaccctgcgc ctgaaggagg caagagcgt | 2580 |
| cctcctgggc gggctagtcc gcttggacat gctggagggt cggcccttcc tcttcacatt | 2640 |

```
ctacgtctcg aacgaggtca agctccacca aacagccacg gaccgggccg gggaattttt    2700
ggacagtcac ctcggtgaac taatctcgcc gcccttcacg caggaacgcc gagcggccat    2760
ggggccatgg gtacctcgtg acttcgagat cgaagggacg ggctggaaaa cctcagccgt    2820
tgacatagtc atctctggct tagggtggat atctgtcacc ggcgcattgg actgtaaggt    2880
ccgagtcatg gcaccggagg cggtgggtgt gcgtttgcgg agtccattga tgccttacga    2940
gacctgggcg acaacagcca agtggacggg gctcagggcc gtcaagagtg acaagcaaaa    3000
agggagcagc agataggaag aggaaagttt taccctgtcg tgaaagtgct gatgaagata    3060
aactatcaag aaaataatca tgtgcattca caaaaacagc tcgttgttgt ttttttgttt    3120
cctctttgat cagacctttg gtgatattcg attctatttc ttgcccgcat ctcataggat    3180
tgcgattgta atctccgcaa cagcgttcaa ccagaaaacg tacaacgatc tgagcaaagg    3240
atagatggct aactctggga ggtcttttgc ttggtatttg tagccggaag atggctttgt    3300
ggtccagggc ttgtattttc tggccccac gactgatcta cgtccagagg ggtctgaggg    3360
actccatgca agccaccaag cacgtacatt tcacacgctc gtacattacg gcattttacg    3420
ctccgatatc gcgccacggg aatgattggt cacgcccatc aaagcactcg ccggttcttt    3480
catctctata ctcaaatatc cttacccttc ctcgacagtc gacgcacgat gaacttcgcg    3540
gacgctgcca cgacgcactc agccgtgaaa ggccatgcct cccagggac cgaaagggag    3600 gaccaagctg gtggtgacgc tggaaggacc tccctagcca tggcatgacc ggccctcttc    3660
acgacgtgaa ggacacagaa gacgacaccg actgcgttgt ttatgtcctc aattttcacc    3720
cccgcaacac ggcggacaag gaaggcaaga tcaacaatgc gatcaacttc gccgatgcag    3780
aattggagga acatcacgtc ctcctgggag tgtttcttgg tcaatgtgtc gtttcccacc    3840
tccttccacc caaacgcaat tctaatacct tgtaccttgt tgcccgaata ccaacacctc    3900
gtacccctaa cacgcacaac acgctttccg acaacgccgg aagactcccc gtccgtacac    3960
gcgaccccct taaccgcgcc gacatcgagc cggactacta caagcccttc gtctcccctg    4020
agcttgtcaa caaacgcaat gcagaggcgc acaagcacaa ttcgcctcta ctccgcggtg    4080
acctaaacgt gacgtacgag cgtacacagg acaagggctt cttggaactt ggccgtgcgc    4140
ggagtgccac aaaatttgag tcctggcttg gtcttcgcat cataatcgaa ggtccagctt    4200
tgaacgaccc cggcccaagc aacacgagca gatcgtgtgg gtcgatgaat acaagtttac    4260
caatgggcag gatttcaagg tgttcttttg gggcgggagc ctgtggcagc tgtgcaagaa    4320
gtgggccgat gcgaaccgca ctcaatcggg gggagacgac atggtgcgtt tttgtttcga    4380
ggcccactcc gcttggtgtt cgtgcatgct cacaacgtcc agacgcacct cttctagaca    4440
caggaccggg cggtggaggc gggctacata gcgccatcct tggatgttgg cgccacgaaa    4500
gccctggtag catccagtgg aatagaaacc ctcttccagc acgtggctgt gataaagaac    4560
aagtaagcgc acatccatga ttggacatct taccccttccg tgcatgcatt tctggttgct    4620
cgttccgctc atttatggac gccatcccta cagagcaaag gatctcgatt gaggaggcgg    4680
ctttgggaga gcagcagcgg gagatggtcc ggaggaccaa cacaatgggg gaaatcatcg    4740
gtgtttgtct tgctctccgg accctgtaca acctttaaaa attgcccgt tctcgccttt    4800 cacggagcaa gatggcgctc ggcgttgcaa gcgcccagca caatgcgctc gcagaccacg    4860
ccggcataga cctgtcggac gtcgcctcgc ttgacttcca cagcagcagc ggcggccgca    4920
tgcactcacg gggggatcac atcgaaaccc gcgcagacgc agaggacgcg aaaagcatcc    4980
```

-continued

```
tcaaccgtct gaagggtggg aaagaaaaca tccacgagct tcggcagtgt gatttctcac    5040
ccgtacgccc caagccgggg acgaaagggt actctccaca agaattttta tttcgtcggc    5100
cgtgaagcgc gtcaagtgct ccacgtgaat gcggaggaag gcgaaaacgg catggagggt    5160
acgcggcctt gtaggatcgt tgtaccgtgg ctcagggttc gcactcacgc cattgctaag    5220
gatggttaag aaagttgagc taaaaaaaaa catccctaac ca                       5262
```

<210> SEQ ID NO 4
<211> LENGTH: 949
<212> TYPE: PRT
<213> ORGANISM: Artificial Sequence
<220> FEATURE:
<223> OTHER INFORMATION: Nannochloropsis gaditana

<400> SEQUENCE: 4

```
Met Ala Pro His Leu Ser Gly Leu Asn Phe His Ser Leu Val Lys Arg
1               5                   10                  15

Ser Ser Ala Ala Ala Leu Leu Phe Ser Leu Phe Ile Met Lys Leu Pro
            20                  25                  30

Cys Val Gly Ala Phe Gln Gly Val Val Arg Val Trp Ser Ser Ala Val
        35                  40                  45

Ala Pro Ser Arg Ala Ala Val Leu Thr Ser Phe Met Ser Pro Lys Arg
    50                  55                  60

His Val Leu Lys Arg Met Pro Ile Ser Ala Leu Cys Arg Arg Ser Thr
65                  70                  75                  80

Ile Met Ala Ser Arg Lys Ala Gly Ala Gly Gln Gly Glu His Glu Ala
                85                  90                  95

Glu Gly Glu Gly Ile Ser Pro Glu Ser Ile Ser Ser Thr Gly Ser Asn
            100                 105                 110

Ala Gly Gly Lys Gly Ile Gly Arg Gly Pro Arg Asn Arg Arg Lys Ile
        115                 120                 125

Ala Val Ser Ala Glu Glu Glu Phe Ser Ala Leu Ser Asp Ser Arg
    130                 135                 140

Thr Ser Val Ser Glu Glu Lys Asp Ser Ile Arg Arg Pro Arg Val Ile
145                 150                 155                 160

Ser Arg Pro Pro Ser Arg Pro Val Lys Arg Thr Met Thr Ile Asn Pro
                165                 170                 175

Asn Trp Arg Ala His Gly Gly Pro Glu Asn Ser Ile Lys Gly Pro Glu
            180                 185                 190

Glu Ala Ala Ser Ser Ser Ser Gly Thr Ala Gly Ser Gly Lys Ala Arg
        195                 200                 205

Val Gly Lys Asn Gly Pro Arg Gly Ala Ser Pro Leu Gly Ala Glu Val
    210                 215                 220

Pro Arg Tyr Val Glu Asp Glu Asp Gly Ile Thr Phe Pro Lys
225                 230                 235                 240

Asp Met Val Ile Arg Gly Leu Asp Ser Gln Ser Tyr Glu Glu Ala Arg
                245                 250                 255

Arg Gln Ala Val Leu Ser Asp Asp Glu Gly Glu Glu Glu Trp Ala
            260                 265                 270

Asp Glu Gly Val Met Val Glu Glu Glu Gly Glu Asp Phe Asp Glu
        275                 280                 285

Glu Glu Glu Glu Glu Asp Phe Asp Glu Glu Glu Glu Glu Asp Phe
    290                 295                 300

Asp Glu Gly Asp Glu Glu Glu Asp Gly Ala His Leu Pro Pro Val
305                 310                 315                 320
```

```
Arg Pro Val Ser Met Glu Arg Leu Arg Leu Ala Glu Ser Gly Asn
            325                 330                 335

Ile Phe Asn Pro Tyr Val Ala Arg Met His Thr Arg Ala Gly Thr Gly
        340                 345                 350

Glu Gly Pro Ser Gly Glu Ala Glu Asp Pro Gly Pro Met Asp Gly Gly
            355                 360                 365

Gly Leu Arg Phe Leu Glu Glu Asp Val Ser Pro Gly Glu Lys Arg Glu
        370                 375                 380

Glu Ala Arg Arg Ala Gln Ala Pro Ser Leu Pro Val Lys Phe Gln Tyr
385                 390                 395                 400

Lys Val Val Val Gly Ala Gly Thr Cys Pro Gly Cys Gly Asn Ala Phe
                405                 410                 415

Gln Thr Lys Asn Glu Ser Ser Pro Gly Phe Leu Pro Pro Asp Val Tyr
            420                 425                 430

Glu Arg Leu Gln Ala Gln Met Thr Ala Leu Arg Pro Gly Ala Pro Arg
        435                 440                 445

Lys Pro Arg Pro Asp Ala Pro Pro Leu Ser Lys Ser Ala Ala Gly Ala
    450                 455                 460

Leu Arg Lys Lys Thr Glu Thr Arg Gly Glu Glu Gly Asp Leu Phe Gln
465                 470                 475                 480

Gly Leu Ser Ala Glu Glu Val Glu Met Leu Leu Ser Gly Lys Ser
                485                 490                 495

Arg Glu Glu Phe Glu Ile Glu Arg Ala Ala Gly Arg Gly Arg Glu Ala
                500                 505                 510

Gln Gly Gly Glu Val Asp Leu Asp Leu Asp Glu Gly Lys Glu Glu
            515                 520                 525

Lys Glu Gly Glu Gly Arg Glu Gly Glu Gly Glu Gly Glu Glu
    530                 535                 540

Glu Glu Glu Glu Phe Arg Ala Val Ile Cys Gln Arg Cys His Lys Leu
545                 550                 555                 560

Lys His Tyr Gly Asp Val Glu Asp Ala Leu Arg Pro Gly Trp Ser Ala
            565                 570                 575

Asn Glu Leu Leu Thr Pro Glu Arg Phe Arg Glu Leu Val Ser Val Val
                580                 585                 590

Arg Arg Lys Arg Cys Ala Val Val Cys Leu Val Asp Ile Phe Asp Phe
        595                 600                 605

His Gly Ser Leu Leu Tyr Asn Leu Pro Arg Ile Val Gly Ser Asn Pro
    610                 615                 620

Val Leu Val Ala Val Asn Lys Ala Asp Leu Leu Pro Ala Asp Phe Ser
625                 630                 635                 640

Gln Asp Arg Val Arg Ile Trp Val Lys Gln Glu Leu Glu Lys Val Gly
                645                 650                 655

Met Thr Asp Val Ser Thr Arg Asp Ile His Leu Ile Ser Cys Lys Thr
            660                 665                 670

Gly Asn Asn Val Arg Pro Leu Leu Arg Ser Met Lys Gln Met Ala Arg
        675                 680                 685

Gln Arg Arg Arg Asp Leu Tyr Val Ile Gly Ala Ala Asn Val Gly Lys
    690                 695                 700

Ser Thr Phe Ile Asn Arg Leu Ile Glu Leu Gly Arg Ser Gly Gly Asp
705                 710                 715                 720

Ala Gln Arg Lys Lys Lys Lys Gln Gly Glu Gln Ser Lys Gly Gly
                725                 730                 735
```

```
Ser Leu Val Thr Thr Ser Ala Leu Pro Gly Thr Thr Leu Asp Phe Ile
            740                 745                 750

Glu Val Asp Leu Gly Asp Lys Val Ser Leu Tyr Asp Thr Pro Gly Leu
        755                 760                 765

Ile Leu Pro His Gln Ile Thr Thr Leu Leu Asn Thr Glu Glu Leu Lys
    770                 775                 780

Ala Val Ile Pro Gln Lys Arg Ile Asn His Val Thr Leu Arg Leu Lys
785                 790                 795                 800

Glu Gly Lys Ser Val Leu Leu Gly Gly Leu Val Arg Leu Asp Met Leu
                805                 810                 815

Glu Gly Arg Pro Phe Leu Phe Thr Phe Tyr Val Ser Asn Glu Val Lys
            820                 825                 830

Leu His Gln Thr Ala Thr Asp Arg Ala Gly Glu Phe Leu Asp Ser His
        835                 840                 845

Leu Gly Glu Leu Ile Ser Pro Pro Phe Thr Gln Glu Arg Arg Ala Ala
    850                 855                 860

Met Gly Pro Trp Val Pro Arg Asp Phe Glu Ile Glu Gly Thr Gly Trp
865                 870                 875                 880

Lys Thr Ser Ala Val Asp Ile Val Ile Ser Gly Leu Gly Trp Ile Ser
                885                 890                 895

Val Thr Gly Ala Leu Asp Cys Lys Val Arg Val Met Ala Pro Glu Ala
            900                 905                 910

Val Gly Val Arg Leu Arg Ser Pro Leu Met Pro Tyr Glu Thr Trp Ala
        915                 920                 925

Thr Thr Ala Lys Trp Thr Gly Leu Arg Ala Val Lys Ser Asp Lys Gln
    930                 935                 940

Lys Gly Ser Ser Arg
945

<210> SEQ ID NO 5
<211> LENGTH: 2874
<212> TYPE: DNA
<213> ORGANISM: Artificial Sequence
<220> FEATURE:
<223> OTHER INFORMATION: Codon-optimized NgNOA-encoding sequence

<400> SEQUENCE: 5
ggatcctcta gaatggctcc ccacctctcc ggcctcaact tccactccct cgtcaagcgc      60
tcctccgctg ctgctctcct cttctccctc ttcatcatga agctcccctg cgtcggcgct     120
ttccagggcg tcgtccgcgt ctggtcctcc gctgtcgctc cctcccgcgc tgctgtcctc     180
acctccttca tgtcccccaa gcgccacgtc ctcaagcgca tgcccatctc cgctctctgc     240
cgccgctcca ccatcatggc ttcccgcaag gctggcgctg ccagggcgga gcacgaggct     300
gagggcgagg gcatctcccc cgagtccatc tcctccaccg gctccaacgc tggcggcaag     360
ggcatcggcc gcggcccccg caaccgccgc aagatcgctg tctccgctga ggaggaggag     420
ttctccgctc tctccgactc ccgcacctcc gtctccgagg agaaggactc catccgccgc     480
ccccgcgtca tctcccgccc ccctcccgc ccgtcaagc gcaccatgac catcaacccc     540
aactggcgcg ctcacggcgg ccccgagaac tccatcaagg gccccgagga ggctgcttcc     600
tcctcctccg gcaccgctgg ctccggcaag gctcgcgtcg caagaacgg ccccgcggc     660 gcttcccccc tcggcgctga ggtcccccgc tacgtcgagg acgaggacga ggacggcatc     720
accttcccca aggacatggt catcgcggg ctcgactccc agtcctacga ggaggctcgc     780
cgccaggctg tcctctccga cgacgagggc gaggaggag agtgggctga cgaggcgtc     840
```

```
atggtcgagg aggaggaggg cgaggacttc gacgaggagg aggaggagga ggacttcgac    900
gaggaggagg aggaggagga cttcgacgag gcgacgagg aggaggagga cggcgctcac    960
```

```
atggtcgagg aggaggaggg cgaggacttc gacgaggagg aggaggagga ggacttcgac    900
gaggaggagg aggaggagga cttcgacgag gcgacgagg aggaggagga cggcgctcac    960
ctccccccg tccgcccgt ctccatggag gagcgcctcc gcctcgctga gtccggcaac    1020
atcttcaacc cctacgtcgc tcgcatgcac acccgcgctg caccggcga gggcccctcc    1080
ggcgaggctg aggacccgg ccccatggac ggcggcggcc tccgcttcct cgaggaggac    1140
gtctcccccg cgagaagcg cgaggaggct cgccgcgctc aggctccctc cctccccgtc    1200
aagttccagt acaaggtcgt cgtcggcgct ggcacctgcc ccggctgcgg caacgctttc    1260
cagaccaaga cgagtcctc ccccggcttc ctcccccccg acgtctacga gcgcctccag    1320
gctcagatga ccgctctccg ccccggcgct ccccgcaagc cccgccccga cgctccccc    1380
ctctccaagt ccgctgctgg cgctctccgc aagaagaccg agaccgcgg cgaggagggc    1440
gacctcttcc agggcctctc cgctgaggag gaggtcgaga tgctcctctc cggcaagtcc    1500
cgcgaggagt tcgagatcga gcgcgctgct ggccgcggcc gcgaggctca gggcggcgag    1560
gtcgacctcg acctcgacga ggagggcaag gaggagaagg agggcgaggg ccgcgagggc    1620
gaggaggcg cgagggcga ggaggaggag gaggagttcc gcgctgtcat ctgccagcgc    1680
tgccacaagc tcaagcacta cggcgacgtc gaggacgctc tccgccccgg ctggtccgct    1740
aacgagctcc tcacccccga gcgcttccgc gagctcgtct ccgtcgtccg ccgcaagcgc    1800
tgcgctgtcg tctgcctcgt cgacatcttc gacttccacg gctccctcct ctacaacctc    1860
ccccgcatcg tcggctccaa ccccgtcctc gtcgctgtca caaggctga cctcctcccc    1920
gctgacttct cccaggaccg cgtccgcatc tgggtcaagc aggagctcga aaggtcggc    1980
atgaccgacg tctccacccg cgacatccac ctcatctcct gcaagaccgg caacaacgtc    2040
cgccccctcc tccgctccat gaagcagatg gctcgccagc gccgccgcga cctctacgtc    2100
atcggcgctg ctaacgtcgg caagtccacc ttcatcaacc gcctcatcga gctcggccgc    2160
tccggcggcg acgctcagcg caagaagaag aagaagcagg gcgagcagtc caagggcggc    2220
tccctcgtca ccacctccgc tctccccggc accaccctcg acttcatcga ggtcgacctc    2280
ggcgacaagg tctccctcta cgacacccc ggcctcatcc tccccacca gatcaccacc    2340
ctcctcaaca ccgaggagct caaggctgtc atccccagaa gcgcatcaa ccacgtcacc    2400
ctccgcctca aggagggcaa gtccgtcctc tcggcggcc tcgtccgcct cgacatgctc    2460
gagggccgcc ccttcctctt caccttctac gtctccaacg aggtcaagct ccaccagacc    2520
gctaccgacc gcgctggcga gttcctcgac tccaccctcg cgagctcat ctccccccc    2580
ttcacccagg agcgccgcgc tgctatgggc ccctgggtcc ccgcgactt cgagatcgag    2640
ggcaccggct ggaagacctc cgctgtcgac atcgtcatct ccggcctcgg ctggatctcc    2700
gtcaccggcg ctctcgactg caaggtccgc gtcatggctc ccgaggctgt cggcgtccgc    2760
ctccgctccc ccctcatgcc ctacgagacc tgggctacca ccgctaagtg gaccggcctc    2820
cgcgctgtca agtccgacaa gcagaagggc tcctcccgct aagaattcca tatg         2874
```

<210> SEQ ID NO 6
<211> LENGTH: 6605
<212> TYPE: DNA
<213> ORGANISM: Artificial Sequence
<220> FEATURE:
<223> OTHER INFORMATION: pH4-NOAOE

<400> SEQUENCE: 6

```
ctaaattgta agcgttaata ttttgttaaa attcgcgtta aattttttgtt aaatcagctc      60 attttttaac caataggccg aaatcggcaa aatcccttat aaatcaaaag aatagaccga     120 gataggggttg agtgttgttc cagtttggaa caagagtcca ctattaaaga acgtggactc    180
caacgtcaaa gggcgaaaaa ccgtctatca gggcgatggc ccactacgtg aaccatcacc    240
ctaatcaagt tttttggggt cgaggtgccg taaagcacta aatcggaacc ctaaagggag    300
cccccgattt agagcttgac ggggaaagcc ggcgaacgtg gcgagaaagg aagggaagaa    360
agcgaaagga gcgggcgcta gggcgctggc aagtgtagcg gtcacgctgc gcgtaaccac    420
cacacccgcc gcgcttaatg cgccgctaca gggcgcgtcc cattcgccat tcaggctgcg    480
caactgttgg gaagggcgat cggtgcgggc ctcttcgcta ttacgccagc tggcgaaagg    540
gggatgtgct gcaaggcgat taagttgggt aacgccaggg ttttcccagt cacgacgttg    600
taaaacgacg gccagtgagc gcgcgtaata cgactcacta tagggcgaat tggagctcgc    660
aatctcacgc accaggcgct ggaagggcaa cttgcggatg agaaggtccg tggacttctg    720
gtaacgacgg atctcacgca gagcgacggt tccagggcga taacgtgggg gcttcttgac    780
tcctccggta gccggagcgg acttgcgggc agccttggtg gcaagctgct tgcgcggcgc    840
tttgcctccg gtggatttac gggcggtttg cttggttcgg gccatttttga cggttttttt    900 tacaagagaa gagttcttga aatttgtgag gttaaagtgt gtggcttccg ccgtagtcaa    960
ggagcgtgcg gttgccgatc gcaccggtac gttctgtaga aatgaacaca gtgtgttgaa   1020
ttgaaagtat ggcgcaggta tggtgtgtga taagtagcag ccgcgccgag acaaacaaac   1080
tttggtttct acgacaatct ctgtagacaa gtactagaaa cccgtttgaa cgagcataaa   1140
tctgcaccgg caggccacca gacatcgttt caacgtaata ttctacgtaa ccattttatc   1200
ccaggaaacc tacggcctgt gaaccaccga gacggagcac tcacaattcg ctctcggcaa   1260
caaccgacaa tcgtcttact cacagtcaat accgaaaaca aacaacagcc atggccaagt   1320
tgaccagtgc cgttccggtg ctcaccgcgc gcgacgtcgc cggagcggtc gagttctgga   1380
ccgaccggct cgggttctcc cgggacttcg tggaggacga cttcgccggt gtggtccggg   1440
acgacgtgac cctgttcatc agcgcggtcc aggaccaggt ggtgccggac aacacccctgg   1500 cctgggtgtg ggtgcgcggc ctggacgagc tgtacgccga gtggtcggag gtcgtgtcca   1560
cgaacttccg ggacgcctcc gggccggcca tgaccgagat cggcgagcag ccgtgggggc   1620
gggagttcgc cctgcgcgac ccggccggca actgcgtgca cttcgtggcc gaggagcagg   1680
actgaccgac gccgaccaac accgccggtc cgacggcggc ccacgggtcc caggccttct   1740
agaatggtcc ccactggttg tatgagatca agaacaaaac agagtactgc tgctgacgga   1800
agaaggtcga ttggaagtcg atccaacgct ggactggtca tgttctttag tatgactatc   1860
ttatcgacac gacgatttgc ggcagcttgg gttttttcaga gtagtggaat acaacgatca   1920
ataccatcca cgcataggat gcgaacgaat tttgctttgt cgacgcgctg ctttgcttct   1980
tcatccgaca accatgacga agaggaacaa cgagactctc cgaaacaaag atccaaacgc   2040
agccaaacta atcggtccaa gaaattcaaa attgctgaat caatcgacca gagcaaaata   2100
gataagctag cacaagcatt cgatgaactc gctcggaagg aaggcttcga ctcgtcaaca   2160
gcacgctttg ccgacgatgt gacgttcgag acaagtttg acgacgattc gtttctggac    2220
gatgacgatg ataacaacaa agataaagtg ggaaacttgc acctagatgc atccatgttc   2280
agtttaagtg actttataga taagagtgag gaagatggcg gcaatccaac cgatcaagat   2340
gacgaggact accttgattt tggtgcagac attgacatga gtatagaagc aaggattgcc   2400
```

```
gctgccaaac gggatatgga tctcggtcga gtcagcgccc ctcccgatat gagatcctcg    2460
cgcagggagg taactgcagc cgaccttcgc aaacttggat ttcgaaccga ggcaaaccca    2520
ttcggcaacg acgaaactcc acggaaggag cgcttccagt tggtaacaaa ctccatgtcg    2580
tgctccgcct gtggatcgga cttcaatgc cacaacgaag atcggcccgg atatctgcct    2640
cctgaaaagt tcgctacgca aacagcactt ggaaaaatag aacagatgca aaagttgcag    2700
gataaagcag aaaaagcgga atggacacct gaagatgaga ttgaatggtt gattcagact    2760
cagggcaaaa aggatccgaa caaagaaatg caggaggtgc cccagatcga tgttgattct    2820
ttggcagggg aaatgggcct tgacctcgta gagctttcca aaaagatggt tatttgcaag    2880
cgctgtcacg gtctgcaaaa ctttggaaaa gtgcaagatt ccctccgacc tgggtggacg    2940
aaggagccac tgttgtcgca ggagaaattt cgtgaattgt taaggccaat caaggaaaag    3000
ccggcagtta tcgttgcatt ggtcgatctt tttgattttt cggggtctgt gctccctgag    3060
cttgatgaaa tcgctggtga aaaccctgta attcttgcgg ccaacaaggc ggatcttctt    3120
ccaagtgaaa tgggacgcgt gcgagctgag agttgggttc gacgcgagct cgaataccttt   3180 ggagtcaagt cgttggccgg tatgagagga gcagttcggc ttgtcagctg caagactgga    3240
gctgggatta atgatttgct ggagaaagca agaggattag ccgaggaaat cgacggcgac    3300
atatacgtcg tcgggggctgc aaatgcagga aaaagtacgc ttttgaattt tgttctaggt   3360
caggacaagg tgaacagatc acccggaaaa gcacgagcag gcaacaggaa tgccttcaag   3420
ggcgcggtga cgacaagtcc actgccaggc acaacgctta agttcatcaa agtcgattta   3480
ggcggcggtc gaagtctata tgacactcct ggtcttctgg tattaggcac tgtgacacag   3540
ttactgaccc ccgaagagct gaagatagtt gttcccaaaa agtatgtcaa accgatcaaa   3600
ctgatattcg attcacagtc aataatgttc aaactaacac ctcgttcctc aaacaggcca   3660
attgaacctg tcaccctccg gctctctacc ggaaagtgcg ttctagttgg aggattggcc    3720
cgcatcgagt taatcggcga ctcaagaccc tttatgttca cattttttgt tgctaatgag    3780
atcaagctcc accctactga catagagaga gccgatgagt tcgttctaaa gcacgctggt    3840
ggcatgttga ctccaccgct agcacccgga ccaaaacgta tggaagagat tggagaattt    3900
gaagatcaca tcgtggatat ccagggtgct ggctggaaag aagctgctgc tgatatcagt    3960
cttaccggac taggatgggt ggccgttaca ggagcaggga cagcgcaagt aaaaataagt    4020
gttccgaaag gtattggtgt atcggtgcgg cctccgctta tgcctttcga tatctggaaa    4080
gttgcatcga agtataccgg aagtcgagct gtaagaaagt catccaaact ggcgaatggg    4140
aaacgaagaa aaggtgtagg gcgtaattag gaattctcga gctacctcga ctttggctgg    4200
gacactttca gtgaggacaa gaagcttcag aagcgtgcta tcgaactcaa ccagggacgt    4260
gcggcacaaa tgggcatcct tgctctcatg gtgcacgaac agttgggagt ctctatcctt    4320
ccttaaaaat ttaattttca ttagttgcag tcactccgct ttggtttcac agtcaggaat    4380
aacactagct cgtcttcagg tacccagctt ttgttcccttt agtgagggt taattgcgcg    4440 cttggcgtaa tcatggtcat agctgttttcc tgtgtgaaat tgttatccgc tcacaattcc    4500
acacaacata cgagccggaa gcataaagtg taaagcctgg ggtgcctaat gagtgagcta    4560
actcacatta attgcgttgc gctcactgcc cgctttccag tcgggaaacc tgtcgtgcca    4620
gctgcattaa tgaatcggcc aacgcgcggg gagaggcggt ttgcgtattg ggcgctcttc    4680
cgcttcctcg ctcactgact cgctgcgctc ggtcgttcgg ctgcggcgag cggtatcagc    4740
```

```
tcactcaaag gcggtaatac ggttatccac agaatcaggg gataacgcag gaaagaacat      4800
gtgagcaaaa ggccagcaaa aggccaggaa ccgtaaaaag gccgcgttgc tggcgttttt      4860
ccataggctc cgcccccctg acgagcatca caaaaatcga cgctcaagtc agaggtggcg      4920
aaacccgaca ggactataaa gataccaggc gtttccccct ggaagctccc tcgtgcgctc      4980
tcctgttccg accctgccgc ttaccggata cctgtccgcc tttctccctt cgggaagcgt      5040
ggcgctttct catagctcac gctgtaggta tctcagttcg gtgtaggtcg ttcgctccaa      5100
gctgggctgt gtgcacgaac cccccgttca gcccgaccgc tgcgccttat ccggtaacta      5160
tcgtcttgag tccaacccgg taagacacga cttatcgcca ctggcagcag ccactggtaa      5220
caggattagc agagcgaggt atgtaggcgg tgctacagag ttcttgaagt ggtggcctaa      5280
ctacggctac actagaagga cagtatttgg tatctgcgct ctgctgaagc cagttacctt      5340
cggaaaaaga gttggtagct cttgatccgg caaacaaacc accgctggta gcggtggttt      5400
ttttgtttgc aagcagcaga ttacgcgcag aaaaaaagga tctcaagaag atcctttgat      5460
cttttctacg gggtctgacg ctcagtggaa cgaaaactca cgttaaggga ttttggtcat      5520
gagattatca aaaaggatct tcacctagat ccttttaaat taaaaatgaa gttttaaatc      5580
aatctaaagt atatatgagt aaacttggtc tgacagttac caatgcttaa tcagtgaggc      5640
acctatctca gcgatctgtc tatttcgttc atccatagtt gcctgactcc ccgtcgtgta      5700
gataactacg atacgggagg gcttaccatc tggccccagt gctgcaatga taccgcgaga      5760
cccacgctca ccggctccag atttatcagc aataaaccag ccagccggaa gggccgagcg      5820
cagaagtggt cctgcaactt tatccgcctc catccagtct attaattgtt gccgggaagc      5880
tagagtaagt agttcgccag ttaatagttt gcgcaacgtt gttgccattg ctacaggcat      5940
cgtggtgtca cgctcgtcgt ttggtatggc ttcattcagc tccggttccc aacgatcaag      6000
gcgagttaca tgatccccca tgttgtgcaa aaaagcggtt agctccttcg gtcctccgat      6060
cgttgtcaga agtaagttgg ccgcagtgtt atcactcatg gttatggcag cactgcataa      6120
ttctcttact gtcatgccat ccgtaagatg cttttctgtg actggtgagt actcaaccaa      6180
gtcattctga atagtgtata tgcggcgacc gagttgctct tgcccggcgt caatacggga      6240
taataccgcg ccacatagca gaactttaaa agtgctcatc attggaaaac gttcttcggg      6300
gcgaaaactc tcaaggatct taccgctgtt gagatccagt tcgatgtaac ccactcgtgc      6360
acccaactga tcttcagcat cttttacttt caccagcgtt tctgggtgag caaaaacagg      6420
aaggcaaaat gccgcaaaaa agggaataag ggcgacacgg aaatgttgaa tactcatact      6480 cttcctttttt caatattatt gaagcattta tcagggttat tgtctcatga gcggatacat      6540
atttgaatgt atttagaaaa ataaacaaat aggggttccg cgcacatttc cccgaaaagt      6600
gccac                                                                 6605
```

<210> SEQ ID NO 7
<211> LENGTH: 5198
<212> TYPE: DNA
<213> ORGANISM: Artificial Sequence
<220> FEATURE:
<223> OTHER INFORMATION: PCT2Ng

<400> SEQUENCE: 7

```
gtggcacttt tcggggaaat gtgcgcggaa cccctatttg tttatttttc taaatacatt        60
caaatatgta tccgctcatg agacaataac cctgataaat gcttcaataa tattgaaaaa       120
ggaagagtat gagtattcaa catttccgtg tcgcccttat tccctttttt gcggcatttt       180
```

```
gccttcctgt ttttgctcac ccagaaacgc tggtgaaagt aaaagatgct gaagatcagt      240
tgggtgcacg agtgggttac atcgaactgg atctcaacag cggtaagatc cttgagagtt      300
ttcgccccga agaacgtttt ccaatgatga gcacttttaa agttctgcta tgtggcgcgg      360
tattatcccg tattgacgcc gggcaagagc aactcggtcg ccgcatacac tattctcaga      420
atgacttggt tgagtactca ccagtcacag aaaagcatct tacggatggc atgacagtaa      480
gagaattatg cagtgctgcc ataaccatga gtgataacac tgcggccaac ttacttctga      540
caacgatcgg aggaccgaag gagctaaccg cttttttgca caacatgggg gatcatgtaa      600
ctcgccttga tcgttgggaa ccggagctga atgaagccat accaaacgac gagcgtgaca      660
ccacgatgcc tgtagcaatg gcaacaacgt tgcgcaaact attaactggc gaactactta      720
ctctagcttc ccggcaacaa ttaatagact ggatggaggc ggataaagtt gcaggaccac      780
ttctgcgctc ggcccttccg gctggctggt ttattgctga taaatctgga gccggtgagc      840
gtgggtctcg cggtatcatt gcagcactgg ggccagatgg taagccctcc cgtatcgtag      900
ttatctacac gacggggagt caggcaacta tggatgaacg aaatagacag atcgctgaga      960
taggtgcctc actgattaag cattggtaac tgtcagacca agtttactca tatatacttt     1020
agattgattt aaaacttcat ttttaattta aaaggatcta ggtgaagatc ctttttgata     1080
atctcatgac caaaatccct aacgtgagt tttcgttcca ctgagcgtca gaccccgtag     1140
aaaagatcaa aggatcttct tgagatcctt ttttctgcg cgtaatctgc tgcttgcaaa     1200
caaaaaaacc accgctacca gcggtggttt gtttgccgga tcaagagcta ccaactcttt     1260
ttccgaaggt aactggcttc agcagagcgc agataccaaa tactgtcctt ctagtgtagc     1320
cgtagttagg ccaccacttc aagaactctg tagcaccgcc tacatacctc gctctgctaa     1380
tcctgttacc agtggctgct gccagtggcg ataagtcgtg tcttaccggg ttggactcaa     1440
gacgatagtt accggataag gcgcagcggt cgggctgaac ggggggttcg tgcacacagc     1500
ccagcttgga gcgaacgacc tacaccgaac tgagatacct acagcgtgag ctatgagaaa     1560
gcgccacgct tcccgaaggg agaaaggcgg acaggtatcc ggtaagcggc agggtcggaa     1620
caggagagcg cacgagggag cttccagggg gaaacgcctg gtatctttat agtcctgtcg     1680
ggtttcgcca cctctgactt gagcgtcgat ttttgtgatg ctcgtcaggg ggcggagcc      1740 tatgaaaaa cgccagcaac gcggccttt tacggttcct ggccttttgc tggccttttg     1800
ctcacatgtt ctttcctgcg ttatcccctg attctgtgga taaccgtatt accgcctttg     1860
agtgagctga taccgctcgc cgcagccgaa cgaccgagcg cagcgagtca gtgagcgagg     1920
aagcggaaga gcgcccaata cgcaaaccgc ctctccccgc gcgttggccg attcattaat     1980
gcagctggca cgacaggttt cccgactgga aagcgggcag tgagcgcaac gcaattaatg     2040
tgagttagct cactcattag gcaccccagg ctttacactt tatgcttccg gctcgtatgt     2100
tgtgtggaat tgtgagcgga taacaatttc acacaggaaa cagctatgac catgattacg     2160
ccaagcgcgc aattaaccct cactaaaggg aacaaaagct ggagctcagc tgctgccccg     2220
accgtatctc caagtcagac atgaaatctt cagttgcgtt aaaaactcta cgatgctacc     2280
agcgttaaat aaccttgccc acgcctttaa acgtacccga tcattaacat atcgactggc     2340
tgccttggct ttgcaccagc catcatcaga cttaacgatg gtatgttgc ttgccttttcc     2400 tgcttgaagg gggtccgact ctctgctttc tcgatcgcgg gtgtgacctc tgaattggaa     2460
tgtaaaaatg taagaagcga cgtgtccggt aaagaaatgc ccaagctcca tcaaatctgc     2520
```

-continued

```
gttgtcggcg accaaaccat gctggctcgt cgacctgccc cggatgcagg agcatggcac    2580
tcggcggcat ggcacttgag cctcgcggga ggaatgtgtg tggttgggcg caggctgtgg    2640
acggcccccc tccagcgaag cggtcgcctc cctttccgac gctttgtgca cgttgtctgg    2700
tgtcctctgt ctcacgcacc tcttcaccga cgtggtgtcc ctcttgttgc tggtgaggga    2760
cttggaatgt ggtcctggtt ctatcctggg cgcgtgtgtt ccttttttc tctaccgtta    2820 ttctctccat ttctgatgtc tcaccaccat ctccctcacc ctccaaccgc gtcgttgtgc    2880
caaaatcata cagcaggatc gatggccaag ttgaccagtg ccgttccggt gctcaccgcg    2940
cgcgacgtcg ccggagcggt cgagttctgg accgaccggc tcgggttctc ccgggacttc    3000
gtggaggacg acttcgccgg tgtggtccgg gacgacgtga ccctgttcat cagcgcggtc    3060
caggaccagg tggtgccgga caacaccctg gcctgggtgt gggtgcgcgg cctggacgag    3120
ctgtacgccg agtggtcgga ggtcgtgtcc acgaacttcc gggacgcctc cgggccggcc    3180
atgaccgaga tcggcgagca gccgtggggg cgggagttcg ccctgcgcga cccgccggc    3240 aactgcgtgc acttcgtggc cgaggagcag gactaaatcg atcttcctta aaaatttaat    3300
tttcattagt tgcagtcact ccgctttggt ttcacagtca ggaataacac tagctcgtct    3360
tcaccatgga tgccaatctc gcctattcat ggtgtataaa agttcaacat ccaaagctag    3420
aacttttgga aagagaaaga atatccgaat agggcacggc gtgccgtatt gttggagtgg    3480
actagcagaa agtgaggaag gcacaggatg agttttctcg agagctgctg ccccgaccgt    3540
atctccaagt cagacatgaa atcttcagtt gcgttaaaaa ctctacgatg ctaccagcgt    3600
taaataacct tgcccacgcc tttaaacgta cccgatcatt aacatatcga ctggctgcct    3660
tggctttgca ccagccatca tcagacttaa cgatgggtat gttgcttgcc tttcctgctt    3720 gaaggggggtc cgactctctg ctttctcgat cgcgggtgtg acctctgaat tggaatgtaa    3780
aaatgtaaga agcgacgtgt ccggtaaaga aatgcccaag ctccatcaaa tctgcgttgt    3840
cggcgaccaa accatgctgg ctcgtcgacc tgccccggat gcaggagcat ggcactcggc    3900
ggcatggcac ttgagcctcg cggaggaat gtgtgtggtt gggcgcaggc tgtggacggc    3960 cccctccag cgaagcggtc gcctcccttt ccgacgcttt gtgcacgttg tctggtgtcc    4020
tctgtctcac gcacctcttc accgacgtgg tgtccctctt gttgctggtg agggacttgg    4080
aatgtggtcc tggttctatc ctgggcgcgt gtgttccttt ttttctctac cgttattctc    4140
tccatttctg atgtctcacc accatctccc tcaccctcca accgcgtcgt tgtgccaaaa    4200
tcatacagca ggaggcctgt cgacggcgcg ccggatccag atctgaattc gatatcacgc    4260
gtccatggca tatggctagc gcggccgcct cgagtctaga cttccttaaa aatttaatttt    4320 tcattagttg cagtcactcc gctttggttt cacagtcagg aataacacta gctcgtcttc    4380
accatggatg ccaatctcgc ctattcatgg tgtataaaag ttcaacatcc aaagctagaa    4440
cttttggaaa gagaaagaat atccgaatag ggcacggcgt gccgtattgt tggagtggac    4500
tagcagaaag tgaggaaggc acaggatgag ttttctcgag ggtacccaat cgccctata    4560 gtgagtcgta ttacgcgcgc tcactggccg tcgttttaca acgtcgtgac tgggaaaacc    4620
ctggcgttac ccaacttaat cgccttgcag cacatccccc tttcgccagc tggcgtaata    4680
gcgaagaggc ccgcaccgat cgcccttccc aacagttgcg cagcctgaat ggcgaatggg    4740
acgcgccctg tagcggcgca ttaagcgcgg cgggtgtggt ggttacgcgc agcgtgaccg    4800
ctacacttgc cagcgcccta gcgcccgctc ctttcgcttt cttcccttcc tttctcgcca    4860
cgttcgccgg ctttccccgt caagctctaa atcgggggct ccctttaggg ttccgattta    4920
```

```
gtgctttacg gcacctcgac cccaaaaaac ttgattaggg tgatggttca cgtagtgggc    4980
catcgccctg atagacggtt tttcgccctt tgacgttgga gtccacgttc tttaatagtg    5040
gactcttgtt ccaaactgga acaacactca accctatctc ggtctattct tttgatttat    5100
aagggatttt gccgatttcg gcctattggt taaaaaatga gctgatttaa caaaaattta    5160
acgcgaattt taacaaaata ttaacgctta caatttag                            5198
```

<210> SEQ ID NO 8
<211> LENGTH: 31
<212> TYPE: DNA
<213> ORGANISM: Artificial Sequence
<220> FEATURE:
<223> OTHER INFORMATION: primer

<400> SEQUENCE: 8

```
tttatctaga atggtcccca ctggttgtat g                                   31
```

<210> SEQ ID NO 9
<211> LENGTH: 36
<212> TYPE: DNA
<213> ORGANISM: Artificial Sequence
<220> FEATURE:
<223> OTHER INFORMATION: primer

<400> SEQUENCE: 9

```
tttagaattc ctaattacgc cctacacctt ttcttc                              36
```

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10

```
cgaagtcaac caggaaacca a                                              21
```

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11

```
gtgcaagaga ccggacatac c                                              21
```

<210> SEQ ID NO 12
<211> LENGTH: 21
<212> TYPE: DNA
<213> ORGANISM: Artificial Sequence
<220> FEATURE:
<223> OTHER INFORMATION: primer

<400> SEQUENCE: 12

```
ctgggagctt tactgcttgg a                                              21
```

<210> SEQ ID NO 13
<211> LENGTH: 21
<212> TYPE: DNA
<213> ORGANISM: Artificial Sequence
<220> FEATURE:
<223> OTHER INFORMATION: primer

```
<400> SEQUENCE: 13
atggctcgag atcgacgtaa a                                               21

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
cctgaaaagt tcgctacgca                                                 20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
cggatccttt ttgccctgag                                                 20
```